United States Patent
Gouliaev et al.

(10) Patent No.: US 7,704,925 B2
(45) Date of Patent: *Apr. 27, 2010

(54) LIGATIONAL ENCODING USING BUILDING BLOCK OLIGONUCLEOTIDES

(75) Inventors: Alex Haahr Gouliaev, Vekso Sjaelland (DK); Henrik Pedersen, Bagsvaerd (DK)

(73) Assignee: Nuevolution A/S, Copenhagen O (DK)

( * ) Notice: Subject to any disclaimer, the term of this patent is extended or adjusted under 35 U.S.C. 154(b) by 118 days.

This patent is subject to a terminal disclaimer.

(21) Appl. No.: 10/593,868

(22) PCT Filed: Mar. 22, 2005

(86) PCT No.: PCT/DK2005/000199

§ 371 (c)(1),
(2), (4) Date: Aug. 26, 2008

(87) PCT Pub. No.: WO2005/090566

PCT Pub. Date: Sep. 29, 2005

(65) Prior Publication Data

US 2009/0011957 A1    Jan. 8, 2009

Related U.S. Application Data

(63) Continuation-in-part of application No. PCT/DK2004/000195, filed on Mar. 22, 2004, and a continuation-in-part of application No. 10/549,619, filed as application No. PCT/DK2004/000195 on Mar. 22, 2004.

(60) Provisional application No. 60/585,008, filed on Jul. 6, 2004.

(30) Foreign Application Priority Data

Jul. 6, 2004 (DK) ................. 2004 01067

(51) Int. Cl.
| | |
|---|---|
| *C40B 50/00* | (2006.01) |
| *C40B 30/00* | (2006.01) |
| *C40B 20/04* | (2006.01) |
| *C40B 50/10* | (2006.01) |
| *C40B 50/16* | (2006.01) |
| *C40B 40/00* | (2006.01) |
| *C07H 21/02* | (2006.01) |
| *C12Q 1/68* | (2006.01) |

(52) U.S. Cl. .............. 506/23; 506/4; 506/7; 506/13; 506/28; 435/6; 435/91.2; 536/23.1

(58) Field of Classification Search ............... None
See application file for complete search history.

(56) References Cited

U.S. PATENT DOCUMENTS

| | | |
|---|---|---|
| 4,822,731 A | 4/1989 | Watson et al. |
| 5,476,930 A | 12/1995 | Letsinger et al. |
| 5,503,805 A | 4/1996 | Sugarman et al. |
| 5,571,903 A | 11/1996 | Gryaznov et al. |
| 5,573,905 A | 11/1996 | Lerner et al. |
| 5,639,603 A | 6/1997 | Dower et al. |
| 5,665,975 A | 9/1997 | Kedar et al. |
| 5,681,943 A | 10/1997 | Letsinger et al. |
| 5,708,153 A | 1/1998 | Dower et al. |
| 5,723,598 A | 3/1998 | Lerner et al. |
| 5,741,643 A | 4/1998 | Gryaznov et al. |
| 5,770,358 A | 6/1998 | Dower et al. |
| 5,780,613 A | 7/1998 | Letsinger et al. |
| 5,789,162 A | 8/1998 | Dower et al. |
| 5,830,658 A | 11/1998 | Gryaznov et al. |
| 5,843,650 A | 12/1998 | Segev |
| 6,056,926 A | 5/2000 | Sugarman et al. |
| 6,060,596 A | 5/2000 | Lerner et al. |
| 6,140,493 A | 10/2000 | Dower et al. |
| 6,143,497 A | 11/2000 | Dower et al. |
| 6,143,503 A | 11/2000 | Baskerville et al. |
| 6,165,717 A | 12/2000 | Dower et al. |
| 6,165,778 A | 12/2000 | Kedar et al. |
| 6,207,446 B1 | 3/2001 | Szostak et al. |
| 6,297,053 B1 | 10/2001 | Stemmer |
| 6,416,949 B1 | 7/2002 | Dower et al. |
| 6,429,300 B1 | 8/2002 | Kurz et al. |
| 6,593,088 B1 | 7/2003 | Saito et al. |
| 6,620,587 B1 | 9/2003 | Taussig et al. |
| 2003/0004122 A1 | 1/2003 | Beigelman et al. |

| | | |
|---|---|---|
| 2005/0025766 A1 | 2/2005 | Liu et al. |
| 2005/0042669 A1 | 2/2005 | Liu et al. |
| 2005/0142583 A1 | 6/2005 | Liu |
| 2005/0170376 A1 | 8/2005 | Liu |

FOREIGN PATENT DOCUMENTS

| | | |
|---|---|---|
| EP | 0324616 | 7/1989 |
| EP | 0604552 | 4/1993 |
| EP | 0643778 | 10/1993 |
| EP | 0695305 | 10/1994 |
| EP | 0776330 | 10/1996 |
| EP | 0773227 | 5/1997 |
| EP | 1533385 | 5/2005 |
| WO | 9005785 | 5/1990 |
| WO | 9105058 | 4/1991 |
| WO | 9303172 | 2/1993 |
| WO | 9504160 | 2/1995 |
| WO | 9512608 | 5/1995 |
| WO | 9609316 | 3/1996 |
| WO | 9612014 | 4/1996 |
| WO | 9635699 | 11/1996 |
| WO | 9831700 | 7/1998 |
| WO | 9856904 | 12/1998 |
| WO | 9951773 | 10/1999 |
| WO | 0021909 | 4/2000 |
| WO | 0023458 | 4/2000 |
| WO | 0032823 | 6/2000 |
| WO | 0047775 | 8/2000 |
| WO | 0061775 | 10/2000 |
| WO | 0100876 | 1/2001 |
| WO | 02074929 | 9/2002 |
| WO | 02102820 | 12/2002 |
| WO | 02103008 | 12/2002 |
| WO | 03078050 | 9/2003 |
| WO | 03078445 | 9/2003 |
| WO | 03078446 | 9/2003 |
| WO | 03078625 | 9/2003 |
| WO | 03078626 | 9/2003 |
| WO | 03078627 | 9/2003 |
| WO | 03082901 | 10/2003 |
| WO | 04001042 | 12/2003 |
| WO | 2004009814 | 1/2004 |
| WO | 2004016767 | 2/2004 |
| WO | 2004024929 | 3/2004 |
| WO | 2004039825 | 5/2004 |
| WO | 2004056994 | 7/2004 |
| WO | 2004074429 | 9/2004 |
| WO | 2004074501 | 9/2004 |
| WO | 2004083427 | 9/2004 |
| WO | 2004099441 | 11/2004 |
| WO | 2004013070 | 12/2004 |
| WO | 2004110964 | 12/2004 |
| WO | 2005003778 | 1/2005 |
| WO | 2005026387 | 3/2005 |
| WO | 2006048025 | 5/2006 |
| WO | 2006053571 | 5/2006 |

OTHER PUBLICATIONS

Nemoto, N. et al. "In vitro virus: bonding of mRNA bearing puromycin at the 3'-terminal end to the C-terminal end of its encoded protein on the ribosome in vitro". FEBS Lett. Sep. 8, 1997;414(2):405-8.

Roberts, RW et al. "RNA-peptide fusions for the in vitro selection of peptides and proteins". Proc Natl Acad Sci U S A. Nov. 11, 1997;94(23):12297-302.

Kurz, M et al. "An efficient synthetic strategy for the preparation of nucleic acid-encoded peptide and protein libraries for in vitro evolution protocols" Fourth International Electronic Conference on Synthetic Organic Chemistry (ECSOC-4), www.mdpi.org/ecsoc-4.htm, Sep. 1-30, 2000.

Kurz, M et al. Psoralen photo-crosslinked mRNA-puromycin conjugates: a novel template for the rapid and facile preparation of mRNA-protein fusions. Nucleic Acids Res. Sep. 15, 2000;28(18):E83.

Keiler et al. "Role of a peptide tagging system in degradation of proteins synthesized from damaged messenger RNA". Science. Feb. 16, 1996;271(5251):990-3.

Benner, SA. "Expanding the genetic lexicon: incorporating nonstandard amino acids into proteins by ribosome-based synthesis". Trends Biotechnol. May 1994;12(5):158-63.

Mendel, D."Site-directed mutagenesis with an expanded genetic code". Annu. Rev. Biophys. Biomol. Struc. 1995. 24:463-93.

Liu DR et al. "Engineering a tRNA and aminoacyl-tRNA synthetase for the site-specific incorporation of unnatural amino acids into proteins in vivo", Proc Natl Acad Sci U S A. Sep. 16, 1997;94(19):10092-7.

Liu DR et al. "Progress toward the evolution of an organism with an expanded genetic code". Proc Natl Acad Sci USA. Apr. 27, 1999;96(9):4780-5.

Liu, R et al. "Optimized synthesis of RNA-protein fusions for in vitro protein selection". Methods Enzymol. 2000;318:268-93.

Wang, L et al. "A new functional suppressor tRNA/aminoacyl-tRNA synthetase pair for the in vivo incorporation of unnatural amino acids into proteins" J. Am. Chem. Soc 2000, 122, 5010-5011 Pub Apr. 5, 2000.

Ellman J.A., et al. "Biosynthetic method for introducing Unnatural Amino acids site specifically into proteins". Methods Enzymol. 202, 301-336 (1992).

José Salas et al. "Biosynthetic Polydeoxynucleotides as Direct Templates for Polypeptide Synthesis". J. of Biological Chemistry, vol. 243, No. 6, 1968, p. 1012-1015.

Walder JA, Walder RY, Heller MJ, Freier SM, Letsinger RL, Klotz IM. "Complementary carrier peptide synthesis: general strategy and implications for prebiotic origin of peptide synthesis". Proc Natl Acad Sci U S A. Jan. 1979;76(1):51-5.

Bruick et al. "Template-directed ligation of peptides to oligonucleotides" Chemistry and Biology, vol. 3, No. 1, Jan. 1996, p. 49-56.

Tamura K, Schimmel P. "Oligonucleotide-directed peptide synthesis in a ribosome- and ribozyme-free system". Proc Natl Acad Sci U S A. Feb. 13, 2001;98(4):1393-7.

Lewis RJ, Hanawalt PC. "Ligation of oligonucleotides by pyrimidine dimers—a missing 'link' in the origin of life?"22,298(5872):393-6.

Liu J, Taylor JS. "Template-directed photoligation of oligodeoxyribonucleotides via 4-thiothymidine". Nucleic Acids Res. Jul. 1, 1998;26(13):3300-4.

Fujimoto et al. "Template-directed photoreversible ligation of deoxyoligonucleotides via 5-Vinyldeoxyuridine" J. Am. Soc. 2000, 122, 5646-5647.

Kenzo Fujimoto, Shigeo Matsuda, Naoki Ogawa, Masayuki Hayashi & Isao Saito "Template-directed reversible photocircularization of DNA via 5-vinyldeoxycytidine". Tetrahedron Letters 2000 , 41:33:6451-6454.

Kenzo Fujimoto, Naoki Ogawa, Masayuki Hayashi, Shigeo Matsuda & Isao Saito "Template directed photochemical synthesis of branched oligodeoxynucleotides via 5-carboxyvinyldeoxyuridine". Tetrahedron letters 2000, 41:49:9437-40.

Letsinger et al. "Chemical Ligation of oligonucleotides in the presence and absence of a template". J. Amer. Chem. Soc. 1993, 115, 3808-9.

Gryaznov SM, Letsinger RL. "Template controlled coupling and recombination of oligonucleotide blocks containing thiophosphoryl groups". Nucleic Acids Res. Mar. 25, 1993;21 (6):1403-8.

Gryaznov SM, Schultz R, Chaturvedi SK, Letsinger RL. "Enhancement of selectivity in recognition of nucleic acids via chemical autoligation". Nucleic Acids Res. Jun. 25, 1994;22(12):2366-9.

Herrlein MK, Letsinger RL. "Selective chemical autoligation on a double-stranded DNA template". Nucleic Acids Res. Nov. 25, 1994;22(23):5076-8.

Letsinger, RL; Wu, T; Elghanian, R "Chemical and photochemical ligation of oligonucleotide blocks". Nucleosides and nucleotides, 16(5&6), 643-652 (1997).

Visscher J, Schwartz AW "Template-directed synthesis of acyclic oligonucleotide analogues". J Mol Evol. Dec. 1988-Feb. 1989;28(1-2):3-6.

Visscher J, Bakker CG, van der Woerd R, Schwartz AW "Template-directed oligomerization catalyzed by a polynucleotide analog". Science. Apr. 21, 1989;244(4902):329-31.

Visscher J, van der Woerd R, Bakker CG, Schwartz AW. "Oligomerization of deoxynucleoside-bisphosphate dimers: template and linkage specificity". Orig Life Evol Biosph. 1989;19(1):3-6.

Zhan, ZJ and Lynn, DG "Chemical Amplification through template-directed synthesis". J. Am. Chem. Soc. 1997, 119, 12420-1.

Bruick RK, Koppitz M, Joyce GF, Orgel LE. "A simple procedure for constructing 5'-amino-terminated oligodeoxynucleotides in aqueous solution Nucleic Acids Res". Mar. 15, 1997;25(6):1309-10.

Albagli, D; Atta, RVA; Cheng, P; Huan, B and Wood, ML. "Chemical amplification (CHAMP) by a continuous, self-replicating oligonucleotide-based system" J. Am. Chem. Soc. 1999, 121, 6954-6955. Pub. on the web Jul. 14, 1999.

Xu, Y and Kool, E "Rapid and Selective selenium-mediated autoligation of DNA strands" J. Am. Chem. Soc. 2000, 122, 9040-1 Pub. on web Aug. 31, 2000.

Xu Y, Karalkar NB, Kool ET. "Nonenzymatic autoligation in direct three-color detection of RNA and DNA point mutations". Nat Biotechnol. Feb. 2001;19(2):148-52.

Li X, Zhan ZY, Knipe R, Lynn DG. "DNA-catalyzed polymerization". J Am Chem Soc. Feb. 6, 2002;124(5):746-7.

Czlapinski, JL and Sheppard, TL. "Nucleic acid template-directed assembly of metallosalen-DNA conjugates". J Am Chem Soc. Sep. 5, 2001;123(35):8618-9 published on the web Aug. 10, 2001.

Leitzel JC, Lynn DG "Template-directed ligation: from DNA towards different versatile templates". Chem Rec. 2001;1(1):53-62. Published online Jan. 30, 2001.

Schmidt JG, Nielsen PE, Orgel LE. "Information transfer from DNA to peptide nucleic acids by template-directed syntheses". Nucleic Acids Res. Dec. 1, 1997;25(23):4792-4796.

Dower, WJ et al. "In vitro selection as a powerful tool for the applied evolution of proteins and peptides".Current Opinion in Chemical Biology, 2002, 6:390-398.

Brenner, S and Lerner, RA . "Encoded combinatorial chemistry" Proc. Natl. Acad. Sci. USA. vol. 89, p. 5381-3, Jun. 1992.

Gartner, Z; Liu, DR "The generality of DNA-templated synthesis as a basis for evolving non-natural small molecules". J Am Chem Soc. Jul. 18, 2001:123(28):6961-3.

David Liu. "Expanding the reaction scope of DNA-templated synthesis Angew". Chem. Int. Ed. 2002, 41, No. 10 pp. 1796-1800. Published May 15, 2002.

Gartner, ZJ et al. "Multistep small-molecule synthesis programmed by DNA templates". J. Am. Chem. Soc. vol. 124, No. 35, 2002, 10304-10306.

Calderone, CT et al. "Directing otherwise incompatible reactions in a single solution by using DNA-templated organic synthesis". Angew Chem Int Ed, 2002, 41, No. 21. 4104-4108.

Bittker, JA; Phillips, KJ and Liu, DR "Recent advances in the in vitro evolution of nucleic acids". Curr Opin Chem Biol. Jun. 2002;6(3):367-74. Review. Pub. on the web Mar. 20, 2002.

Summerer,D and Marx, A "DNA-templated synthesis: more versatile than expected". Angew Chem Int Ed Engl. Jan. 4, 2002;41(1):89-90. Review.

Gartner, ZJ et al. "Two enabling architectures for DNA-templated organic synthesis". Angew. Chem Int. Ed. 2003, 42, No. 12, 1370-1375.

Rosenbaum, DM et al. "Efficient and sequence-specific DNA-templated polymerization of peptide nucleic acid aldehydes". J. Am. Chem. Soc. vol. 125, No. 46, 2003, 13924-13925.

Li, X et al. "Stereoselectivity in DNA-templated organic synthesis and its origins". J. Am. Chem. Soc. vol. 125, No. 34, 2003, 10188-10189.

Gordon, EM et al. "Applications of combinatorial technologies to drug discovery. 2. Combinatorial organic synthesis, library screening strategies, and future directions". Journal of Medicinal Chemistry, vol. 37, No. 10, May 13, 1994.

Otto, S et al. S"Recent developments in dynamic combinatorial chemistry". Current opinion in Chemical Biology 2002, 6: 321-327.

Pavia, MR. "The Chemical generation of molecular diversity". http://www.netsci.org/Science/Combichem/feature01.html.

Braun, E, et al. "DNA-templated assembly and electrode attachment of a conducting silver wire". Nature, vol. 391, Feb. 19, 1998, 775-778.

Tanaka, K et al. "Synthesis of a novel nucleoside for alternative DNA base pairing through metal complexation" J. Org. Chem. 1999, 64, 5002-5003.

Beger, M et al. "Universal bases for hybridization, replication and chain termination", Nucleic acids research, Oxford University Press, vol. 28, No. 15, pub. 1 Aug. 2000, p. 2911-2914.

Weizman, H et al. "2,2'-Bipyridine ligandoside: a novel building block for modifying DNA with intra-duplex metal complexes". J. Am. Chem. Soc. 2001, 123, 3375-3376.

Frutos, AG et al. "Demonstration of a word design strategy for DNA computing on surfaces". Nucleic Acids Research, 1997, vol. 25, No. 23, 4748-4757.

Loweth, CJ et al. "DNA-based assembly of gold nanocrystals". Angew. Chem. Int. Ed. 1999, 38, No. 12. 1808-1812.

Elghanian, R et al. "Selective colorimetric detection of polynucleotides based on the distance-dependent optical properties of gold nanoparticles". Science, vol. 277, Aug. 22, 1997.

Storhoff, JJ and Mirkin, CA. "Programmed Materials Synthesis with DNA". Chem Rev. Jul. 14, 1999;99(7):1849-1862.

Mirkin CA. "Programming the assembly of two- and three-dimensional architectures with DNA and nanoscale inorganic building blocks". Inorg Chem. May 29, 2000;39(11):2258-72.

Waybright SM, Singleton CP, Wachter K, Murphy CJ, Bunz UH. "Oligonucleotide-directed assembly of materials: defined oligomers". J Am Chem Soc. Mar. 7, 2001;123(9)1828-33. Pub. on web Feb. 7, 2001.

Bruce Smith and Markus Krummenacker "DNA-guided assembly of proteins as a pathway to an assembler", (http://www.wadsworth.org/albcon97/abstract/krummena.htm): 1997 Albany Conference: Biomolecular Motors and Nanomachines.

DeWitt, SH et al. "Diversomers": an approach to nonpeptide, nonoligomeric chemical diversity. Proc. Natl. Acad. Sci, USA, vol. 90, pp. 6909-6913, Aug. 1993.

Nielsen, J et al. "Synthetic methods for the implementation of encoded combinatorial chemistry". J. Am. Chem. Soc. 1993, 115, 9812-9813.

Ohlmeyer, MHJ et al. "Complex synthetic chemical libraries indexed with molecular tags". Proc. Natl. Acad, Sci, USA, vol. 90, pp. 10922-10926, Dec. 1993, Chemistry.

Zuckermann, RN et al. "Discovery of nanomolar ligands for 7-transmembrane G-protein-coupled receptors from a diverse N-(substituted) glycine peptoid library". J. Med. Chem. 1994, 37, 2678-2685.

Luo, P. et al. "Analysis of the structure and stability of a backbone-modified oligonucleotide: implications for avoiding product inhibition in catalytic template-directed synthesis". J. Am. Chem. Soc. 1998, 120, 3019-3031.

Luther, A et al. "Surface-promoted replication and exponential amplification of DNA analogues", Nature, vol. 396, Nov. 19, 1998, 245-248.

Klekota, B et al. "Selection of DNA-Binding Compounds via Multistage Molecular Evolution". Tetrahedron 55 (1999) 11687-11697.

Furlan, RLE et al. "Molecular amplification in a dynamic combinatorial library using non-covalent interactions". Chem. Commun., 2000, 1761-1762.

Ramström, O et al. "In situ generation and screening of a dynamic combinatorial carbohydrate library against concanavalin A". ChemBioChem, 2000, 1, 41-48.

Cousins, GRL et al. "Identification and Isolation of a Receptor for N-Methyl Alkylammonium Salts: Molecular Amplification in a Pseudo-peptide Dynamic Combinatorial Library". Angew. Chem. Int. Ed., 2001, 40, No. 2, 423-427.

Roberts, SI et al. "Simultaneous selection, amplification and isolation of a pseudo-peptide receptor by an immobilised N-methyl ammonium ion template". Chem. Commun., 2002, 938-939.

Doyon, J.B et al. "Highly sensitive in vitro selections for DNA-linked synthetic small molecules with protein binding affinity and specificity" J. Am. Chem. Soc, Sep. 16, 2003.

Kanan, M.W et al. "Reaction discovery enabled by DNA-templated synthesis and in vitro selection" Nature, vol. 431, Sep. 30, 2004.

"Finding reactions in a haystack: Try'em all, see what works" Meeting American Chemical Society, Sep. 10, 2004, vol. 305, Science.

"The Nucleus", Jan. 2004, vol. LXXXII, No. 5, R. Grubina; "Summer Research Report: R. Grubina on DNA Templated Synthesis for Small Molecule Library", p. 10-14.

Nazarenko et al., "A closed tube format for amplification and detection of DNA based on energy transfer", Nucleic Acids Research, 1997, vol. 25, No. 12, p. 2516-2521.

Chan et al., "Intra-tRNA distance measurements for nucleocapsid protein-dependent tRNA unwinding during priming of HIV reverse transcription", PNAS vol. 96, p. 459-464, Jan. 1999.

Liu DR et al., DNA-templated synthesis as a basis for the evolution of synthetic molecules, Abstracts of Papers of the American Chemical Society; 225: 612-ORGN , Part 2, Mar. 2003.

Rodriguez et al., "Template-directed extension of a guanosine 5'-phosphate covalently attached to an oligodeoxycytidylate template", J Mol Evol (1991) 33:477-482.

Acevedo et al., "Template-directed oligonucleotide ligation on hydroxylapatite", Nature vol. 321, Jun. 19, 1986, p. 790-792.

Piccirilli, "RNA seeks its maker", Nature vol. 376, Aug. 17, 1995, p. 548.

A. W. Schwartz et al., "Template-directed synthesis of novel, nucleic acid-like structures", Science 1985, 228, 585-7.

Halpin et al.: DNA display III. Solid-phase organic synthesis on unprotected DNA. PLoS Biol. Jul. 2004;2(7):E175. Epub Jun. 22, 2004.

Halpin et al.: DNA display II. Genetic manipulation of combinatorial chemistry libraries for small-molecule evolution. PLoS Biol. Jul. 2004;2(7):E174. Epub Jun. 22, 2004.

Halpin et al.: DNA display I. Sequence-encoded routing of DNA populations. PLoS Biol. Jul. 2004;2(7):E173. Epub Jun. 22, 2004.

"Highly Sensitive In Vitro Selections for DNA-Linked Synthetic Small Molecules with Protein Binding Affinity and Specificity" Doyon, J. B.; Snyder, T. M.; Liu, D. R. J. Am. Chem. Soc. 125, 12372-12373 (2003).

"Translation of DNA into Synthetic N-Acyloxazolidines" Li, X.; Gartner, Z. J.; Tse, B. N.; Liu, D. R. J. Am. Chem. Soc. 126, 5090-5092 (2004).

"DNA-Templated Organic Synthesis: Nature's Strategy for Controlling Chemical Reactivity Applied to Synthetic Molecules" Li, X.; Liu, D. R. Angew. Chem. Int. Ed. 43, 4848-4870 (2004).

"DNA-Templated Organic Synthesis and Selection of a Library of Macrocycles" Gartner, Z. J.; Tse, B. N.; Grubina, R.; Doyon, J. B.; Snyder, T. M.; Liu, D. R. Science 305, 1601-1605 (2004).

"Nucleic Acid-Templated Synthesis as a Model System for Ancient Translation" Calderone, C. T. and Liu, D. R. Curr. Opin. Chem. Biol. 8, 645-653 (2004).

"DNA-Templated Functional Group Transformations Enable Sequence-Programmed Synthesis Using Small-Molecule Reagents" Sakurai, K.; Snyder, T. M.; Liu, D. R. J. Am. Chem. Soc. 127, 1660-1661 (2005).

"Translating DNA into synthetic Molecules", David R. Liu, PLoS Biology, Jul. 2004, vol. 2, Iss. 7, p. 905-6.

"The Development of Amplifiable and Evolvable Unnatural Molecules", David R. Liu, Harvard Univ. Cambridge MA Dept of Chemistry and Chemical Biology, Report dated Aug. 4, 2003 No. A104614, approved for public release.

Website of Prof. David R. Liu, publicly available Mar. 11, 2000.
Website of Prof. David R. Liu, publicly available Oct. 15, 2000.
Website of Prof. David R. Liu, publicly available Mar. 1, 2001.
Website of Prof. David R. Liu, publicly available Apr. 19, 2001.
Website of Prof. David R. Liu, publicly available Sep. 23, 2001.
Website of Prof. David R. Liu, publicly available Sep. 24, 2002.
Website of Prof. David R. Liu, publicly available Nov. 20, 2002.
Website of Prof. David R. Liu, publicly available Oct. 15, 2003.

Inoue et al, Oligomerization of (Guanosine 5'-phosphor)-2-methylimidazolide on Poly(C), J. Mol. Biol. (1982), 162, 201-217.

C. B. Chen et al., "Template-directed synthesis on Oligodeoxycytidylate and Polydeoxycytidylate templates" J. Mol. Biol. 1985, 181, 271.

H. Rembold et al., "Single-strand regions of Poly(G) act as templates for oligo(C) synthesis" J. Mol. Evol. 1994, 38, 205.

T. Inoue et al., "A nonenzymatic RNA polymerase model", Science 1983, 219, p. 859-862.

O. L. Acevedo et al., "Non-enzymatic transcription of an oligonucleotide 14 residues long", J. Mol. Biol. 1987, 197, p. 187-193.

C. Böhler et al., "Template switching between PNA and RNA oligonucleotides", Nature 1995, 376, 578-581.

*Primary Examiner*—Young J Kim
*Assistant Examiner*—Samuel C Woolwine
(74) *Attorney, Agent, or Firm*—Iver P. Cooper

(57) ABSTRACT

The present invention in one aspect relates to a method for synthesizing a bifunctional complex comprising a molecule and an identifier polynucleotide identifying at least some of the chemical entities which have participated in the synthesis of the molecule in accordance with the methods of the present invention. The invention also relates to a library of different bifunctional complexes. The library of the invention can be used e.g. for identifying drug leads. Furthermore, the present invention is based on the principle that chemical entities initially provided on a building block oligonucleotide (i.e. a building block having an oligonucleotide part which is linked to a chemical entity) can be brought into reactive proximity without the use of a template comprising a set of covalently linked codons. Also, the present invention allows reaction of chemical entities when the chemical entities are linked to a single stranded identifier polynucleotide obtained by covalently linking the oligonucleotide parts (oligonucleotide identifiers) of the building blocks. The single stranded identifier polynucleotides differs from template directed synthesis methods employing codon and anti-codon hybridisation between a template and one or more transfer units, i.e. methods wherein e.g. reactive units on transfer units are reacted while the anti-codon of the transfer units are hybridised to template codons.

27 Claims, 35 Drawing Sheets

Figure 1A:
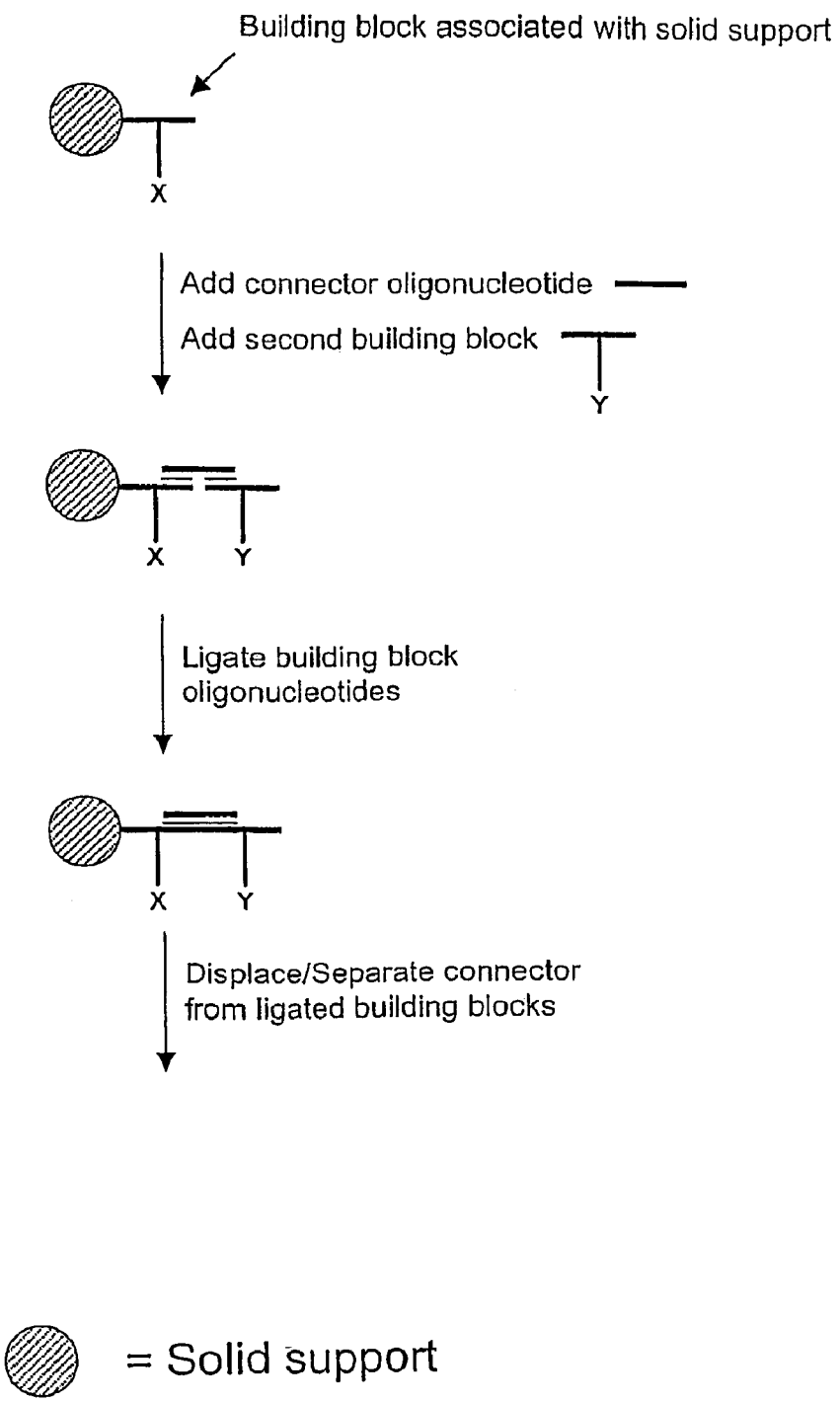

Figure 1B
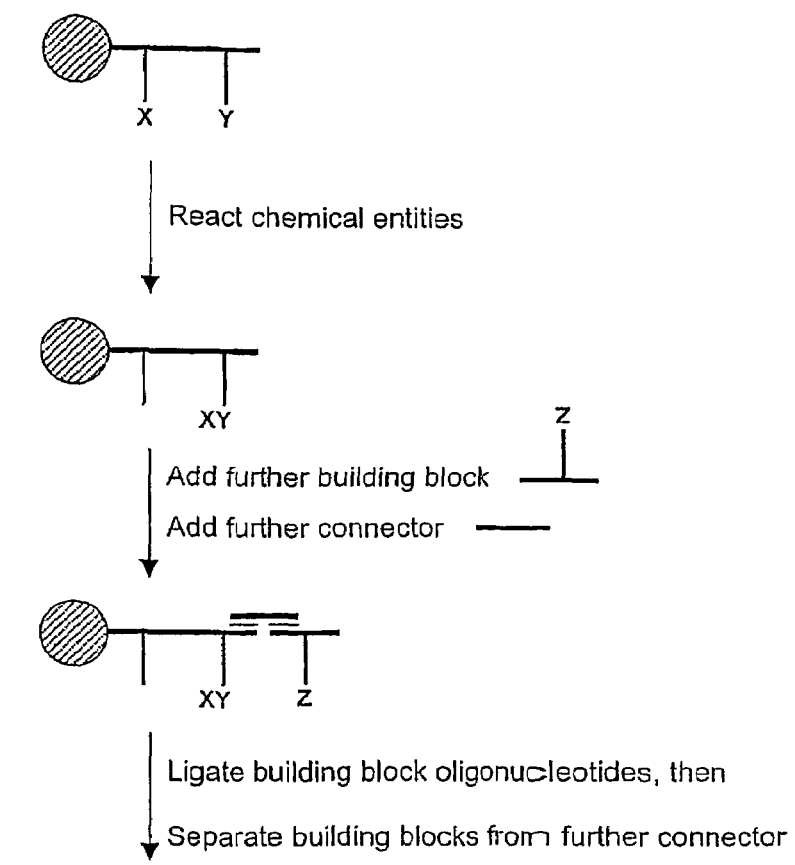
 = Solid support

= Solid support

Figure 2A:
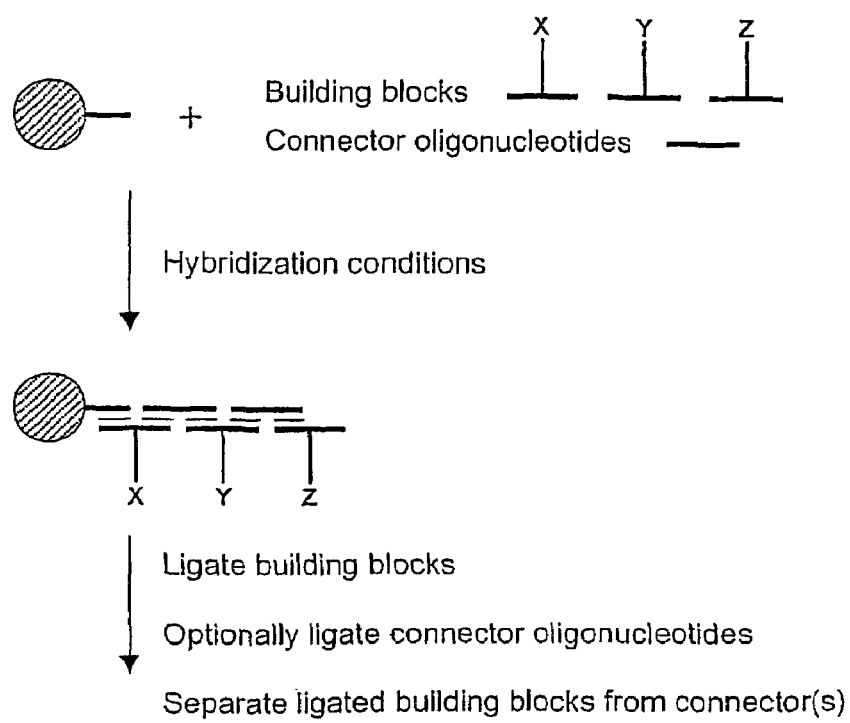

Figure 2B
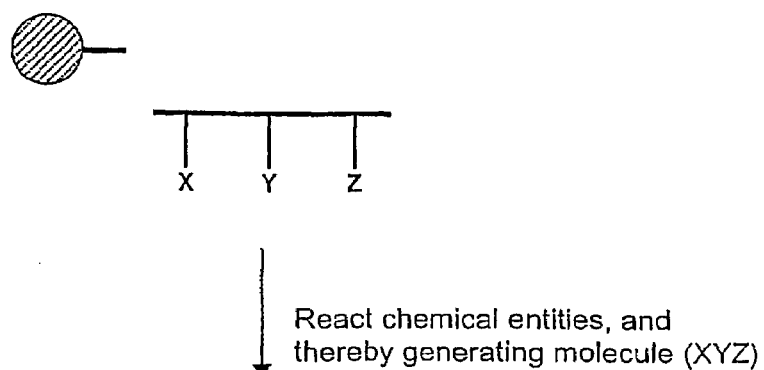
React chemical entities, and thereby generating molecule (XYZ)
 = Solid support

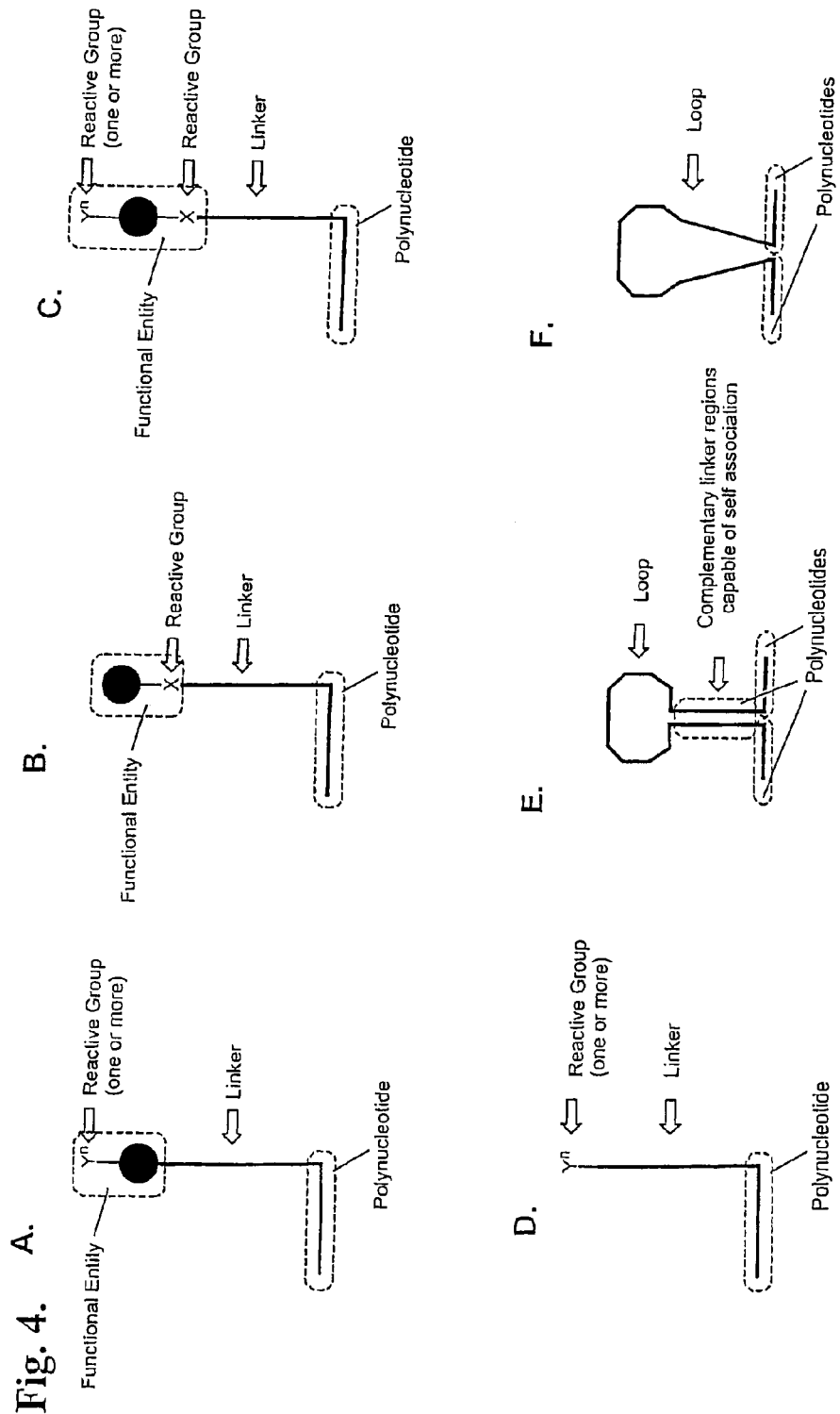

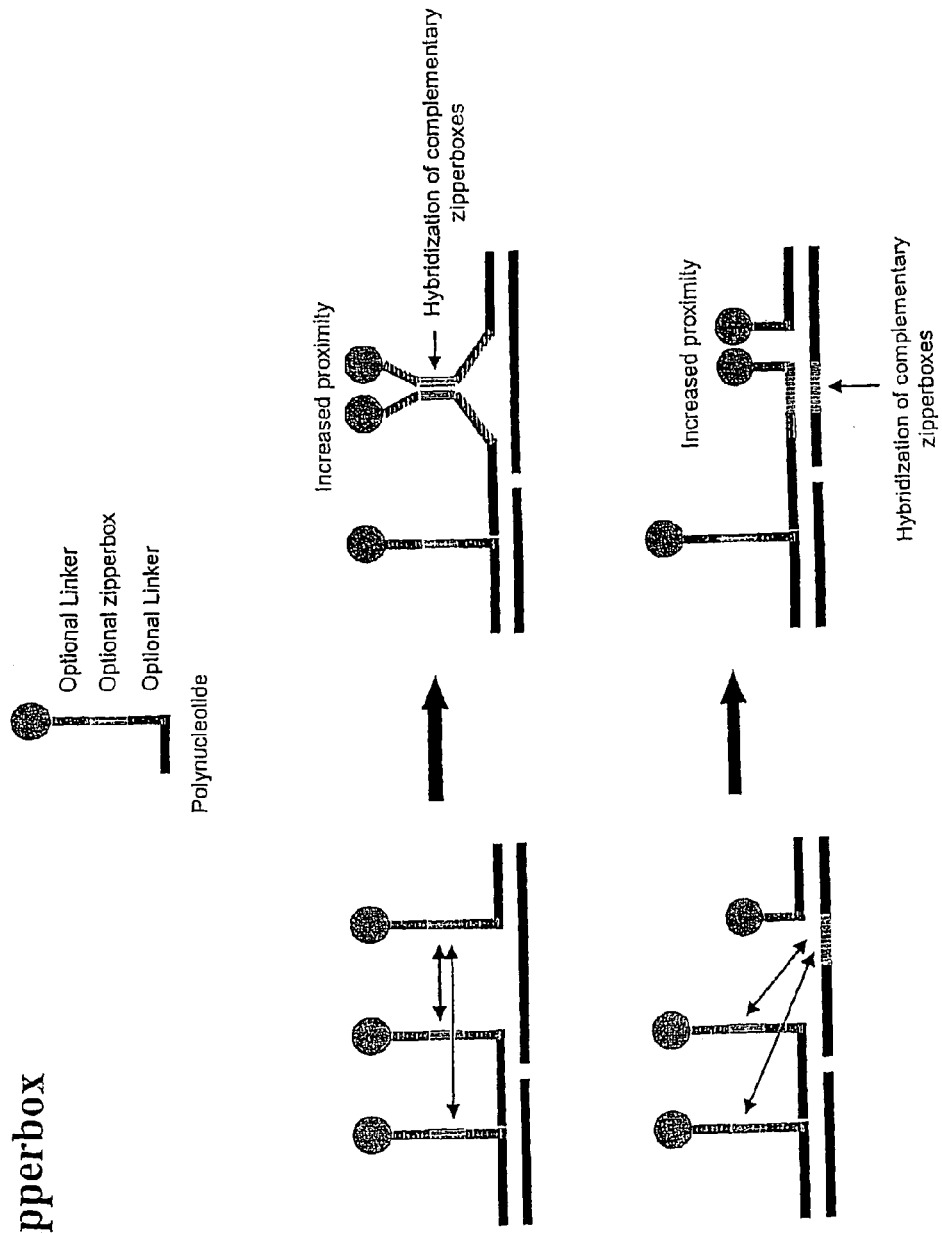

Fig. 6. Reaction types allowing simultaneous reaction and linker cleavage.
Nucleophilic substitution using activation of electrophiles
FIG. 6A. Acylating monomer building blocks - principle
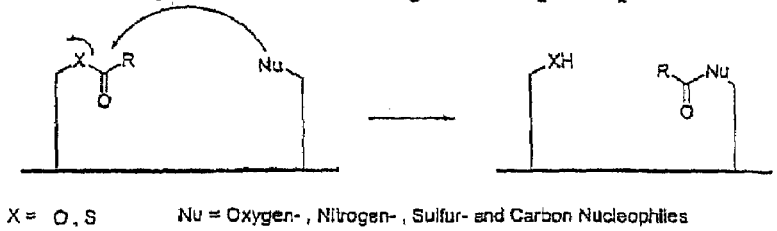
X = O, S    Nu = Oxygen-, Nitrogen-, Sulfur- and Carbon Nucleophiles
FIG. 6B. Acylation
Amide formation by reaction of amines with activated esters

FIG. 6C. Acylation
Pyrazolone formation by reaction of hydrazines with β-Ketoesters
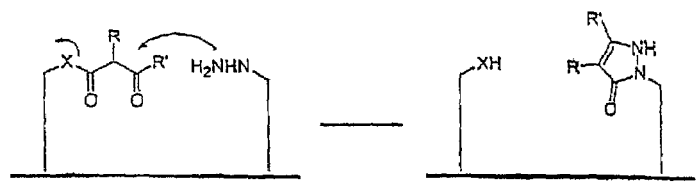
FIG. 6D. Acylation
Isoxazolone formation by reaction of hydroxylamines with β-Ketoesters
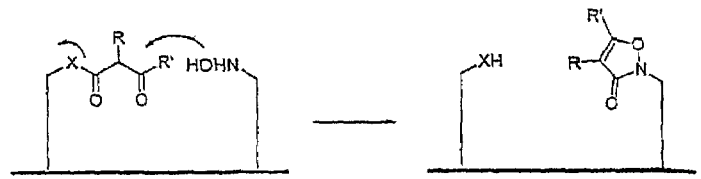
FIG. 6E. Acylation
Pyrimidine formation by reaction of thioureas with β-Ketoesters
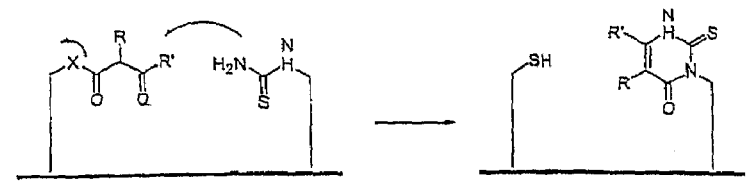

FIG. 6F. Acylation
Pyrimidine formation by reaction of ureas with Malonates
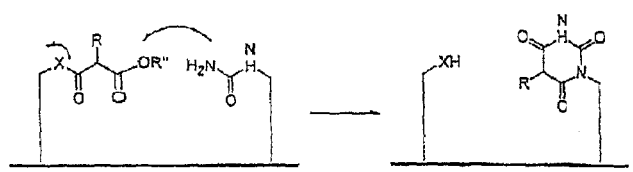
FIG. 6G. Acylation
Coumarine or quinolinon formation by a Heck reaction followed by a nucleophilic substitution
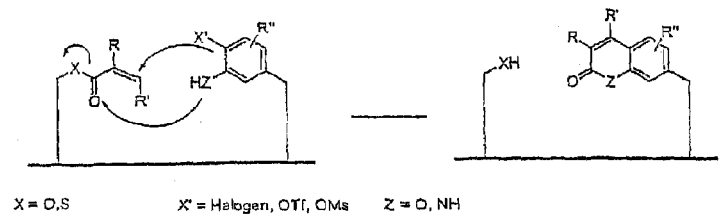
X = O,S    X' = Halogen, OTf, OMs    Z = O, NH FIG. 6H. Acylation
Phthalhydrazide formation by reaction of Hydrazines and Phthalimides
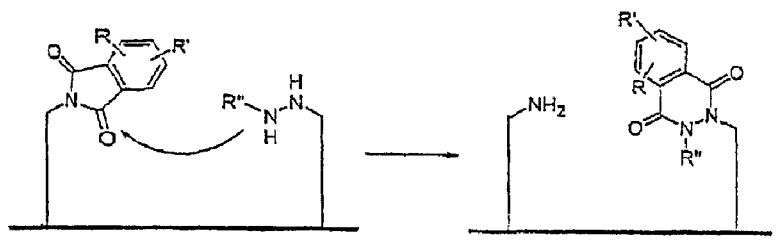
FIG. 6I. Acylation
Diketopiperazine formation by reaction of Amino Acid Esters
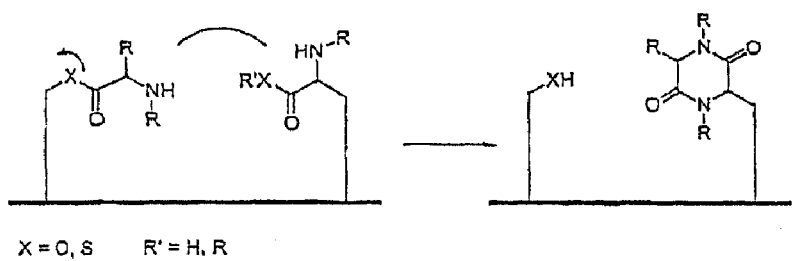
X = O, S    R' = H, R FIG. 6J. Acylation
Hydantoin formation by reaction of Urea and α-substituted Esters

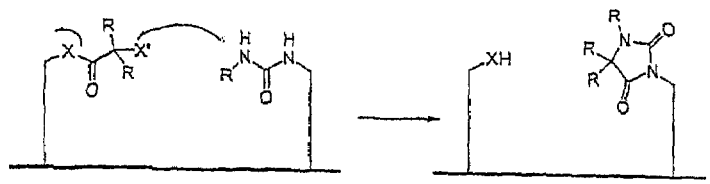

X = O, S    X' = Hal, OTos, OMs, etc.

FIG. 6K. Alkylating monomer building blocks - principle
Alkylated compounds by reaction of Sulfonates with Nucleofiles

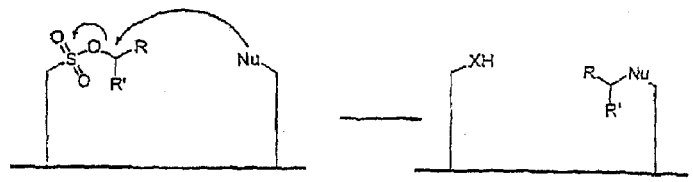

Nu = Oxygen-, Nitrogen-, Sulfur- and Carbon Nucleophiles

FIG. 6L. Vinylating monomer building blocks - principle

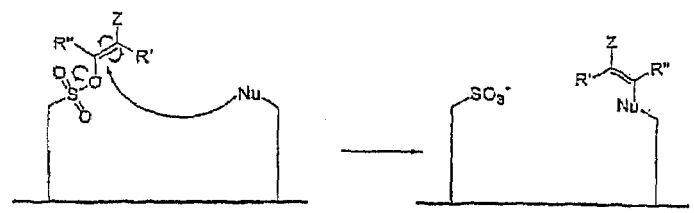

Z = CN, COOR, COR, $NO_2$, $SO_2R$, S(=O)R, $SO_2NR_2$, F
Nu = Oxygen-, Nitrogen-, Sulfur- and Carbon Nucleophiles FIG. 6M. Heteroatom electrophiles
Disulfide formation by reaction of Pyridyl disulfide with mercaptanes
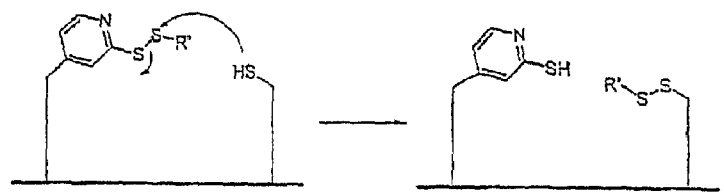

FIG. 6N. Acylation
Benzodiazepinone formation by reaction of Amino Acid Esters and Amino Ketones
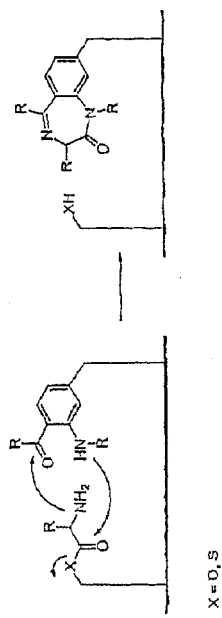
X = O, S
Addition to carbon-hetero multiple bonds
FIG. 6O. Wittig/Horner-Wittig-Emmons reagents
Substituted alkene formation by reaction of Phosphonates with Aldehydes or Ketones
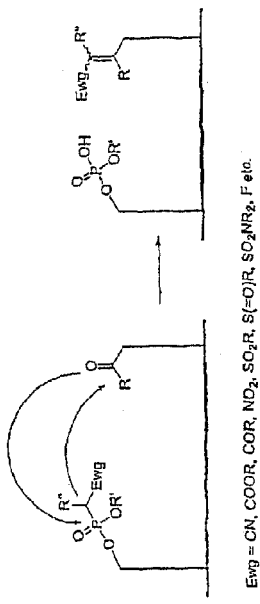
Ewg = CN, COOR, COR, NO₂, SO₂R, S(=O)R, SO₂NR₂, F etc.

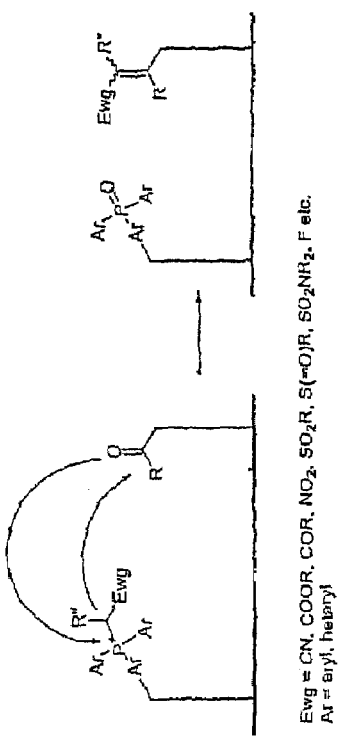
FIG. 6P. Wittig/Horner-Wittig-Emmons reagents
Substituted alkene formation by reaction of Phosphonates with Aldehydes or Ketones Transition metal catalysed reactions FIG. 6Q. Transition metal cat. Arylations

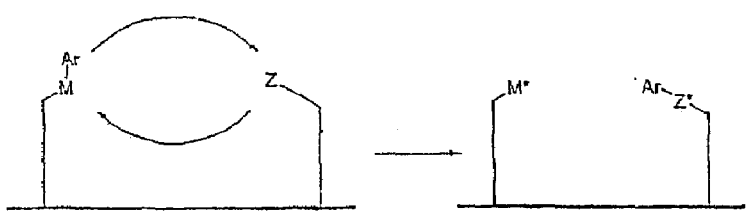

Z = haloaryl, halohetaryl, ArOMs, ArOTf, ArOTos or NHR or OH or SH etc.
Z* = Aryl, hetaryl, NR or O or S etc
M = e.g. BR, BR$_2^-$, SnR$_2$ etc.
R = H, alkyl, aryl, hetaryl, OR, NR$_2$
M* = a.g. B(OH)R, B(OH)R$_2^-$, Sn(OH)R$_2$ etc.

FIG. 6R. Arylation
Biaryl formation by the reaction of Borates with Aryls or Heteroaryls

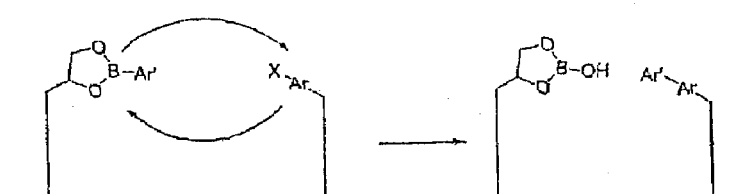

X = Halogen, OMs, OTf, OTos, etc

FIG. 6S. Arylation
Biaryl formation by the reaction of Boronates with Aryls or Heteroaryls
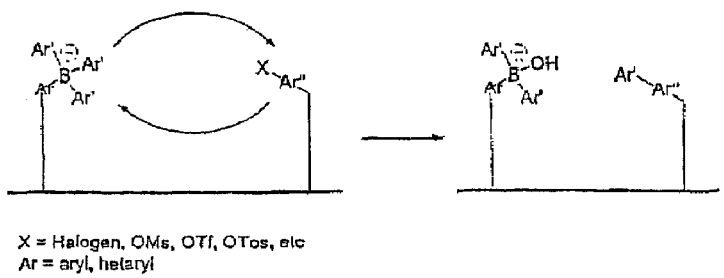
X = Halogen, OMs, OTf, OTos, etc
Ar = aryl, hetaryl
FIG. 6T. Arylation
Biaryl formation by the reaction of Boronates with Aryls or Heteroaryls
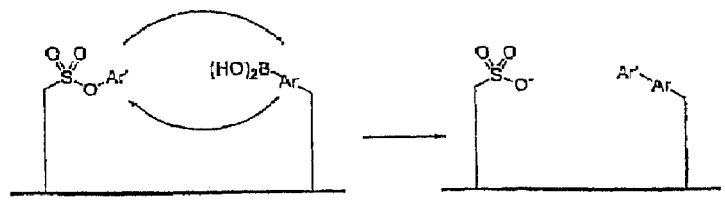

FIG. 6U. Arylation
Arylamine formation by the reaction of amines with activated Aryls or Heteroaryls
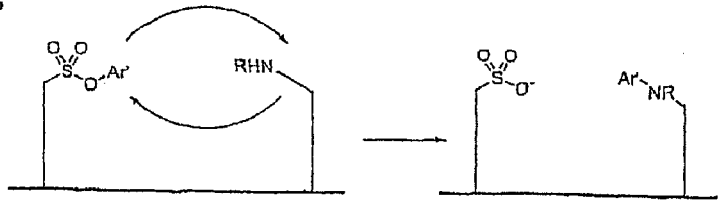
FIG. 6V. Arylation
Arylamine formation by the reaction of amines with hypervalent iodonium salts
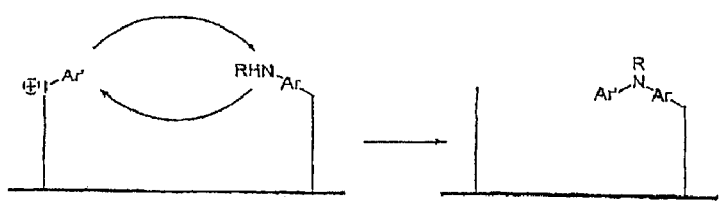
FIG. 6X. Arylation
Vinylarene formation by the reaction of alkenes with Aryls or Heteroaryls
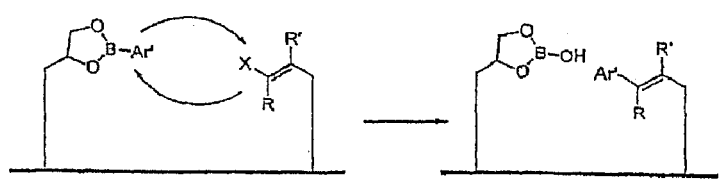
X = Halogen, OMs, OTf, OTos, etc

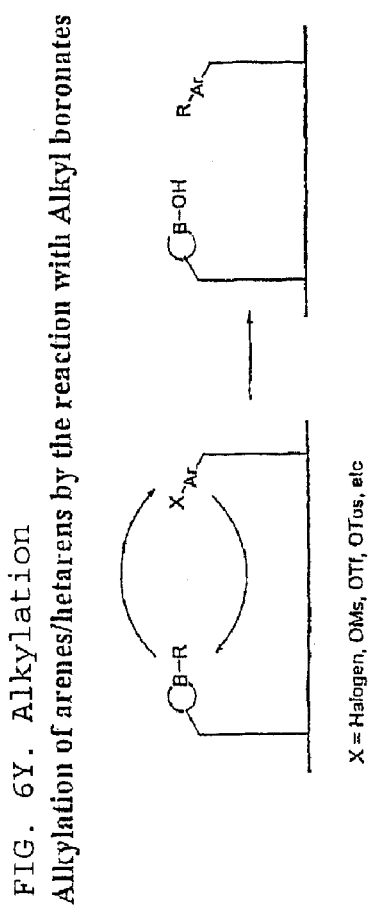
FIG. 6Y. Alkylation
Alkylation of arenes/hetarens by the reaction with Alkyl boronates FIG. 6Z. Alkylation
Alkylation of arenes/hetarenes by reaction with enolethers
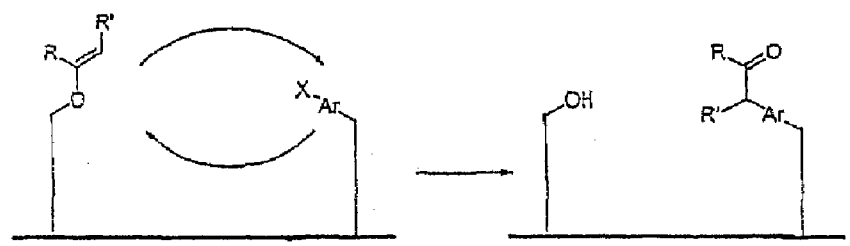
X = Halogen, OMs, OTf, OTos, etc Nucleophilic substitution using activation of nucleophiles
FIG. 6AA. Condensations
Alkylation of aldehydes with enolethers or enamines
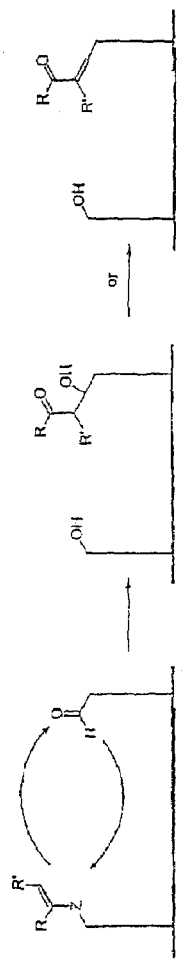
Z = NR, O; X = Halogen, OMs, OTf, OTos, etc
FIG. 6AB. Alkylation
Alkylation of aliphatic halides or tosylates with enolethers or enamines
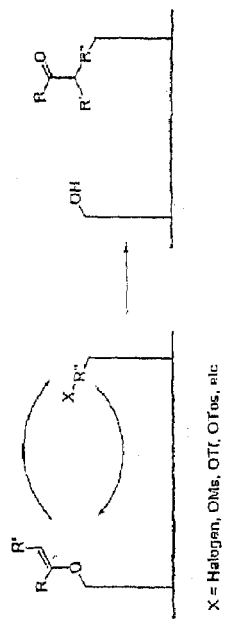
X = Halogen, OMs, OTf, OTos, etc Cycloadditions
FIG. 6AC. [2+4] Cycloadditions
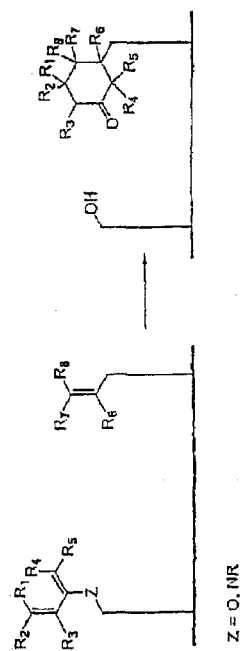
Z = O, NR
FIG. 6AD. [2+4] Cycloadditions
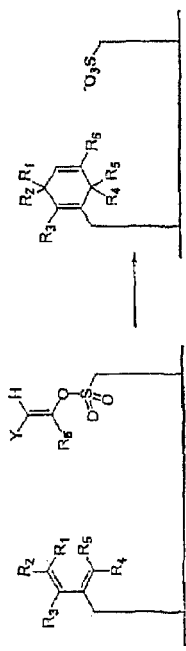
Y = CN, COOR, COR, NO₂, SO₂R, S(=O)R, SO₂NR₂, F

Figure 7B:
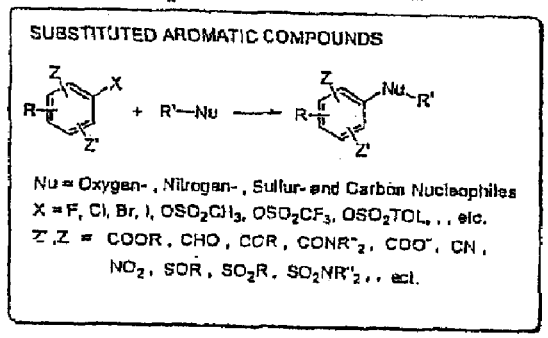

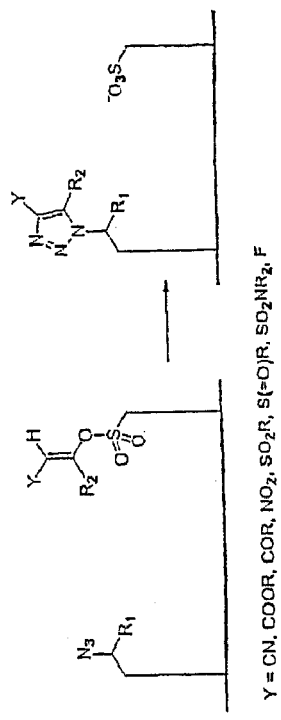
FIG. 6AE. [3+2] Cycloadditions
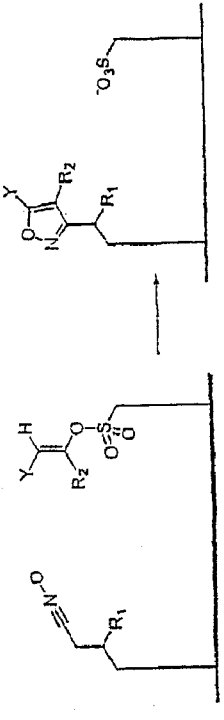
FIG. 6AF. [3+2] Cycloadditions FIG. 7A . Pairs of reactive groups X,Y and the resulting bond XY.

Nucleophilic substitution reactions

Aromatic nucleophilic substitution

Transition metal catalysed reactions

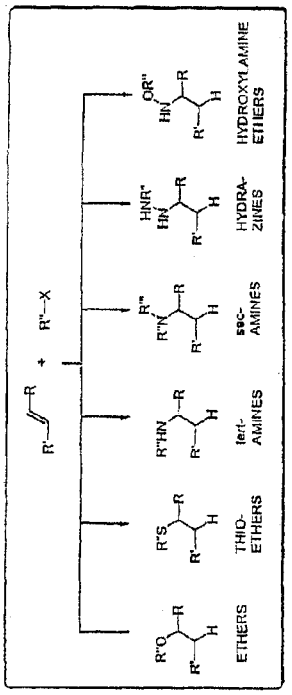
FIG. 7D Addition to carbon-carbon multiple bonds
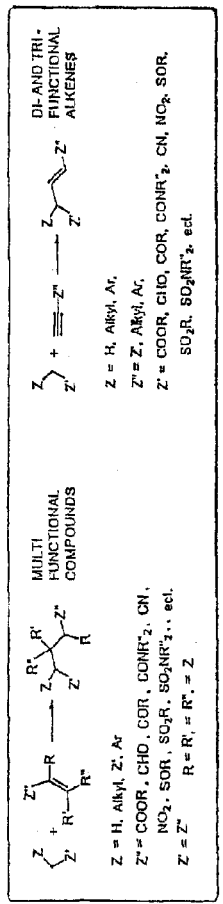
FIG. 7E

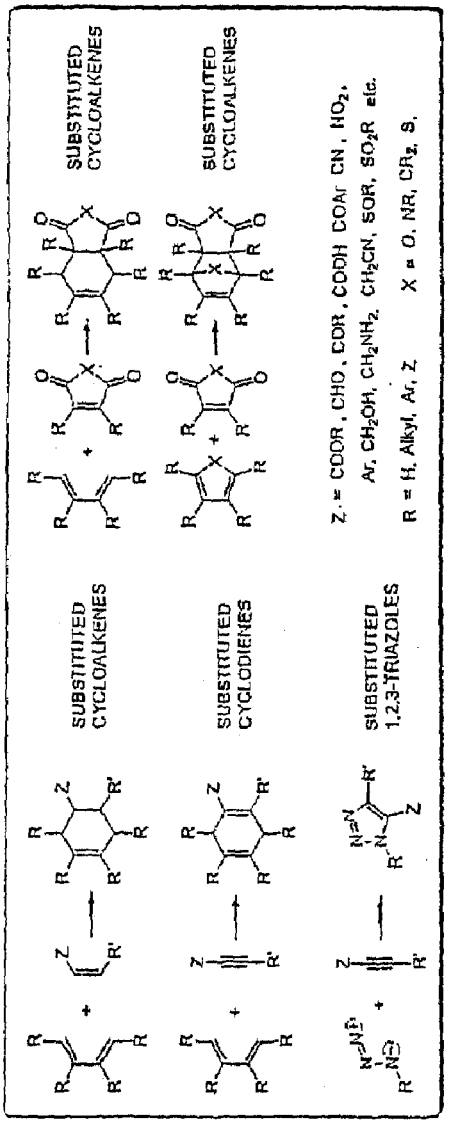
FIG. 7F Cycloaddition to multiple bonds

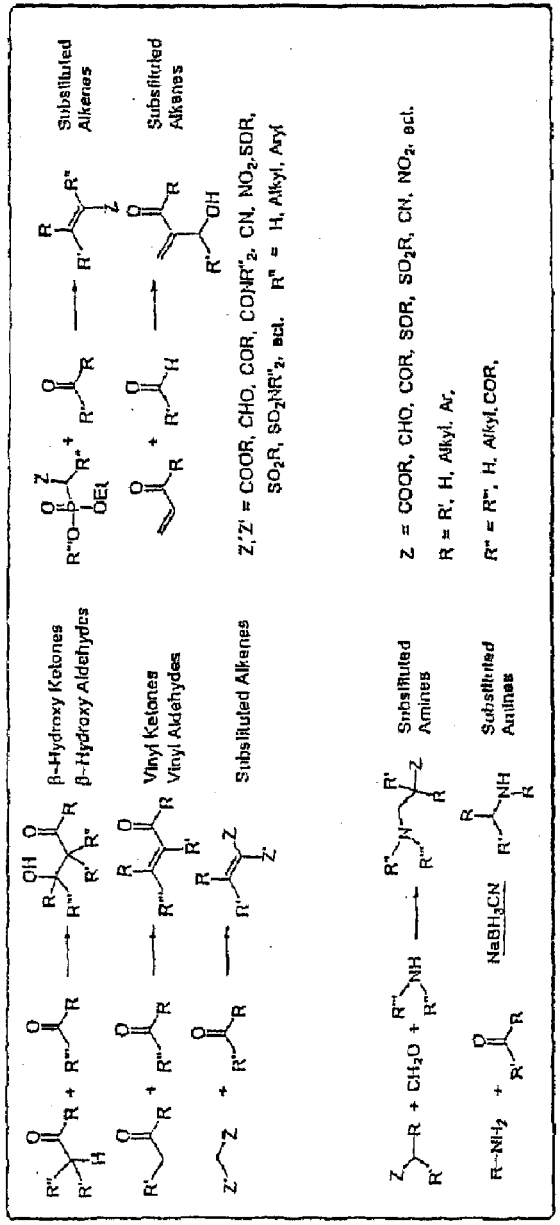
FIG. 7G Addition to carbon-hetero multiple bonds

Figure 8. Cleavable Linkers

FIG. 8A. Linker for the formation of Ketones, Aldehydes, Amides and Acids

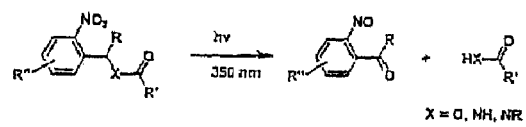

X = O, NH, NR

FIG. 8B. Linker for the formation of Ketones, Amides and Acids

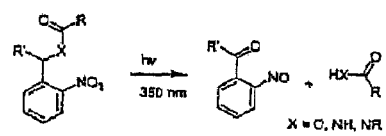

X = O, NH, NR

FIG. 8C. Linker for the formation of Aldehydes and Ketones

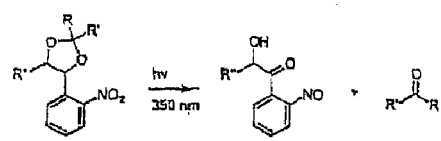

FIG. 8D. Linker for the formation of Alcohols and Acids

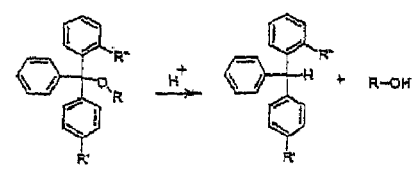

FIG. 8E. Linker for the formation of Amines and Alcohols

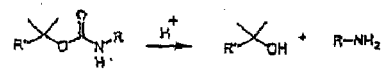

FIG. 8F. Linker for the formation of Esters, Thioesters, Amides and Alcohols

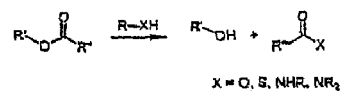

X = O, S, NHR, NR$_2$

FIG. 8G. Linker for the formation of Sulfonamides and Alcohols

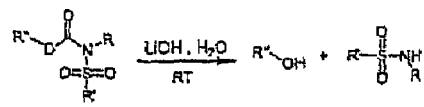

FIG. 8H. Linker for the formation of Ketones, Amines and Alcohols

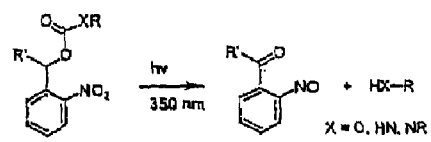

FIG. 8I. Linker for the formation of Ketones, Amines, Alcohols and Mercaptanes

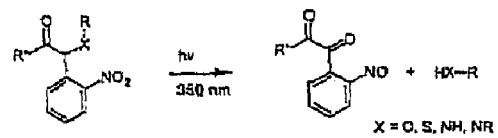

FIG. 8J. Linker for the formation of Biaryl and Bihetaryl

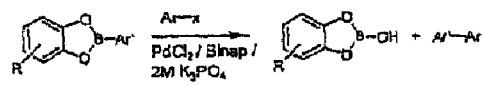

FIG. 8K. Linker for the formation of Benzyles, Amines, Anilins Alcohols and Phenoles

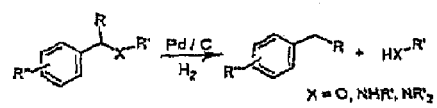

FIG. 8L. Linker for the formation of Mercaptanes

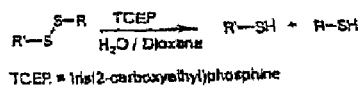

FIG. 8M. Linker for the formation of Glycosides
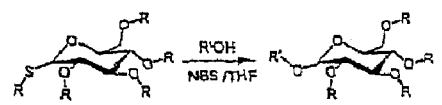
FIG. 8N. Linker for the formation of Aldehydes and Glyoxylamides
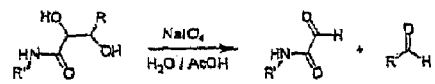
FIG. 8O. Linker for the formation of Aldehydes, Ketones and Aminoalcohols
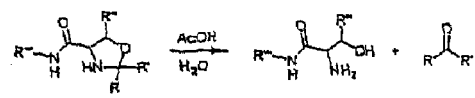

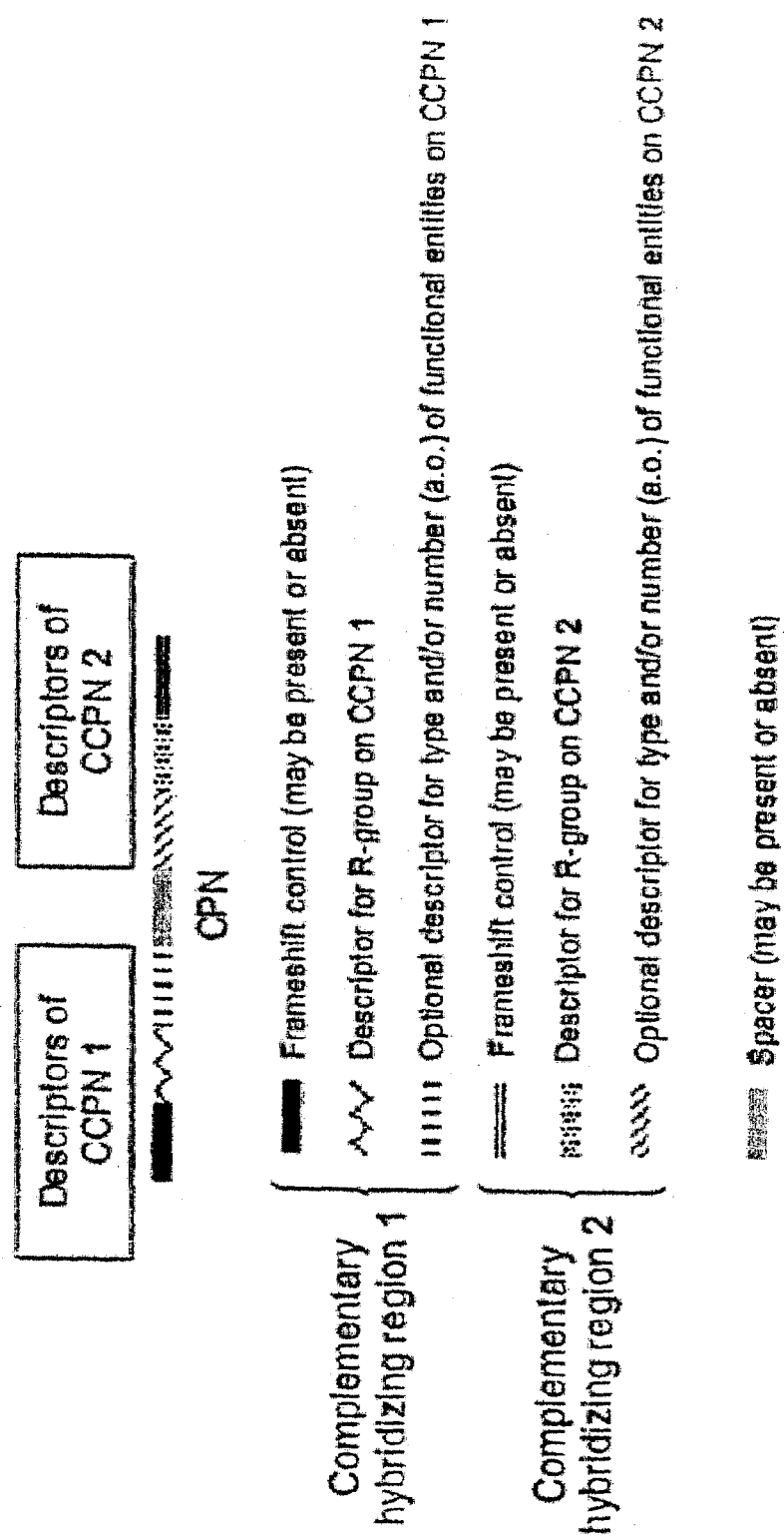

LIGATIONAL ENCODING USING BUILDING BLOCK OLIGONUCLEOTIDES

All patent and non-patent references cited in the application are hereby incorporated by reference in their entirety. This application is a non-provisional of U.S. provisional application Ser. No. 60/585,008 filed 6 Jul. 2004, which is hereby incorporated by reference in its entirety. This application is a continuation-in-part of application Serial No. PCT/DK2004/000195 filed 22 Mar. 2004, which is hereby incorporated by reference in its entirety.

TECHNICAL FIELD OF THE INVENTION

The present invention in one aspect relates to a method for synthesizing a bifunctional complex comprising a molecule and an identifier polynucleotide identifying at least some of the chemical entities which have participated in the synthesis of the molecule in accordance with the methods of the present invention. The invention also relates to a library of different bifunctional complexes. The library of the invention can be used e.g. for identifying drug leads.

BACKGROUND OF THE INVENTION

Libraries of complexes comprising an molecule as well as the template which has coded for the synthesis thereof have previously been disclosed. Attempts to form complexes comprising an molecule as well as a template coding for the chemical entities that have participated in the formation of the molecule have been based on split-and-mix methods known e.g. from combinatorial chemistry, see e.g. WO 93/06121 A1, EP 643 778 B1, and WO 00/23458.

If several selection rounds are desirable or necessary, the split-and-mix principle has the inherent disadvantage of requiring decoding between each selection round. The decoding step may be laborious and cumbersome because the templates usually are incorporated into a vector and then subsequently into a suitable host micro organism.

Other attempts have focussed on the formation of encoded proteins using the natural machinery of a cell and connecting the formed protein with the template nucleic acid that has coded for the amino acid components of the protein. Examples of suitable systems are phage display, E. coli display, ribosome display (WO 93/03172), and protein-mRNA-fusions (WO 98/31700). The genetic information of the nucleic acid, usually mRNA or DNA, may not necessarily be decoded between each round of selection to establish the identity of the chemical entities that has formed the protein because the nucleic acid can be amplified by known means, such as PCR, and processed for the formation of a new library enriched in respect of suitable binding proteins.

Recently, a new method for encoding molecules has been suggested, which can be performed in several selection rounds without intermediate decoding, wherein the molecule is not restricted to peptides and proteins. WO 02/00419 and WO 02/103008 disclose methods for preparing a molecule connected to a template coding for chemical entities which have reacted to form the molecule.

WO 02/074929 and WO 04/016767 also disclose template directed synthesis methods in which the reactive units of functional groups are reacted while hybridised to a template. This severely restricts the applicability of these prior art methods.

The methods of the prior art are restricted to reactions of the chemical entities which can be performed under hybridisation conditions. Hybridisation conditions generally imply aqueous solvents, moderate pH, and ambient temperature.

Further synthesis methods are disclosed in published PCT applications WO 2004/056994 and WO 2004/083427, hereby incorporated by reference in their entirety.

SUMMARY OF INVENTION

There exists a need for novel methods for molecule synthesis and library generation which can be carried out under conditions wherein hybridisation based chemical entity reactions cannot be carried out, such as e.g. chemical entity reactions carried out in non-aqueous solvents, at low and high pH outside the moderate pH values normally applied for aqueous solvents, and at low and high temperatures significantly below and above ambient temperatures.

Furthermore, the present invention is based on the principle that chemical entities initially provided on a building block oligonucleotide (i.e. a building block having an identifier oligonucleotide part which is linked to a chemical entity) can be brought into reactive proximity without the use of a template comprising a set of covalently linked codons.

Also, the present invention allows reaction of chemical entities when the chemical entities are linked to a single stranded identifier polynucleotide obtained by covalently linking the oligonucleotide parts (oligonucleotide identifiers) of the building blocks.

The single stranded identifier polynucleotides differ from template directed synthesis methods employing codon and anti-codon hybridisation between a template and one or more transfer units, i.e. methods wherein e.g. reactive units on transfer units are reacted while the anti-codon of the transfer units are hybridised to template codons (see e.g. WO 02/074929 and WO 04/016767 cited herein above).

Building blocks of the present invention are initially brought into reactive proximity by sequential or simultaneous hybridisation of building, block identifier nucleotides to connector oligonucleotides which differ from a template as no single connector oligonucleotide can direct the synthesis of an entire molecule.

While template directed synthesis is predetermined by the configuration of the codons along the template, which codons comprise all the information necessary for template directed synthesis, the present invention exploits the more flexible approach of initially generating a hybridisation complex between building block oligonucleotides and one or more connector oligonucleotides.

Accordingly, different building blocks comprising a chemical entity linked to the oligonucleotide (identifier) of the building block are thus brought into reactive proximity with each other. Following ligation—chemical, enzymatic, or otherwise—of the (identifier) oligonucleotides of hybridised building blocks, an identifier polynucleotide is formed.

The terms "building block oligonucleotide" and "building block identifier oligonucleotide" are used interchangeably herein.

The oligonucleotide identifier thus identifies the chemical entity attached—covalently, non-covalently or otherwise—to the identifier oligonucleotide of the building block, whereas the identifier polynucleotide is capable—once decoded—to identify the molecule having been synthesised, or to identify the chemical reactions which have taken place in order to synthesise the molecule.

In contrast to a template directed synthesis method, no template is used and no single identifier oligonucleotide becomes hybridised to all of the remaining building blocks.

The building blocks of the present invention can be illustrated as generally falling into 3 different groups as listed below:

a) building blocks comprising an identifier oligonucleotide linked to one or more chemical entities, b) building blocks comprising an identifier oligonucleotide linked to one or more reactive groups, and c) building blocks comprising or consisting of an identifier oligonucleotide, optionally an identifier oligonucleotide comprising a spacer region, wherein the building blocks of group c) are preferably connector oligonucleotides to which building blocks of groups a) and b) can hybridise.

In certain embodiments, class a) and b) building blocks will also be termed CCPN's herein below, whereas class c) building blocks will be termed CPN's. However, in certain other embodiments, both CPN's and CCPN's can be of the classes a) and b) listed herein immediately above.

Accordingly, when CCPN's are of class a) and b) and the CPN's are of class c), all the chemical entities to be reacted in the synthesis of a molecule will be provided by "building blocks" of classes a) and b) above. Building blocks of class c) above are a specialised form of building blocks also termed "connector oligonucleotides".

The oligonucleotide part of the building blocks (i.e. classes a) and b) above) can be ligated together following formation of a hybridisation complex also comprising connector oligonucleotides. This leads to the formation of an identifier polynucleotide to which the building block chemical entities are associated, covalently, non-covalently or otherwise.

Following separation (e.g. disruption of the hydrogen bonds mediating the hybridisation) of the identifier polynucleotide (linked to a plurality of chemical entities) from one or more optionally ligated CPN's, the chemical entities can be reacted under reaction conditions which are not compatible with maintaining the structure (i.e. upholding hybridisation of CPN's and CCPN's) of the above-mentioned hybridisation complex of CPN's and CCPN's.

The one or more optionally ligated CPN's can be removed from a reaction compartment in which the identifier polynucleotide is retained prior to reaction of the chemical entities. Alternatively, the chemical entities linked to the identifier polynucleotide can be reacted while the optionally ligated CPN's are present in the same reaction compartment, but not hybridised to the identifier polynucleotide.

Apart from allowing a wider range of reaction chemistries, the single stranded nature of the identifier polynucleotide also allows for more flexibility (i.e. movement of the chemical entities relative to each other) than the movement which is afforded by a hybridisation complex of CPN's and CCPN's.

In some preferred embodiments of the invention, individual identifier oligonucleotides comprise a "zipper box", i.e. a nucleotide sequence capable of hybridising to a "zipper box" of another or an adjacently positioned identifier oligonucleotide. The "zipper box" of e.g. a CCPN will not be involved in hybridisation of the CCPN to a CPN, but it will hybridise to a complementary "zipper box" of another CCPN and bring the chemical entities of the two CCPN's into reactive proximity.

Accordingly, two oligonucleotides may be provided with a zipper box, i.e. a first identifier oligonucleotide comprises a first part of a molecule pair being capable of specific and reversible interaction/hybridisation with a second identifier oligonucleotide comprising the second part of the molecule pair.

Typically, the molecule pair comprises nucleic acids, such as two complementary sequences of nucleic acids or nucleic acid analogs. In a certain aspect, the zipper domain polarity of the first oligonucleotide attached to a first chemical entity is reverse compared to the zipper domain polarity of the second oligonucleotide. Usually, the zipping domain is proximal to the chemical entity to allow for a close proximity of the chemical entities. In preferred embodiments, the zipping domain is spaced form the chemical entity with no more than 2 nucleic acid monomers. Typically, the zipping domain sequence comprises 3 to 20 nucleic acid monomers, such as 4 to 16, and preferably 5 to 10, depending on the conditions used.

DEFINITIONS

At least 1 single complementary connector oligonucleotide (CCPN) hybridizes to at least 2 connector oligonucleotides (CPN): The hybridization events leading to the formation of the supramolecular complex can occur simultaneously or sequentially in any order.

A bifunctional complex comprises a (final) molecule and the identifier polynucleotide which can be decoded to reveal the identity of the molecule—or the chemical reactions having resulted in the synthesis of the molecule. An intermediary form of the bifunctional complex will have been formed when a hybridisation complex is formed by hybridisation of at least 2 CCPNs and at least 1 CPN, wherein at least some of said hybridised CPNs and/or CCPNs will provide reactants, such as chemical entities comprising functional groups, to a method for synthesising the at least one molecule ultimately linked to the identifier polynucleotide of the bifunctional complex.

Branched CPN: Connector oligonucleotide comprising one or more branching points connecting linear or branched connector oligonucleotides.

Building block oligonucleotide: Generic term for a polynucleotide part linked to either a) a reactant such as a chemical entity comprising at least one reactive group (type I BBPN), or b) a reactive group (in the absence of a reactant or chemical entity) (type II BBPN), or the BBPN can simply comprise a polynucleotide part comprising a spacer region for spacing e.g. chemical entities of other BBPNs (type III BBPN). The term building block oligonucleotide thus includes CPNs and CCPNs irrespective of their type. In certain embodiments, building block oligonucleotide is used to describe a building block in which a chemical entity (or a reactive site) is linked to the (identifier) oligonucleotide of the building block (see building block oligonucleotides of classes a) and b) herein above). When this definition of building block oligonucleotide is applied, the corresponding definition of a connector oligonucleotide is the one used to describe building block oligonucleotides of class c) herein above.

Herein, the term "building block oligonucleotide" is used interchangeably with "building block identifier oligonucleotide".

A building block may be a CCPN or a CPN. At least some of the building blocks used in the methods described herein comprise a chemical entity or functional entity.

Complementary connector oligonucleotide (CCPN): A CCPN preferably comprises an oligo nucleotide part which can be linked to either a) a reactant such as a chemical entity comprising at least one reactive group (type I CCPN), or b) a reactive group (in the absence of a reactant or chemical entity) (type II CCPN). However, in certain embodiments, a CCPN can also comprise a polynucleotide part comprising a spacer region for spacing e.g. chemical entities of other CCPNs (type III CCPN). When the polynucleotide part of a CCPN is linked to a reactant, such as a chemical entity comprising at least one reactive group, the CCPN can act as a "donor CCPN" or as an "acceptor CCPN" and take part in the method for synthesising the at least one molecule. In some embodiments, some CCPNs will be "donor CCPNs" donating chemical entities to the synthesis of a molecule, whereas at least one other CCPN will be an "acceptor CCPN", or a CPN will be an "acceptor CPN". A method for synthesising at least one molecule exploiting one or more "donor CCPNs" comprising at least one reactant, such as at least one chemical entity, does not exclude using—in the same method—at least one "donor CPN" comprising at least one reactant, such as at least one chemical entity. The covalent or non-covalent bond between a chemical entity and a polynucleotide part of a "donor CCPN" can be cleaved before, during, or after the synthesis and formation of the molecule comprising reacted reactants, such as covalently linked chemical entities. A covalent bond will be generated between reactants or chemical entities associated with an acceptor CCPN, or an acceptor CPN, during the synthesis of the molecule comprising reacted reactants, such as chemical entities.

Connector oligonucleotide: One or more CPN's guide the synthesis of a molecule by "calling" for CCPNs capable of hybridizing to a CPN. In some embodiments, it is preferred that the CPNs comprise only a nucleotide part (connector oligonucleotides), and no reactant (or chemical entity) or reactive group(s) (CPN type III). However, in other embodiments, the nucleotide part of a CPN can be linked to at least one reactant (or chemical entity) comprising at least one reactive group (CPN type I), or the polynucleotide part of a CPN can be linked to a reactive group (in the absence of a reactant or chemical entity) (CPN type II).

Decoding: The nucleotide part of a CPN or a CCPN harbours information as to the identity of the corresponding reactant or chemical entity linked to the nucleotide part of the CPN or the CCPN. Following a selection step the chemical entities which have participated in the formation of the molecule can be identified. The identity of a molecule can be determined if information of the chemical entities can be established. However, it may be sufficient merely to obtain information on the chemical structure of the various chemical entities that have participated in the synthesis of the at least one molecule in order to deduce the full structure of the molecule, as structural constraints during the formation can aide the identification process. As an example, the use of different kinds of attachment chemistries may ensure that a chemical entity on a building block can only be transferred to a certain position on a scaffold. Another kind of chemical constraints may be present due to steric hindrance on the scaffold molecule or the chemical entity to be transferred. In general however, it is preferred that information can be inferred from an identifier polynucleotide that enable the identification of each of the chemical entities that have participated in the formation of the molecule along with the point in time in the synthesis history when the chemical entities have been incorporated in a (nascent or intermediate) molecule.

Although conventional DNA sequencing methods are readily available and useful for this determination, the amount and quality of isolated bifunctional molecule hybridisation complexes linked to a molecule having the desired property may require additional manipulations prior to a sequencing reaction. When the amount is low, it is preferred to increase the amount of the identifier polynucleotide by polymerase chain reaction (PCR) using PCR primers directed to primer binding sites present in the identifier polynucleotide. In addition, the quality of the library may be such that multiple species of different bifunctional molecules are co-isolated by virtue of similar capacities for binding to a target.

In cases where more than one species of bifunctional molecule are isolated, the different isolated species can suitably be separated prior to sequencing of the identifier polynucleotide.

Thus in one embodiment, the different identifier polynucleotides of the isolated bifunctional complexes are cloned into separate sequencing vectors prior to determining their sequence by DNA sequencing methods. This is typically accomplished by amplifying all of the different identifier polynucleotides by PCR, and then using unique restriction endonuclease site(s) on the amplified product to directionally clone the amplified fragments into sequencing vectors. The cloning and sequencing of the amplified fragments is a routine procedure that can be carried out by any of a number of molecular biological methods known in the art.

Alternatively, the bifunctional complex or the PCR amplified identifier polynucleotide can be analysed in a microarray. The array may be designed to analyse the presence of a single subsequence or multiple subsequences in an identifier polynucleotide.

Chemical entity: Part of a building block oligonucleotide—or a CPN or a CCPN. When building blocks are used in which the oligonucleotide part is linked to a chemical entity, corresponding connector oligonucleotides preferably consists only of an at least partly complementary oligonucleotide sequence, but no reactive group or chemical entity. Chemical entities comprise at least one reactive group used for reacting a chemical entity with another chemical entity. The chemical entity comprises a part of or an intermediate or precursor of the molecule to be synthesised. A chemical entity can also comprise the product of a reaction having previously taken place between different chemical entities, i.e. the term also applies to intermediate products being generated prior to or during the synthesis of the molecule.

Chemical entities serve the function of being precursors for the molecule to be synthesised. Therefore, when it is stated in the present application that a chemical entity is linked to another chemical entity through the reaction of the reactive groups of respective chemical entities, it is to be understood that not necessarily all the atoms of the original chemical entity are to be found on the final molecule having been synthesised. Also, as a consequence of the reactions involved in the linking, the structure of the chemical entity can be changed when it appears on the molecule. Especially, the cleavage resulting in the release of the chemical entity may generate reactive group(s) which in a subsequent reaction can participate in the formation of a connection between the (nascent or intermediate) molecule and a further chemical entity. Furthermore, two or more chemical entities may generate an intermediate which can be reacted with a third (or further) chemical entity to form a nascent (intermediate) or final molecule.

The connection or linking between chemical entities or, alternatively, a chemical entity and a nascent (intermediate) molecule, is aided by one or more reactive groups of the chemical entities. The reactive groups may be protected by any suitable protecting groups which need to be removed prior to the linking of the chemical entities. Dependent on the reaction conditions used, the reactive groups may also need to be activated. A chemical entity featuring a single reactive group may suitably be used i.a. in the end positions of polymers or to be reacted with a scaffold, whereas chemical entities having two or more reactive groups intended for the formation of linkage between chemical entities, are typically present as scaffolds or in the body part of a polymer. A scaffold is a core structure, which forms the basis for creating multiple variants of molecules based on the same set of chemical entities to be reacted in different combinations in order to generate the variants. The variant forms of the scaffold is typically formed through reaction of reactive groups of the scaffold with reactive groups of other chemical entities, optionally mediated by fill-in groups or catalysts, under the creation of a covalent linkage.

Chemical entity reactive group: Each chemical entity comprises at least one reactive group the reaction of which with a reactive group of a separate chemical entity results in the formation of covalently linked chemical entities, or parts thereof.

A reactive group of a chemical entity may be capable of forming a direct linkage to a reactive group of another chemical entity, or a nascent or intermediate molecule, or a reactive group of a chemical entity may be capable of forming a connection to a reactive group of another chemical entity through a bridging fill-in group. It is to be understood that not all the atoms of a reactive group are necessarily maintained in the connection formed. Rather the reactive groups are to be regarded as precursors for the linkage formed.

Hybridization complex: Plurality of CPN's hybridised to a plurality of CCPN's. The overlap of complementary polynucleotides of CPNs and CCPNs hybridising to one another is preferably 4 or more nucleotides, such as e.g. 6 nucleotide overlaps, for example overlaps of 10-12 nucleotides. A hybridisation complex is an intermediary in the synthesis of a bifunctional complex comprising a molecule and an identifier polynucleotide capable of identifying said molecule.

Linear CPN: CPN comprising a sequence of covalently linked nucleotides.

Molecule: Molecule having been synthesised by the reaction of chemical entities on different building blocks, i.e. the molecule being the reaction product when reactive groups of different (i.e. separate) chemical entities are reacted, when chemical entities are joined together, or when chemical entities are linked to a scaffold. The formation of a molecule involves in one embodiment the reaction of at least one chemical entity, or part thereof, a) of one or more CCPN(s) with one or more separate CCPN(s), and/or b) of one or more CPN(s) with one or more separate CPN(s), and/or c) of one or more CPN(s) with one or more CCPN(s), and/or d) of one or more CCPN(s) with one or more CPN(s), preferably by reacting at least 2, such as at least 3, 4, 5, 6, 7, 8, 9, 10, 11, 12, 13, 14, 15, 16, 17, 18, 19, 20 chemical entity reactive groups in order to synthesise the molecule.

Other reactive groups: Groups the reaction of which does not result in the formation of a molecule comprising covalently linked chemical entities.

Plurality: At least 2, such as 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, such as 45, 50, 55, 60, 65, 70, 75, 80, 85, 90, 95, 100, for example, 200, 300, 400, 500, 600, 700, 800, 900, 1000, such as more than 1000.

Reactant: Precursor moiety for a structural unit in the synthesised molecule. The reaction of reactants result in the formation of at least one molecule in accordance with the methods of the present invention.

Reacting chemical entity reactive groups: A molecule is generated by reactions involving chemical entity reactive groups. Reacting chemical entity reactive groups of separate chemical entities results in linking the chemical entities, or a part thereof, by covalent bonds. Types of reactive groups and types of reactions involving such reactive groups are listed in FIG. 6. The listing is merely illustrative for selected reaction types and not exhaustive. Although FIG. 6 illustrates reactions between chemical entities on building blocks which are hybridised to a connector oligonucleotide, the same reactions can take place when chemical entities on an identifier polynucleotide are reacted.

Reactive group: Activatable part of e.g. a reactant, such as a chemical entity, i.e. a (reactive) group forming part of, being integrated into, being linked to, or otherwise associated with, a building block oligonucleotide of type I as designated herein. A reactive group, such as e.g. a catalyst, can also occur on its own without forming part of, being integrated into, being linked to, or otherwise associated with, a reactant, such as a chemical entity. In the latter case the reactive group is linked to the polynucleotide part of a building block oligonucleotide of type II as designated herein.

Spacer region: Region on a CPN or CCPN capable of separating and/or spatially organising chemical entities located on adjacently positioned CPNs or CCPNs in a hybridisation complex. In one embodiment the spacer region is the region of a building block polynucleotide not hybridised to another building block oligonucleotide. The polynucleotide part of both CPNs and CCPNs can comprise a spacer region, optionally in the absence of a chemical entity or a reactive group linked to said polynucleotide part. In some embodiments, a building block oligonucleotide comprising a spacer region in the polynucleotide part of the building block oligonucleotide does not comprise a reactant or a chemical entity or a reactive group (participating in molecule formation) linked to said polynucleotide part of said building block oligonucleotide. However, building block oligonucleotides comprising such reactants or chemical entities or reactive groups linked to the polynucleotide part of the building block oligonucleotide may further comprise a spacer region, such as e.g. a region of the polynucleotide part of the building block oligonucleotide which does not hybridise to the polynucleotide part of other building block oligonucleotides. In such embodiments, it will be understood that CPNs of type III and CCPNs of type III (as designated herein elsewhere) do not also comprise one or more reactants, or one or more chemical entities, or one or more reactive groups participating in molecule formation. Spacer regions can be designed so that they are capable of self-hybridization and hair-pin structure formation. "Spacer regions" or "hybridisation regions" can be nucleotides to which no chemical entities and no reactive groups are attached.

Zipper box: Linkers linking chemical entities to e.g. the polynucleotide part of a CPN or a CCPN can comprise a "zipper box". Two linkers may be provided with a zipper box, i.e. a first linker comprises a first part of a molecule pair being capable of reversible interaction with a second linker comprising the second part of the molecule pair. Typically, the molecule pair comprises nucleic acids, such as two complementary sequences of nucleic acids or nucleic acid analogs. In a certain aspect, the zipper domain polarity of the CCPN harbouring the first linker attached to the first chemical entity is reverse compared to the zipper domain polarity of the CCPN harbouring the second chemical entity. Usually, the zipping domain is proximal to the chemical entity to allow for a close proximity of the chemical entities. In preferred embodiments, the zipping domain is spaced form the chemical entity with no more than 2 nucleic acid monomers. Typically, the zipping domain sequence comprises 3 to 20 nucleic acid monomers, such as 4 to 16, and preferably 5 to 10, depending on the conditions used.

The annealing temperature between the nucleic acid part of the CCPN and a CPN is usually higher than the annealing temperature of the zipper box molecule pair to maintain the hybridisation complex during the reaction. Usually, the difference between the annealing temperatures is 10° C., such as 25° C., or above. In a certain embodiment of the invention, the conditions during assembling of the hybridisation complex includes a concentration of the CCPN and CPN which is higher than the concentration during reaction to allow for optimal dimerisation conditions for the two parts of the molecule pair. The concentration during the assembly of the hybridisation complex is in a preferred aspect at least 10 times higher compared to the concentration used for dimerisation of the to parts of the molecule pair. In a certain aspect, the reaction step is performed by altering the temperature below and above the annealing temperature of the zipping domain, however ensuring that the hybridisation complex retains its integrity.

DETAILED DESCRIPTION OF THE DRAWINGS

Figure 1C:
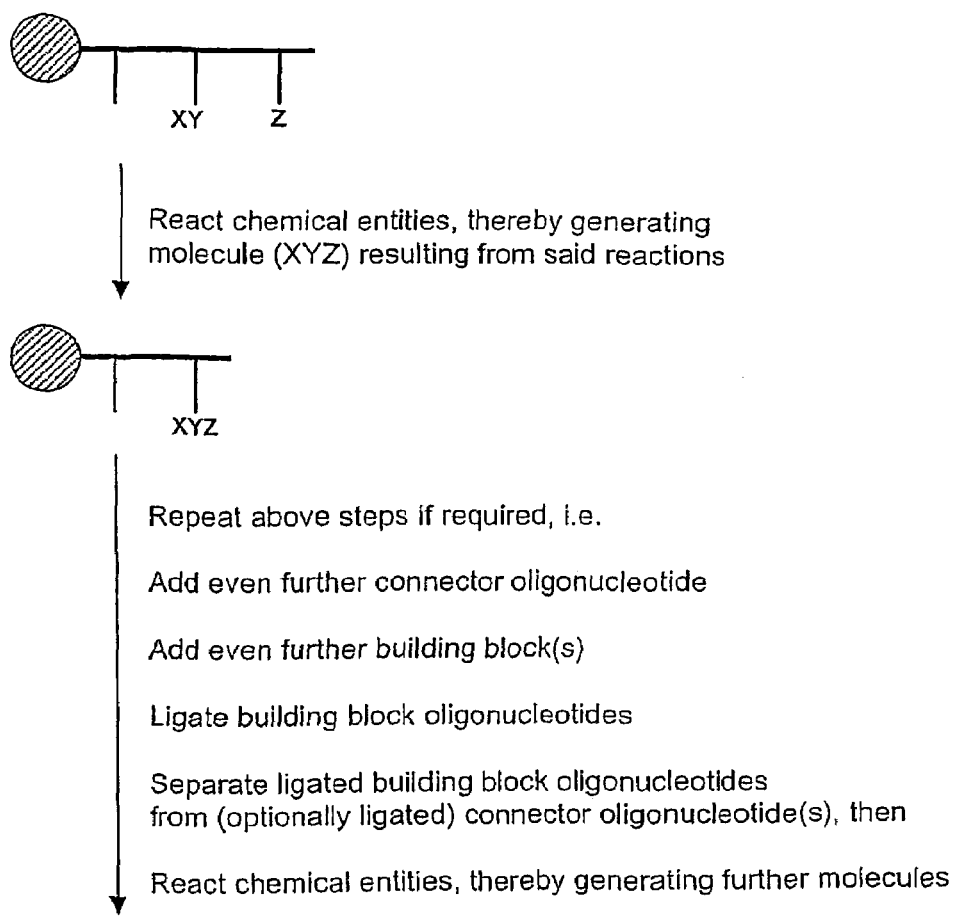

FIG. 1 illustrates one embodiment of the present invention. A building block is attached to a solid support through the oligonucleotide part of the building block. X denotes a chemical entity. A connector oligonucleotide is added sequentially or simultaneously with the addition of another building block (Y denotes a chemical entity). A hybridisation complex is formed between the connector and the building block oligonucleotides. The oligonucleotide part of each of the building blocks is ligated and the identifier polynucleotide thus created is separated from the connector oligonucleotide. After separation of identifier polynucleotide and the connector oligonucleotide, chemical entities X and Y attached to the identifier polynucleotide are reacted, and the reaction product XY is formed. Further steps pertain to the addition of a further connector oligonucleotide—sequentially or simultaneously with the addition of a further building block (Z denotes a chemical entity). A hybridisation complex is formed between the identifier polynucleotide of the bifunctional complex resulting from the reaction of chemical entities X and Y, the further connector oligonucleotide and the further building block oligonucleotide carrying chemical entity Z. The oligonucleotide part of the further building block is ligated to the identifier polynucleotide and the further identifier polynucleotide thus created is separated from the connector oligonucleotide. After separation of identifier polynucleotide and the connector oligonucleotide, the further chemical entity Z is reacted with XY attached to the identifier polynucleotide, and the reaction product XYZ is formed. It is possible to repeat the above steps one or more times. X, Y and Z need not be identical before and after reaction of the respective chemical entity reactive groups.

FIG. 2 illustrates another embodiment of the present invention. A connector oligonucleotide is attached to a solid support. Building blocks and one or more connector oligonucleotides are added and a hybridisation complex is allowed to form. The oligonucleotide part of each of the building blocks carrying chemical entities X, Y and Z are ligated and separated from optionally ligated connector oligonucleotides. The separation can be a disruption of hydrogens bonds in the hybridisation complex, or a physical separation to another reaction compartment. After separation, chemical entities X, Y and Z are reacted and the reaction product XYZ is formed. It is possible to repeat the above steps one or more times. X, Y and Z need not be identical before and after reaction of the respective chemical entity reactive groups.

Figure 3:
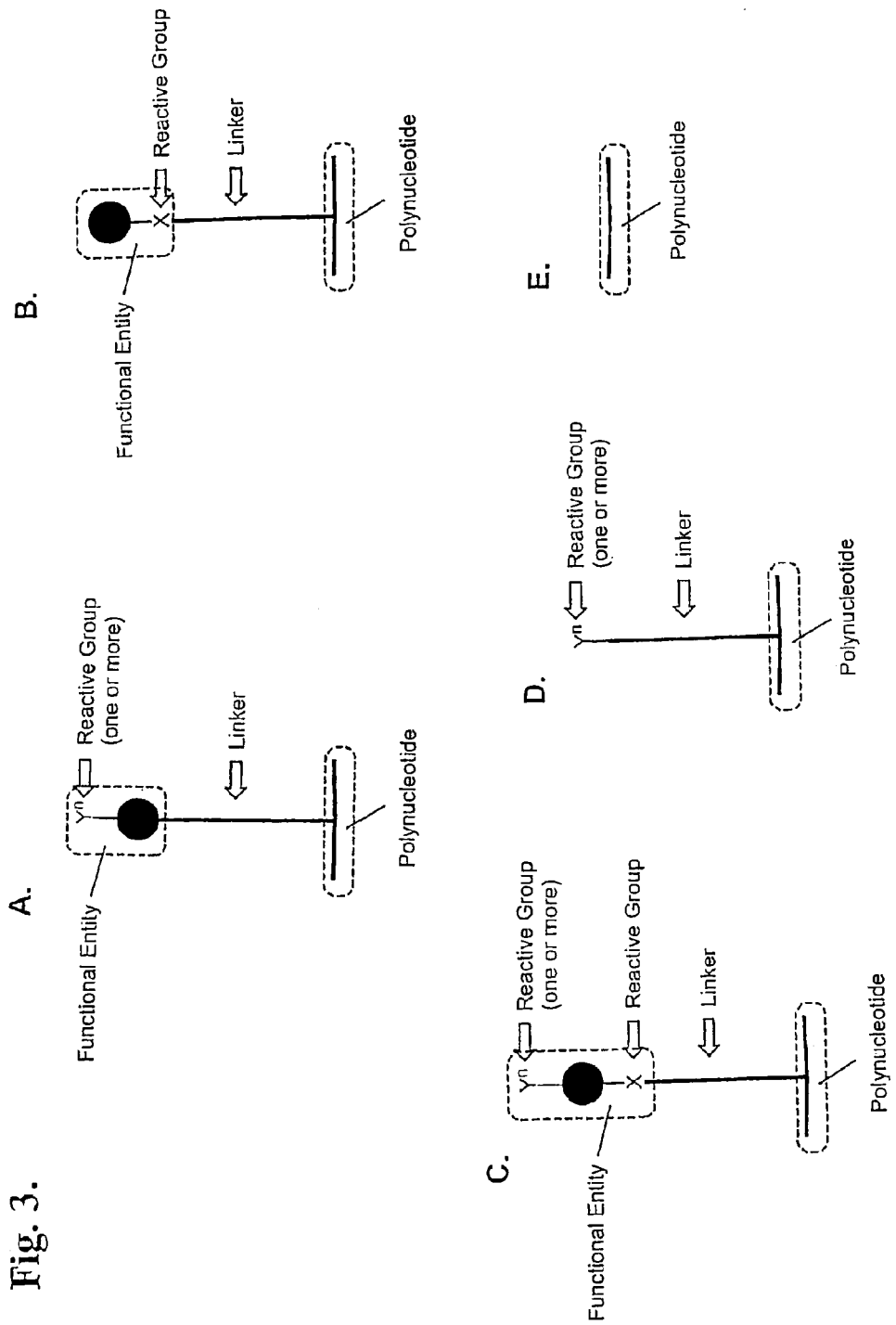

FIG. 3 illustrates different examples of building blocks and connector oligonucleotides. Building blocks preferably comprise a functional entity (FE). The terms "Functional entity" and "chemical entity" are used interchangeably herein.

A.) A building block containing an oligonucleotide/polynucleotide sequence, a linker and a functional entity carrying one or more reactive groups. The linker may optionally be cleavable and may comprise an oligonucleotide, a natural or unnatural peptide or a polyethyleneglycol (PEG), a combination thereof or other linkers generally used in organic synthesis, combinatorial chemistry or solid phase synthesis.

B.) Similar to A with a different positioning of the reactive group.

C.) A combination of type A and type B.

D.) This building block/connector only contains a reactive group and not a functional entity in the sense of types A, B and C.

E.) A spacer building block/connector without functional entity.

FIG. 4 illustrates a further set of examples of building blocks and connectors, wherein the linker maybe placed at one end of the polynucleotide sequence. In examples E. and F. the oligonucleotides neither carry a functional entity nor a reactive group. In example E. the oligonucleotide may be capable of self association e.g. through complementary nucleotide sequences, whereby hybridization can occur. In example F., part of the oligonucleotide loops out upon association such as e.g. hybridization with a building block. In this example no self association occurs.

FIG. 5 illustrates the principle of a zipperbox. The zipperbox is a region optionally comprising an oligonucleotide sequence where said region is capable of hybridizing to another zipperbox, wherein this second zipperbox optionally comprises an oligonucleotide sequence complementary to the first zipperbox. The zipperbox may be situated on a building block or a connector. Upon hybridization of two zipperboxes, the proximity between functional entity reactive groups increases, whereby the reaction is enhanced. By operating at a temperature that allows transient interaction of complementary zipperboxes, functional entity reactive groups are brought into close proximity during multiple annealing events, which has the effect of reactive groups in close proximity in a larger fraction of the time than otherwise achievable. Alternatively, one may cycle the temperature between a low temperature (where the zipper boxes pairwise interacts stably), and a higher temperature (where the zipper boxes are apart, but where the complex remains stable). By cycling between the high and low temperature several times, a given reactive group is exposed to several reactive groups, and eventually will react to form a bond between two function entities through their reactive groups.

FIG. 6 illustrates reaction types allowing simultaneous reaction and linker cleavage. Different classes of reactions are shown which mediate translocation of a functional group from one building block to another, or to an anchorage oligonucleotide. The reactions illustrated are compatible with simultaneous reaction and linker cleavage, i.e. one functional entity is transferred (translocated) directly from one building block onto another building block without the need of subsequent and separate linker cleavage through the application of further new conditions allowing for such.

(A) Reaction of nucleophiles with carbonyls. As a result of the nucleophilic substitution, the functional group (entity) R is translocated to the building block initially carrying the nucleophile.

(B) Nucleophilic attack by the amine on the thioester leads to formation of an amide bond, in effect translocating the functional group R of the thioester to the other building block.

(C) Reaction between hydrazine and β-ketoester leads to formation of pyrazolone, in effect translocating the R and R' functional groups to the other building block.

(D) Reaction of hydroxylamine with β-ketoester leads to formation of the isoxazolone, thereby translocating the R and R' groups to the other building block.
(E) Reaction of thiourea with β-ketoester leads to formation of the pyrimidine, thereby translocating the R and R' groups to the other building block.
(F) Reaction of urea with malonate leads to formation of pyrimidine, thereby translocating the R group to the other building block.
(G) Depending on whether Z=O or Z=NH, a Heck reaction followed by a nucleophilic substitution leads to formation of coumarin or quinolinon, thereby translocating the R and R' groups to the other building block.
(H) Reaction of hydrazine and phthalimides leads to formation of phthalhydrazide, thereby translocating the R and R' groups to the other building block.
(I) Reaction of amino acid esters leads to formation of diketopiperazine, thereby translocating the R group to the other building block.
(J) Reaction of urea with α-substituted esters leads to formation of hydantoin, and translocation of the R and R' groups to the other building block.
(K) Alkylation may be achieved by reaction of various nucleophiles with sulfonates. This translocates the functional groups R and R' to the other building block.
(L) Reaction of a di-activated alkene containing an electron withdrawing and a leaving group, whereby the alkene is translocated to the nucleophile carrying building block.
(M) Reaction of disulfide with mercaptane leads to formation of a disulfide, thereby translocating the R' group to the other building block.
(N) Reaction of amino acid esters and amino ketones leads to formation of benzodiazepinone, thereby translocating the R group to the other building block.
(O) Reaction of phosphonium salts with aldehydes or ketones leads to formation of substituted alkenes, thereby translocating the R" group to the other building block.
(P) Reaction of phosphonates with aldehydes or ketones leads to formation of substituted alkenes, thereby translocating the R" group to the other building block.
(Q) The principle of translocation of e.g. aryl groups from one building block to another building block.
(R) Reaction of boronates with aryls or heteroaryls results in transfer of an aryl group to the other building block (to form a biaryl).
(S) Reaction arylsulfonates with aryl groups bound as Boron derivatives leads to transfer of the aryl group.
(T) Biaryl formation through translocation of one aryl group to another building block.
(U) Arylamine formation (e.g. Hartwig/Buchwald type of chemistry) through N-arylation, i.e. transfer of aryl groups to building blocks carrying amino groups.
(V) As U using hypervalent iodonium derivatives.
(W) (Omitted)
(X) Reaction of boronates with vinyls (or alkynes) results in transfer of an aryl group to the other building block to form a vinylarene (or alkynylarene).
(Y) Reaction between aliphatic boronates and arylhalides, whereby the alkyl group is translocated to yield an alkylarene.
(Z) Transition metal catalysed alpha-alkylation through reaction between an enolether and an arylhallide, thereby translocating the aliphatic part.
(AA) Condensations between e.g. enamines or enolethers with aldehydes leading to formation of alpha-hydroxy carbonyls or alpha, beta-unsaturated carbonyls. The reaction translocates the nucleophilic part.
(AB) Alkylation of alkylhalides by e.g. enamines or enolethers. The reaction translocates the nucleophilic part.
(AC) [2+4]cycloadditions, translocating the diene-part.
(AD) [2+4]cycloadditions, translocating the ene-part.
(AE) [3+2]cycloadditions between azides and alkenes, leading to triazoles by translocation of the ene-part.
(AF) [3+2]cycloadditions between nitriloxides and alkenes, leading to isoxazoles by translocation of the ene-part.

Figure 7A:
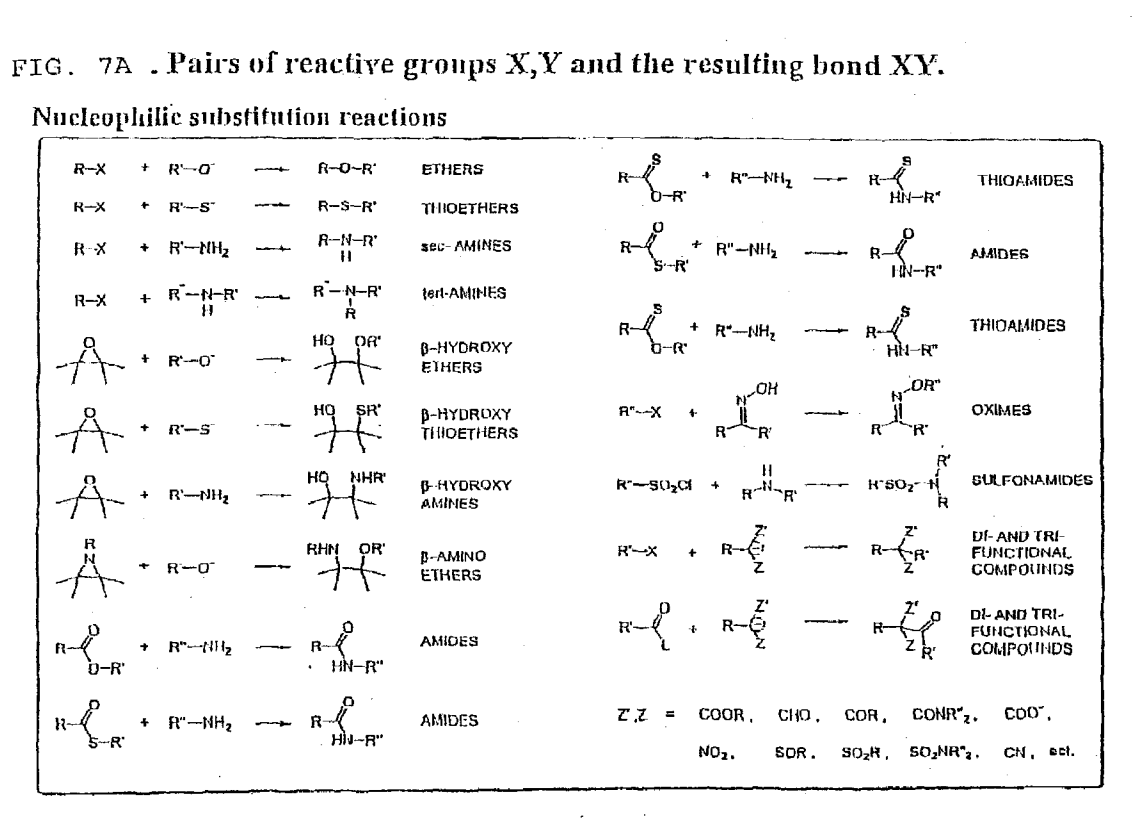
Figure 7C:
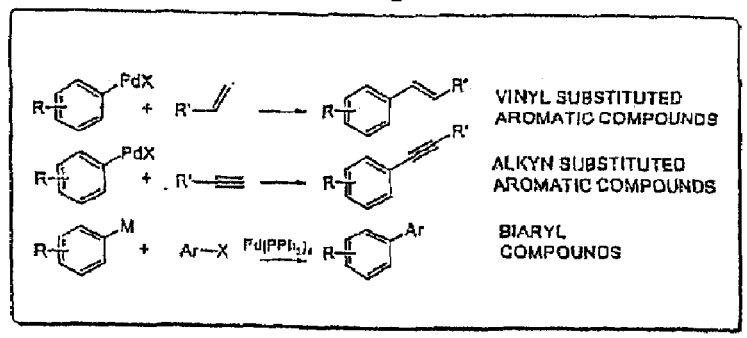

FIG. 7 illustrates pairs of reactive groups (X) and (Y), and the resulting bond (XY). (A) nucleophilic substitution reactions, (B) Aromatic substitution reactions (C) transitional metal catalyzed reactions (D) addition to carbon-carbon multiple bonds (E) as in (D), but producing multifunctional compounds (F) cylcoaddition to multiple bonds (G) addition to carbon-netero multiple bonds.

A collection of reactive groups and functional entity reactive groups that may be used for the synthesis of molecules are shown, along with the bonds formed upon their reaction. After reaction, linker cleavage may be applied to release one of the functional entities, whereby the transfer of one functional entity from one building block to another is effectuated.

FIG. 8 illustrates cleavable linkers, for the formation of (A) ketones, aldehydes amides and acids (B) ketones, amides and acids (C) aldehydes and ketones (D) alcohols and acids (E) amines and alcohols (F) esters, thioesters, amides and alcohols (G) sulfonamides and alcohols (H) ketones, amines and alcohols (I) ketones, amines, alcohols and mercaptanes (J) biaryl and bihetaryl (K) benzyles, amines, anilins, alcohols and phenoles (L) mercaptanes (M) glycosides (N) aldehydes and glyoxylamides (O) aldehydes, ketones and aminoalcohols. The composition of the linker may include derivatives of the following, but is not limited hereto:

Carbohydrides and substituted carbohydrides
Vinyl, polyvinyl and substituted polyvinyl
Acetylene, polyacetylene
Aryl/Hetaryl, polyaryl/hetaryl and substituted polyaryl/polyhetaryl
Ethers, polyethers such as e.g. polyethyleneglycol and substituted polyethers
Amines, polyamines and substituted polyamines
Double stranded, single stranded or partially double or single stranded natural and unnatural polynucleotides and substituted double stranded, single stranded or partially double stranded natural and unnatural polynucleotides such as but limited to DNA, RNA, LNA, PNA, TNA
Polyamides and natural and unnatural polypeptides and substituted polyamides and natural and unnatural polypeptides
Phosphate containing linkers
Any combination of the above Linkers may be cleavable or non-cleavable. The figure illustrates cleavable linkers, conditions for their cleavage, and the resulting products are shown.

Different examples of the formation of CCPN's carrying functional entities. Reactions and reagents are shown that may be used for the coupling of functional entities to modified oligonucleotides (modified with thiol, carboxylic acid, halide, or amine), without significant reaction with the unmodified part of the oligonucleotide or alternatively, connective reactions for linkage of linkers to complementing elements. Commercially, mononucleotides are available for the production of starting oligonucleotides with the modifications mentioned.

FIG. 9 illustrates a CPN having a complementary hybridizing region 1 and a complementary hybridizing region 2—represented by the symbols illustrated in the figure. The descriptors of CCPN 1 and CCPN 2, respectively, are indicated in the figure.

Figure 10:
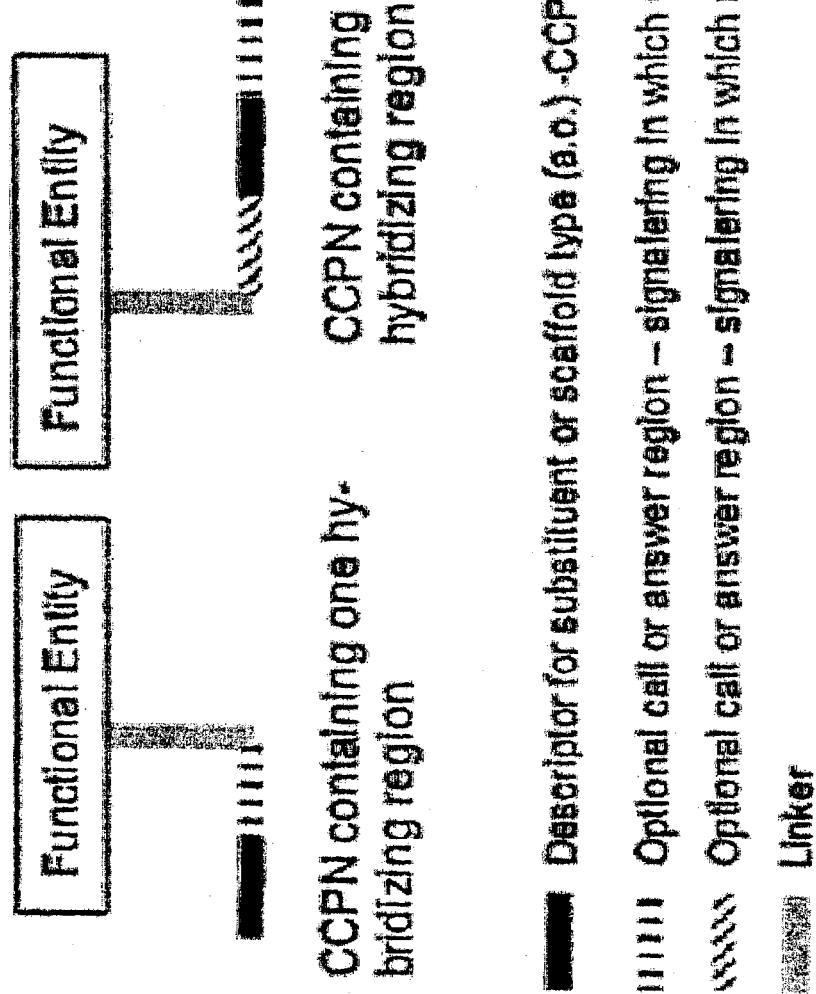

FIG. 10 illustrates a CPN containing one hybridizing region (left panel) and a CCPN containing two hybridizing regions (right panel), respectively. Each hybridizing region is linked by a linker to a functional entity. Symbols reference different CCPN regions as stated.

Figure 11:
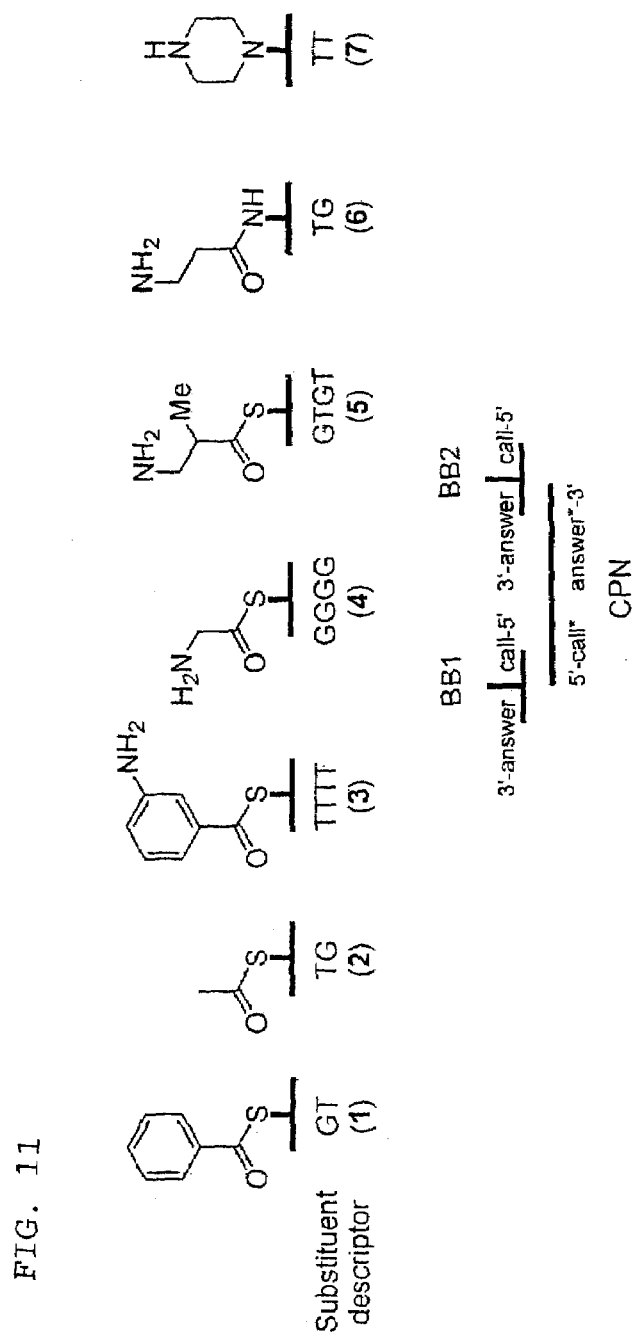

FIG. 11 illustrates a hybridization complex, wherein a CPN having a 5' call region (5'-call*) and a 3' answer region (answer*-3') is hybridized to each of two CCPN's carrying chemical entities to be reacted (designated BB1 and BB2, respectively). A 5' call region (call-5') and a 3' answer region (3'-answer) is indicated for each CCPN.

FIG. 11 also shows possible identifier polynucleotide sequences for CCPN's in a peptide like library composed of complementary connectors 1-7.

DETAILED DESCRIPTION OF THE INVENTION

Below is described further embodiments of the methods of the invention for synthesising at one or more molecules. The below embodiments are concerned exclusively with the provision of different types of hybridisation complexes comprising a plurality of CPNs (connector oligonucleotides) hybridised to a plurality of CCPNs (building block oligonucleotides comprising one or more chemical entities the reaction of which is involved in the formation of the molecule to be synthesised).

It is to be understood that in a further step of the methods of the invention, following the formation of a hybridisation complex comprising connector oligonucleotides and building block oligonucleotides as described in detail herein below, the building block oligonucleotides are ligated or otherwise covalently linked, and the ligated building block oligonucleotides are separated from optionally ligated connector oligonucleotides.

The below non-exhaustive examples and embodiments specify some of the possibilities for providing CPNs (connector oligonucleotides) and CCPNs (building block oligonucleotides) and forming hybridisation complexes comprising a plurality of CPNs (connector oligonucleotides) hybridised to a plurality of CCPNs (building block oligonucleotides). It will be understood that all or only some of the CPNs (connector oligonucleotides) and CCPNs (building block oligonucleotides) provided can comprise a polynucleotide part linked to a chemical entity. For all of the below embodiments, the at least one molecule is generated by reacting reactants positioned on separate CPNs (connector oligonucleotides) and/or separate CCPNs (building block oligonucleotides) prior to the formation of the at least one molecule.

Although most of the disclosed embodiments herein below illustrate chemical entities linked to an identifier oligonucleotide of a building block (CCPN) and hybridised to one or more connector oligonucleotides (CPNs) prior to said building block identifier oligonucleotides being ligated, the invention is not limited to this single embodiment. However, for the sake of illustrating the principle of the methods of the invention, the below examples employ building blocks wherein a chemical entity is linked to an identifier oligonucleotide, and connector oligonucleotides capable of hybridising to the building block identifier oligonucleotides and bringing the chemical entities into reactive proximity.

Although not illustrated in the following schemes, at least one connector oligonucleotide or at least one building block oligonucleotide can be immobilised, i.e. attached to a solid support, such as a polymer bead. This feature enables easy separation of the identifier polynucleotide (obtained from ligation of building block oligonucleotides) from optionally ligated connector oligonucleotides. This is illustrated in principle in FIGS. 1 and 2.

In one aspect of the present invention, a method is provided for synthesising one or more bifunctional complexes each comprising a) a molecule resulting from the reaction of a plurality of chemical entities and b) an identifier polynucleotide identifying one or more or all of the chemical entities having participated in the synthesis of the molecule, said method comprising the steps of i) providing a plurality of building blocks at least some of which comprise one or more chemical entities linked to an identifier oligonucleotide, ii) providing one or more connector oligonucleotides capable of hybridising to the identifier oligonucleotides of the building blocks provided in step i), iii) hybridising identifier oligonucleotides of the building blocks to the one or more connector oligonucleotides, iv) ligating identifier oligonucleotides hybridised to connector oligonucleotide(s), thereby generating an identifier polynucleotide comprising covalently linked identifier oligonucleotides at least some of which are linked to one or more chemical entities, v) separating the identifier polynucleotide from the one or more optionally ligated connector oligonucleotide(s) (e.g. so that the polynucleotide and oligonucleotide do not interact with each other to form stable hydrogen bonds in an ordered fashion)

vi) reacting the chemical entities linked to the identifier polynucleotide in the absence of hybridisation between identifier oligonucleotides and connector oligonucleotides, and vii) obtaining a bifunctional complex comprising a molecule resulting from the reaction of the chemical entities, said molecule being linked to an identifier polynucleotide identifying at least some and preferably all of the chemical entities having participated in the synthesis of the molecule.

In another aspect of the present invention, a method is provided for synthesising a bifunctional complex comprising a molecule resulting from the reaction of a plurality of chemical entities, wherein said molecule is linked to an identifier polynucleotide identifying one or more of the chemical entities having participated in the synthesis of the molecule, said method comprising the steps of i) providing a plurality of building blocks selected from the group consisting of a) building blocks comprising an identifier oligonucleotide linked to one or more chemical entities, b) building blocks comprising an identifier oligonucleotide linked to one or more reactive groups, and c) building blocks comprising an identifier oligonucleotide comprising a spacer or hybridisation region, wherein said building blocks comprising a spacer or hybridisabon region are preferably connector oligonucleotides to which building blocks of groups a) and b) can hybridise, ii) generating a hybridisation complex comprising at least n building blocks by hybridising the identifier oligonucleotide of one building block to the identifier oligonucleotide of at least one other building block, wherein n is an integer of 4 or more wherein at least 3 of said at least n building blocks comprise a chemical entity, wherein no single identifier oligonucleotide is hybridised to all of the remaining identifier oligonucleotides, wherein optionally at least one of said building blocks of group c) is immobilised to a solid support, thereby providing a handle to which an oligonucleotide of at least one building block of groups a) or b) can hybridise, iii) covalently linking identifier oligonucleotides of building blocks comprising one or more chemical entities, thereby obtaining at least one identifier polynucleotide comprising covalently linked identifier oligonucleotides each associated with one or more chemical entities, iv) optionally separating said identifier polynucleotide obtained in step iii) from any optionally immobilised connector oligonucleotides hybridised thereto, wherein said separation optionally comprises the step of diverting said identifier polynucleotide comprising covalently linked identifier oligonucleotides each associated with one or more chemical entities to a different reaction compartment, thereby separating said identifier polynucleotide from said optionally immobilised connector oligonucleotides v) reacting said at least 3 chemical entities linked to the identifier polynucleotide in the absence of hybridisation between identifier oligonucleotides and connector oligonucleotides, and vi) obtaining a bifunctional complex comprising a molecule resulting from the reaction of a plurality of chemical entities, wherein said molecule is linked to an identifier polynucleotide identifying one or more of the chemical entities having participated in the synthesis of the molecule;

preferably, all chemical entities to be reacted are linked to the same identifier nucleotide.

In a third aspect of the present invention, a method is provided for generating a library of bifunctional complexes comprising a molecule and an identifier polynucleotide capable of identifying the chemical entities having participated in the synthesis of the molecule, or identifying the reaction steps having led to the synthesis of the molecule, said method comprising the steps of hybridising a plurality of building block identifier oligonucleotides to a plurality of connector oligonucleotides each capable of hybridising to one or more building block oligonucleotides, said building block identifier oligonucleotides being linked to one or more chemical entities, covalently linking said building block oligonucleotides hybridised to one or more connector oligonucleotides, thereby generating a plurality of identifier polynucleotides linked to a plurality of non-reacted chemical entities, separating the identifier polynucleotides from the optionally ligated connector oligonucleotides, preferably by degrading the optionally ligated connector oligonucleotides and/or by performing a washing step wherein the identifier polynucleotides are associated with a solid support capable of being separated from non-bound, optionally ligated connector oligonucleotides.

reacting chemical entities linked to each of a plurality of different identifier polynucleotides, and generating a library of bifunctional complexes each comprising a different molecule and an identifier polynucleotide identifying the chemical entities having participated in the synthesis of the molecule, wherein each of the plurality of molecules are generated by reacting at least 2 chemical entities associated with different building block oligonucleotides.

In a fourth aspect of the present invention, a method is provided for synthesising a plurality of different molecules, said method comprising providing a plurality of connector oligonucleotides each capable of hybridizing to at least 1 complementary connector oligonucleotide, providing a plurality of complementary connector oligonucleotides selected from the group consisting of a) complementary connector oligonucleotides comprising at least 1 chemical entity comprising at least 1 reactive group, b) complementary connector oligonucleotides comprising at least 1 reactive group, c) complementary connector oligonucleotides comprising at least 1 spacer region, hybridizing the plurality of connector oligonucleotides and complementary connector oligonucleotides, thereby forming a plurality of different hybridisation complexes, each hybridisation complex comprising at least 2 complementary connector oligonucleotides and at least 2 connector oligonucleotides, wherein, for each of said hybridisation complexes, at least 2 of said complementary connector oligonucleotides comprise at least 1 chemical entity comprising at least 1 reactive group, and at least 1 of said complementary connector oligonucleotides hybridizes to at least 2 connector oligonucleotides, and ligating, enzymatically, chemically, or otherwise, complementary connector oligonucleotides, thereby forming identifier polynucleotides, wherein each identifier polynucleotide is associated with a plurality of unreacted chemical entities, separating each identifier polynucleotide associated with unreacted chemical entities from optionally ligated connector oligonucleotides associated therewith, reacting, when the identifier polynucleotides are no longer hybridised to the optionally ligated connector oligonucleotides, at least 2 chemical entity reactive groups of each polynucleotide identifier by reacting at least 1 reactive group of each chemical entity, wherein, for each bifunctional complex, the reaction of said chemical entity reactive groups results in the formation of a different molecule by reacting at least 2 chemical entities provided by separate complementary connector oligonucleotides, thereby synthesising a plurality of different molecules.

In one embodiment, at least n connector oligonucleotides and at least n building block oligonucleotides are provided, n being an integer of preferably from 3 to 6, and at least n−1 building block oligonucleotides hybridize to at least 2 connector oligonucleotides. There is also provided a method wherein n building block oligonucleotides hybridize to at least 2 connector oligonucleotides. n can thus be 3 or 4 or 5 or 6. In other embodiments, n can be more than 6, such as 7 or 8, for example 9 or 10, such as 11 or 12, for example 13 or 14, such as 15 or 16, for example 17 or 18, such as 19 or 20, for example 21 or 22, such as 23 or 24, for example 25 or 26, such as 27 or 28, for example 29 or 30, such as 31 or 32, for example 33 or 34, such as 35 or 36, for example 37 or 38, such as 39 or 40, for example 41 or 42, such as 43 or 44, for example 45 or 46, such as 47 or 48, for example 49 or 50.

In yet another embodiment, at least n connector oligonucleotides and at least n+1 complementary connector oligonucleotides are provided, n being an integer of preferably from 3 to 6, and at least n−1 building block oligonucleotides hybridize to at least 2 connector oligonucleotides. It is also possible that n building block oligonucleotides hybridize to at least 2 connector oligonucleotides. n can thus be 3 or 4 or 5 or 6. In other embodiments, n can be more than 6, such as 7 or 8, for example 9 or 10, such as 11 or 12, for example 13 or 14, such as 15 or 16, for example 17 or 18, such as 19 or 20, for example 21 or 22, such as 23 or 24, for example 25 or 26, such as 27 or 28, for example 29 or 30, such as 31 or 32, for example 33 or 34, such as 35 or 36, for example 37 or 38, such as 39 or 40, for example 41 or 42, such as 43 or 44, for example 45 or 46, such as 47 or 48, for example 49 or 50. There is also provided a method wherein n building block oligonucleotides hybridize to at least 2 connector oligonucleotides.

In a still further embodiment, at least n connector oligonucleotides and at least n+2 complementary connector oligonucleotides are provided, n being an integer of preferably from 3 to 6, and at least n−1 building block oligonucleotides hybridize to at least 2 connector oligonucleotides. It is also possible for n building block oligonucleotides to hybridize to at least 2 connector oligonucleotides. n can thus be 3 or 4 or 5 or 6. In other embodiments, n can be more than 6, such as 7 or 8, for example 9 or 10, such as 11 or 12, for example 13 or 14, such as 15 or 16, for example 17 or 18, such as 19 or 20, for example 21 or 22, such as 23 or 24, for example 25 or 26, such as 27 or 28, for example 29 or 30, such as 31 or 32, for example 33 or 34, such as 35 or 36, for example 37 or 38, such as 39 or 40, for example 41 or 42, such as 43 or 44, for example 45 or 46, such as 47 or 48, for example 49 or 50.

In yet another embodiment, at least n connector oligonucleotides and at least n+3 complementary connector oligonucleotides are provided, n being an integer of preferably from 3 to 6, and at least n−1 building block oligonucleotides hybridize to at least 2 connector oligonucleotides. It is also possible for n building block oligonucleotides to hybridize to at least 2 connector oligonucleotides. n can thus be 3 or 4 or 5 or 6. In other embodiments, n can be more than 6, such as 7 or 8, for example 9 or 10, such as 11 or 12, for example 13 or 14, such as 15 or 16, for example 17 or 18, such as 19 or 20, for example 21 or 22, such as 23 or 24, for example 25 or 26, such as 27 or 28, for example 29 or 30, such as 31 or 32, for example 33 or 34, such as 35 or 36, for example 37 or 38, such as 39 or 40, for example 41 or 42, such as 43 or 44, for example 45 or 46, such as 47 or 48, for example 49 or 50.

In a further embodiment at least n connector oligonucleotides and at least n+4 complementary connector oligonucleotides are provided, n being an integer of from preferably 3 to 6, and at least n−1 building block oligonucleotides hybridize to at least 2 connector oligonucleotides. It is also possible for n building block oligonucleotides to hybridize to at least 2 connector oligonucleotides. n can thus be 3 or 4 or 5 or 6. In other embodiments, n can be more than 6, such as 7 or 8, for example 9 or 10, such as 11 or 12, for example 13 or 14, such as 15 or 16, for example 17 or 18, such as 19 or 20, for example 21 or 22, such as 23 or 24, for example 25 or 26, such as 27 or 28, for example 29 or 30, such as 31 or 32, for example 33 or 34, such as 35 or 36, for example 37 or 38, such as 39 or 40, for example 41 or 42, such as 43 or 44, for example 45 or 46, such as 47 or 48, for example 49 or 50.

In still further embodiments, there are provided methods wherein n connector oligonucleotides and at least n+5, such as at least n+6, for example n+7, such as at least n+8, for example n+9, such as at least n+10, for example n+11, such as at least n+12, for example at least n+13, such as n+14, for example at least n+15, such as n+16, for example at least n+17, such as n+18, for example at least n+19, such as n+20, for example at least n+21, such as at least n+22, for example n+23, such as at least n+24, for example n+25 complementary connector oligonucleotides are provided, n being an integer of preferably from 3 to 6, and at least n−1 or n building block oligonucleotides hybridize to at least 2 connector oligonucleotides. n can also be more than 6, such as e.g. such as 7 or 8, for example 9 or 10, such as 11 or 12, for example 13 or 14, such as 15 or 16, for example 17 or 18, such as 19 or 20, for example 21 or 22, such as 23 or 24, for example 25 or 26, such as 27 or 28, for example 29 or 30, such as 31 or 32, for example 33 or 34, such as 35 or 36, for example 37 or 38, such as 39 or 40, for example 41 or 42, such as 43 or 44, for example 45 or 46, such as 47 or 48, for example 49 or 50.

In all of the above-mentioned methods it is furthermore possible for any plurality of building block oligonucleotides to hybridise to a single connector oligonucleotide of a supramolecular complex. Any plurality can be e.g., but not limited to, 2 or 3, for example 4 or 5 or 6, such as 7 or 8, for example 9 or 10, such as 11 or 12, for example 13 or 14, such as 15 or 16, for example 17 or 18, such as 19 or 20, for example 21 or 22, such as 23 or 24, for example 25 or 26, such as 27 or 28, for example 29 or 30, such as 31 or 32, for example 33 or 34, such as 35 or 36, for example 37 or 38, such as 39 or 40, for example 41 or 42, such as 43 or 44, for example 45 or 46, such as 47 or 48, for example 49 or 50.

More than one single connector oligonucleotide can be hybridized to the above plurality of building block oligonucleotides, such as 2 single connector oligonucleotides, for example 3 or 4 single connector oligonucleotides, such as 5 or 6 single connector oligonucleotides, for example 7 or 8 single connector oligonucleotides, such as 9 or 10 single connector oligonucleotides, for example 11 or 12 single connector oligonucleotides, such as 13 or 14 single connector oligonucleotides, for example 15 or 16 single connector oligonucleotides, such as 17 or 18 single connector oligonucleotides, for example 19 or 20 single connector oligonucleotides.

The plurality of connector oligonucleotides provided can comprise linear and/or branched connector oligonucleotides. In one embodiment, the plurality of connector oligonucleotides comprise at least n branched connector oligonucleotides and at least n building block oligonucleotides, n being an integer of preferably from 2 to 6, and wherein at least n−1 building block oligonucleotide hybridize to at least 2 branched connector oligonucleotides. In other embodiments there is provided at least n+1 building block oligonucleotides. Also, it is possible for at least n such as n+1 building block oligonucleotides to hybridize to at least 2 branched connector oligonucleotides. n can thus be 3 or 4 or 5 or 6. In other embodiments, n can be more than 6, such as 7 or 8, for example 9 or 10, such as 11 or 12, for example 13 or 14, such as 15 or 16, for example 17 or 18, such as 19 or 20, for example 21 or 22, such as 23 or 24, for example 25 or 26, such as 27 or 28, for example 29 or 30, such as 31 or 32, for example 33 or 34, such as 35 or 36, for example 37 or 38, such as 39 or 40, for example 41 or 42, such as 43 or 44, for example 45 or 46, such as 47 or 48, for example 49 or 50.

In one embodiment, a molecule of the invention is formed when chemical entities, or parts thereof, are transferred from donor building block oligonucleotides to an acceptor building block oligonucleotide. Accordingly, one or more reactive group(s) of at least 1 chemical entity of a building block oligonucleotide react with one or more reactive group(s) of at least 1 chemical entity of at least 1 other building block oligonucleotide. The at least 1 chemical entity preferably comprise from 1 to 6 reactive groups, such as e.g. 2 or 3 or 4 or 5 reactive groups.

In one preferred embodiment, at least 3 reactive groups of at least 1 chemical entity react with at least 1 reactive group of at least 3 other chemical entities. The molecule can ultimately be generated on an acceptor building block oligonucleotide by covalently linking chemical entities, or a part thereof, donated by one or more individual building block oligonucleotides (CCPNs (building block oligonucleotides)) each comprising at least one chemical entity, such as 2 or 3 CCPNs (building block oligonucleotides), for example 4 or 5 CCPNs (building block oligonucleotides), such as 6 or 7 CCPNs (building block oligonucleotides), for example 8 or 9 CCPNs (building block oligonucleotides), such as 10 or 11 CCPNs (building block oligonucleotides), for example 12 or 13 CCPNs (building block oligonucleotides), such as 14 or 15 CCPNs (building block oligonucleotides), for example 16 or 17 CCPNs (building block oligonucleotides), such as 18 or 19 CCPNs (building block oligonucleotides), for example 20 or 21 CCPNs (building block oligonucleotides), such as 22 or 23 CCPNs (building block oligonucleotides), for example 24 or 25 CCPNs (building block oligonucleotides).

The plurality of building block oligonucleotides preferably comprise at least 2 building block oligonucleotides (CCPNs (building block oligonucleotides)) which are non-identical, such as 10 CCPNs (building block oligonucleotides), for example 50 CCPNs (building block oligonucleotides), such as 1000 CCPNs (building block oligonucleotides), for example 10000 CCPNs (building block oligonucleotides), such as 100000 CCPNs (building block oligonucleotides) which are non-identical.

In one embodiment there is provided a method wherein said plurality of building block oligonucleotides comprise at least 2 branched building block oligonucleotides. The plurality of connector oligonucleotides preferably comprise connector oligonucleotides comprising a sequence of n nucleotides, wherein n is an integer of from 8 to preferably less than 400, such as 300, for example 200, such as 100, for example 50, such as 40, for example 30. The plurality of connector oligonucleotides can further comprise connector oligonucleotides comprising at least 1 branching point connecting at least three polynucleotide fragments comprising a sequence of n nucleotides, wherein n is an integer of from 8 to preferably less than 400, such as 300, for example 200, such as 100, for example 50, such as 40, for example 30.

In some embodiments of the invention connector oligonucleotides can be selected from the group consisting of
a) connector oligonucleotides comprising at least 1 chemical entity comprising at least 1 reactive group,
b) connector oligonucleotides comprising at least 1 reactive group,
c) connector oligonucleotides comprising at least 1 spacer region, The plurality of building block oligonucleotides can comprise oligonucleotides comprising a sequence of n nucleotides, wherein n is an integer of from 8 to preferably less than 400, such as 300, for example 200, such as 100, for example 50, such as 40, for example 30. The plurality of building block oligonucleotides can further comprise polynucleotides comprising at least 1 branching point connecting at least three polynucleotide fragments comprising a sequence of n nucleotides, wherein n is an integer of from 8 to preferably less than 400, such as 300, for example 200, such as 100, for example 50, such as 40, for example 30.

In another aspect of the invention there is provided a method for synthesising a plurality of different molecules, said method comprising the steps of performing any of the methods described herein above for each different molecule being synthesised.

Further steps in the method for synthesising a plurality of different molecules are provided herein below. One further step comprises selecting molecules—or bifunctional complexes comprising molecules—having desirable characteristics, wherein the selection employs a predetermined assaying procedure.

Another further step is amplifying at least part of the individual connector oligonucleotides used for the synthesis of a selected molecule. Yet another further step is contacting a population of said amplified connector oligonucleotides, or fragments thereof, with a plurality of building block oligonucleotides for a further round synthesis. Accordingly, it is possible to perform one or more additional synthesis rounds by carrying out the steps of the method using a population of said amplified connector oligonucleotides or a population of said amplified connector oligonucleotide fragments.

Molecules capable of being synthesised by the methods of the present invention include, but are not limited to, molecules comprising a linear sequence of chemical entities and branched molecules comprising a branched sequence of chemical entities. Molecules comprising a cyclic sequence of chemical entities can also be provided.

Yet another example of a molecule capable of being synthesised is an oligomer or a polymer comprising at least one repetitive sequence of chemical entities. In one embodiment, the sequence of at least three chemical entities is preferably repeated at least twice in the molecule, in another embodiment any sequence of at least three chemical entities in the molecule occurs only once.

Preferred molecules comprise or essentially consist of amino acids selected from the group consisting of α-amino acids, β-amino acids, γ-amino acids, ω-amino acids, natural amino acid residues, monosubstituted α-amino acids, disubstituted α-amino acids, monosubstituted β-amino acids, disubstituted β-amino acids, trisubstituted β-amino acids, and tetrasubstituted β-amino acids.

The backbone structure of said β-amino acids preferably comprises or essentially consists of a cyclohexane-backbone and/or a cyclopentane-backbone.

Other preferred classes of molecules are molecules comprising or essentially consisting of vinylogous amino acids, and molecules comprising or essentially consisting of N-substituted glycines.

Further preferred molecules comprise or essentially consist of α-peptides, β-peptides, γ-peptides, ω-peptides, mono-, di- and tri-substituted α-peptides, β-peptides, γ-peptides, ω-peptides, peptides wherein the amino acid residues are in the L-form or in the D-form, vinylogous polypeptides, glycopoly-peptides, polyamides, vinylogous sulfonamide peptide, polysulfonamide, conjugated peptides comprising e.g. prosthetic groups, polyesters, polysaccharides, polycarbamates, polycarbonates, polyureas, polypeptidylphosphonates, polyurethanes, azatides, oligo N-substituted glycines, polyethers, ethoxyformacetal oligomers, poly-thioethers, polyethylene glycols (PEG), polyethylenes, polydisulfides, polyarylene sulfides, polynucleotides, PNAs, LNAs, morpholinos, oligo pyrrolinone, polyoximes, polyimines, polyethyleneimines, polyimides, polyacetals, polyacetates, polystyrenes, polyvinyl, lipids, phospholipids, glycolipids, polycyclic compounds comprising e.g. aliphatic or aromatic cycles, including polyheterocyclic compounds, proteoglycans, and polysiloxanes, including any combination thereof.

Yet further preferred molecules comprise or essentially consist of α-peptides, β-peptides, γ-peptides, ω-peptides, mono-, di- and tri-substituted α-peptides, β-peptides, γ-peptides, ω-peptides, peptides wherein the amino acid residues are in the L-form or in the D-form, vinylogous polypeptides, glycopoly-peptides, polyamides, vinylogous sulfonamide peptides, polysulfonamides, conjugated peptides comprising e.g. prosthetic groups, polyesters, polysaccharides, polycarbamates, polycarbonates, polyureas, polypeptidylphosphonates, polyurethanes, azatides, oligo N-substituted glycines, polyethers, ethoxyformacetal oligomers, poly-thioethers, polyethylene glycols (PEG), polyethylenes, polydisulfides, polyarylene sulfides, polynucleotides, PNAs, LNAs, morpholinos, oligo pyrrolinones, polyoximes, polyimines, polyethyleneimines, polyimides, polyacetals, polyacetates, polystyrenes, polyvinyl, lipids, phospholipids, glycolipids, polycyclic compounds comprising e.g. aliphatic or aromatic cycles, including polyheterocyclic compounds, proteoglycans, and polysiloxanes, and wherein the plurality of chemical entities reacted is preferably from 2 to 200, for example from 2 to 100, such as from 2 to 80, for example from 2 to 60, such as from 2 to 40, for example from 2 to 30, such as from 2 to 20, for example from 2 to 15, such as from 2 to 10, such as from 2 to 8, for example from 2 to 6, such as from 2 to 4, for example 2, such as from 3 to 100, for example from 3 to 80, such as from 3 to 60, such as from 3 to 40, for example from 3 to 30, such as from 3 to 20, such as from 3 to 15, for example from 3 to 15, such as from 3 to 10, such as from 3 to 8, for example from 3 to 6, such as from 3 to 4, for example 3, such as from 4 to 100, for example from 4 to 80, such as from 4 to 60, such as from 4 to 40, for example from 4 to 30, such as from 4 to 20, such as from 4 to 15, for example from 4 to 10, such as from 4 to 8, such as from 4 to 6, for example 4, for example from 5 to 100, such as from 5 to 80, for example from 5 to 60, such as from 5 to 40, for example from 5 to 30, such as from 5 to 20, for example from 5 to 15, such as from 5 to 10, such as from 5 to 8, for example from 5 to 6, for example 5, such as from 6 to 100, for example from 6 to 80, such as from 6 to 60, such as from 6 to 40, for example from 6 to 30, such as from 6 to 20, such as from 6 to 15, for example from 6 to 10, such as from 6 to 8, such as 6, for example from 7 to 100, such as from 7 to 80, for example from 7 to 60, such as from 7 to 40, for example from 7 to 30, such as from 7 to 20, for example from 7 to 15, such as from 7 to 10, such as from 7 to 8, for example 7, for example from 8 to 100, such as from 8 to 80, for example from 8 to 60, such as from 8 to 40, for example from 8 to 30, such as from 8 to 20, for example from 8 to 15, such as from 8 to 10, such as 8, for example 9, for example from 10 to 100, such as from 10 to 80, for example from 10 to 60, such as from 10 to 40, for example from 10 to 30, such as from 10 to 20, for example from 10 to 15, such as from 10 to 12, such as 10, for example from 12 to 100, such as from 12 to 80, for example from 12 to 60, such as from 12 to 40, for example from 12 to 30, such as from 12 to 20, for example from 12 to 15, such as from 14 to 100, such as from 14 to 80, for example from 14 to 60, such as from 14 to 40, for example from 14 to 30, such as from 14 to 20, for example from 14 to 16, such as from 16 to 100, such as from 16 to 80, for example from 16 to 60, such as from 16 to 40, for example from 16 to 30, such as from 16 to 20, such as from 18 to 100, such as from 18 to 80, for example from 18 to 60, such as from 18 to 40, for example from 18 to 30, such as from 18 to 20, for example from 20 to 100, such as from 20 to 80, for example from 20 to 60, such as from 20 to 40, for example from 20 to 30, such as from 20 to 25, for example from 22 to 100, such as from 22 to 80, for example from 22 to 60, such as from 22 to 40, for example from 22 to 30, such as from 22 to 25, for example from 25 to 100, such as from 25 to 80, for example from 25 to 60, such as from 25 to 40, for example from 25 to 30, such as from 30 to 100, for example from 30 to 80, such as from 30 to 60, for example from 30 to 40, such as from 30 to 35, for example from 35 to 100, such as from 35 to 80, for example from 35 to 60, such as from 35 to 40, for example from 40 to 100, such as from 40 to 80, for example from 40 to 60, such as from 40 to 50, for example from 40 to 45, such as from 45 to 100, for example from 45 to 80, such as from 45 to 60, for example from 45 to 50, such as from 50 to 100, for example from 50 to 80, such as from 50 to 60, for example from 50 to 55, such as from 60 to 100, for example from 60 to 80, such as from 60 to 70, for example from 70 to 100, such as from 70 to 90, for example from 70 to 80, such as from 80 to 100, for example from 80 to 90, such as from 90 to 100.

Molecular weights of the molecules to be synthesised in accordance with the present invention are preferably "small molecules", i.e. molecules preferably having a molecular weight (MW) of less than 10000 Daltons, such as less than 8000 Daltons, for example less than 6000 Daltons, such as less than 5000 Daltons, for example less than 4000 Daltons, for example less than 3500 Daltons, such as less than 3000 Daltons, for example less than 2500 Daltons, for example less than 2000 Daltons, such as less than 1800 Daltons, for example less than 1600 Daltons, for example less than 1400 Daltons, such as less than 1200 Daltons, for example less than 1000 Daltons.

The chemical entities of the above molecules can in one embodiment be linked by a chemical bond selected from the group of chemical bonds consisting of peptide bonds, sulfonamide bonds, ester bonds, saccharide bonds, carbamate bonds, carbonate bonds, urea bonds, phosphonate bonds, urethane bonds, azatide bonds, peptoid bonds, ether bonds, ethoxy bonds, thioether bonds, single carbon bonds, double carbon bonds, triple carbon bonds, disulfide bonds, sulfide bonds, phosphodiester bonds, oxime bonds, imine bonds, imide bonds, including any combination thereof.

In one embodiment the chemical bond linking at least some of the chemical entities of the molecule is preferably formed by a reaction of a nucleophile group of a first chemical entity with an ester or thioester of another chemical entity. The linker of the chemical entity bearing the thioester group is preferably cleaved simultaneously with the formation of the bond resulting in a transfer of the chemical entity or a part thereof to the nucleophilic chemical entity. The nucleophile group is preferably selected from —$NH_2$, $H_2$NHN—, HOHN—, $H_2$N—C(O)—NH—.

The backbone structure of a molecule synthesised by the methods of the present invention can comprises or essentially consists of one or more molecular group(s) selected from —NHN(R)CO—; —NHB(R)CO—; —NHC(RR')CO—; —NHC(=CHR)CO—; —$NHC_6H_4$CO—; —$NHCH_2$CHRCO—; —NHCHR$CH_2$CO—; —$COCH_2$—; —COS—; —CONR—; —COO—; —CSNH—; —$CH_2$NH—; —$CH_2CH_2$—; —$CH_2$S—; —$CH_2$SO—; —$CH_2SO_2$—; —CH($CH_3$)S—; —CH=CH—; —NHCO—; —NHCONH—; —CONHO—; —C(=$CH_2$)$CH_2$—; —$PO_2^-$NH—; —$PO_2^-CH_2$—; —$PO_2^-CH_2N^+$—; —$SO_2NH^-$—; and lactams.

In accordance with the present invention it is possible to generate a composition comprising a plurality of more than or about $10^3$ different molecules, such as more than or about $10^4$ different molecules, for example more than or about $10^5$ different molecules, such as more than or about $10^6$ different molecules, for example more than or about $10^7$ different molecules, such as more than or about $10^8$ different molecules, for example more than or about $10^9$ different molecules, such as more than or about $10^{10}$ different molecules, for example more than or about $10^{11}$ different molecules, such as more than or about $10^{12}$ different molecules, for example more than or about $10^{13}$ different molecules, such as more than or about $10^{14}$ different molecules, for example more than or about $10^{15}$ different molecules, such as more than or about $10^{16}$ different molecules, for example more than or about $10^{17}$ different molecules, such as more than or about $10^{18}$ different molecules.

The molecules can be targeted to a potential binding partner while still bound to the identifier polynucleotide of the bifunctional complex, or the molecules can be cleaved from the identifier polynucleotide to which they are bound following their synthesis. When targeted to a potential binding partner, the present invention also pertains to bifunctional complexes further comprising a binding partner having an affinity for the molecule of the bifunctional complex. Such binding partners can be e.g. any molecule including molecules selected from the group consisting of DNA, RNA, antibody, peptide, or protein, or derivatives thereof.

The below sections describe in further detail selected embodiments and different modes for carrying out the present invention. Focus is on the formation of hybridisation complexes formed between a plurality of building blocks (one or more chemical entities linked to an oligonucleotide), also termed CCPN's, and one or more connector polynucleotides, also termed CPN's (at least some of which are capable of hybridising to two or more building blocks, thereby bringing building block chemical entities into reactive proximity). Once the hybridisation complex has been allowed to form, the building blocks (CCPN's) are ligated, enzymatically, chemically or otherwise, separated from optionally ligated connector building blocks, and the chemical entities linked to the oligonucleotide of individual building blocks are reacted, preferably in the absence of hybridisation between building block oligonucleotides and connector oligonucleotides. The separation can be a disruption of the hydrogen bonds of the hybridisation complex, or the separation can be a physical separation into different reaction compartments. Physical separation can exploit the linkage of an affinity pair member to the identifier polynucleotide formed when ligating the building block oligonucleotides.

The methods of the present invention allow molecules to be formed through the reaction of a plurality of reactants or chemical entities, such as e.g. reactions involving the formation of bonds between chemical entities i.e. chemical moieties, by the reaction of chemical entity reactive groups. The present invention describes the use of connector oligonucleotides (CPN's) to bring chemical entities linked to identifier oligonucleotides of building blocks (CCPN's) in reactive proximity, whereby such bond formations are made possible, leading to the synthesis of molecules such as e.g. small molecules and polymers.

In the present invention, the individual chemical moieties/chemical entities may be carried by oligonucleotides (CCPN's) capable of annealing to said CPN's. The combination and reaction of chemical entity reactive groups carried by such complementary connectors polynucleotides, will lead to formation of molecules via an initial complexation to CPN's.

Each CPN may bring two or more CCPN's in proximity, whereby reactions between functional groups on these CCPN's are made more likely to occur once the CCPn's have been ligated and separated from the CPN's.

Some CCPN's only anneal to one CPN, other CCPN's may anneal to two or more CPN's. In one embodiment of the present invention, a CCPN anneals to a CPN, which CPN allows the annealing of one further CCPN. This second CCPN may then allow the annealing of a second CPN, which may allow annealing of further CCPN's and so forth. Hybridization of multiple CCPN's and CPN's may be either sequentially or simultaneously in either one or multiple tubes. As such all CCPN's and CPN's may be added at once. Alternatively, they may be added sequentially, i.e. e.g. first a set of CPN's, then a set of CCPN's followed by a new set of CPN's or visa versa. In this sequential setting a handling control of CCPN/CPN-complex self-assembly is achieved. Again, chemical entities are reacted only after the CCPN's have been ligated and separated from optionally ligated CPN's.

In another embodiment, a set of CCPN's forms complexes $A^1$-$A''$ with a set of CPN's in one separate compartment e.g. a tube. In other compartments, other sets of CCPN's forms complexes $B^1$-$B''$ with a set of CPN's etc. These separately formed complexes may be combined and form further new complexes, either directly or through further addition of CCPN's or CPN's. This illustrates still another way of a handling control of CCPN/CPN-complex self-assembly. The complexes may also be brought into reactive proximity with bifunctional complexes made in accordance with the present invention, or the identifier polynucleotide of a bifunctional complex can be used for the generation of further hybridisation complexes.

The present invention may be used in the formation of a library of compounds. Each member of the library is assembled by the use of a number of CCPN's, which number may be the same or different for different molecules. This will allow the formation of a mixed library of molecules assembled from 2 to n chemical moieties/fragments/chemical entities or parts thereof. If such a library, e.g. contains molecules assembled from 1-7 chemical entities/chemical moieties and 100 different chemical entity/moiety types exists, the library would theoretically be a mixture of more than $100^7$ molecules.

In one setting, a CCPN may specify for the annealing of a specific type of CPN, a CPN which will specify the annealing of a further specific second CCPN, which chemical entity reactive groups are capable of reacting with the chemical entity reactive groups of CCPN one. In this setting each CCPN will therefore specify, which CCPN it interacts with via the CPN sequence, i.e. which reaction partner(s) they accept/prefer.

Some CCPN's carrying scaffolds may contain a certain set of functional groups. Other CCPN's carry scaffolds with another set of functional groups and still, each scaffold carrying CCPN may be combined with other CCPN's, which chemical entity reactive groups can react with exactly that scaffold in the presence of a number of other types of CCPN's, including e.g. CCPN's which could have reacted but were not allowed to react. Further details are described below. This control of correct/accepted combinations of chemical entity reactive groups will allow the formation of a mixed library of highly branched, semi-branched and linear molecules.

The CCPN cross talk may also be used to control the properties of library members. E.g. CCPN's carrying large chemical entities may only call for CCPN's carrying small chemical entities or CCPN's carrying hydrophilic entities may call for CCPN's carrying hydrophilic chemical entities or lipophilic chemical entities depending on design.

As the chemistries applicable, will be increased by the fact, that CCPN's themselves ensure correct/accepted chemical entity reaction partners, a much higher number of scaffolds will become easily available and may co-exist. E.g., it may be that derivatization of one scaffold can only be performed through the use of one specific set of transformation, whereas another scaffold may need another set of transformations. Different reactions and different CCPN's will therefore be needed for derivatization of each of these scaffolds. This is made possible by the present invention.

As the total number of theoretically synthesizable molecules may exceed the number of actually synthesized molecules, which can be present in a given tube, shuffling becomes important to ensure a maximum of tested CCPN combinations. If e.g. $10^{17}$ is considered as a potential maximum number of different molecules present in a given reaction tube, then by using 1,000 different CCPN's and allowing formation of molecules assembled from the chemical entities of 6 CCPN's, this number will be exceeded. Selection ensures that appropriate CPN's will survive, and shuffling will ensure that the number of combinations tested will be maximized.

In one embodiment of the present invention, a CPN-sequence is designed so as to anneal to one specific CCPN-sequence. This gives a one-to-one relationship between the chemical entity descriptor (e.g. a polynucleotide based codon) and encoded chemical entity. However, the same effect, a specific chemical entity is encoded by specific CPNs (connector oligonucleotides) and CCPNs (building block oligonucleotides), can be obtained by having a set of CPN-sequences that anneal to a set of CCPN-sequences. This would then require that identical chemical entities are carried by all the CPNs (connector oligonucleotides) or CCPNs (building block oligonucleotides) of a set.

This kind of "codon-randomization" is sometimes advantageous, for example when CPN-sequences and CCPN-sequences are designed so as to allow an expansion of the library size at a later stage. If the coding region of e.g. a CPN is 3 nucleotides (providing 64 different codons), but only 16 different chemical entities have been prepared, then the CCPNs (building block oligonucleotides) may be grouped into 16 groups, for example where the first of the three nucleotide positions is randomized (i.e. 4 different CCPN-sequences carry the same functional entity). A pseudo-one-to-one relationship is thus preserved, since the identity of the encoded chemical entity can be unambiguously identified by identification of the CPN (or CCPN) involved.

Sometimes scrambling, i.e. one CPN or CCPN sequence specifying more than one chemical entity, is advantageous. Likewise, under certain conditions it is advantageous to have one CPN or CCPN specify more than one chemical entity. This will, however, not lead to a one-to-one or a pseudo-one-to-one relationship. But may be advantageous, for example in cases where the recovered (isolated) entity from a selection can be identified through characterization of for example its mass (rather than its attached polynucleotide complex), as this will sample a larger chemistry space.

The present invention may use short oligonucleotides, which are easily available in high purity.

In the assembly of a hybridisation complex, individual CCPN's are brought into reactive proximity by one or more CPN's. The functional group composition of each chemical entity on the CCPN, determines the shape of the final molecule. Highly branched molecules may as such be assembled by transfer (or cross linkage followed by (linker) cleavage) of chemical entities from multiple mono-functionalized chemical entities (i.e. comprising one function entity reactive group) of CCPN's (e.g. substituent like) to multi-functionalized chemical entities (i.e. comprising multiple chemical entity reactive groups) of CCPN's (e.g. scaffolds/anchor like).

Linear molecules on the other hand, demands that the chemical entity of the anchor/scaffold like CCPN contains less activated functionalization (i.e. fewer chemical entity reactive groups), and furthermore that the chemical entity reactive groups of substituent like CCPN's reacts with each other.

However, in the formation of a library which both contains a mixture of highly branched, less branched and linear molecules, it is important to control, that the number and type of functional groups capable of reacting with each other match. The use of a plurality of CPN's solves this issue, by allowing only specific combinations of CCPN's in the encoding of each molecule. Each CPN thereby ensures a specific match between the number and type of needed reactions. (See FIG. 9).

The exact position of domain types may be varied as appropriate.

In the formation of a hybridisation complex, a plurality of CPN's is used. In the generation of a library of molecules, each molecule will be assembled through the use of individual combinations of CPN's. A library of molecules may be prepared as individually separated compounds or as a mixture of compounds. Each set of CPN's will contain variable polynucleotide regions in the domains for the descriptors for R-groups, and each of these variable polynucleotide regions may be combined with different combinations of CCPN annealing capabilities. Similarly, CCPN's may, in their hybridizing domains, specify/signal the need for specific reaction partners.

Similarly, CCPN's may, in their hybridizing domains, specify/signal the need for specific reaction partners. (See FIG. 10).

The invention is illustrated by the following example: An anchor/scaffold CCPN carries e.g. two functional groups X and Y in the chemical entity. It therefore signals the call for X and Y partners. The first substituent like CCPN carries only a functional group X and answers by signaling this, as it furthermore calls for a substituent like CCPN carrying chemical entity reactive group Y. These "calls/answers" are mediated via the CPN, without which these two CCPN's would not be brought in proximity and allowed to react.

The second substituent like CCPN answers the call for a chemical entity reactive group Y, but since this CCPN also carries a chemical entity reactive group Z, it calls for that. The third substituent like CCPN answers the call for a chemical entity reactive group Z, but does not call for further CCPN's. A terminator CPN may optionally anneal to the fourth complementary connector. As can be seen, the answer signal may optionally also contains information about, what exactly this CCPN further calls for. In other words, the call signal may be answered by the availability of chemical entity reactive groups as well as the one which are further called for.

Once a desirable hybridisation complex has been formed, the CCPN's are ligated and separated from optionally ligated CPN's, and the chemical entities are reacted.

The CPN's may be amplified at some step in the process or optionally be ligated to yield a one length polynucleotide, which may also be amplified and optionally further manipulated.

The following section describes how hybridization regions may be designed for CCPN's and CPN's. Each region may specify, the needed types/numbers of reaction partners.

The following simple example illustrates one design. Two different scaffold like CCPN's A and B demands different types of chemical entity reaction group chemistries.

A.

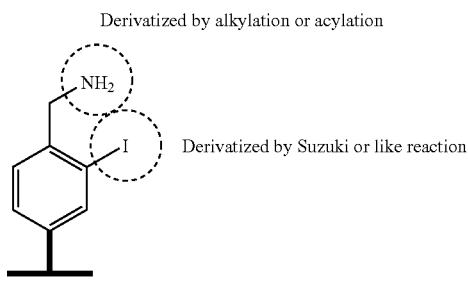

B.

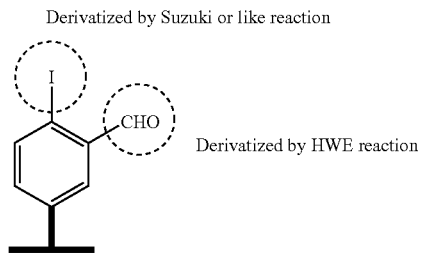

They are then to be combined with a set of substituent like CCPN's as illustrated e.g. C1-C7.

C.

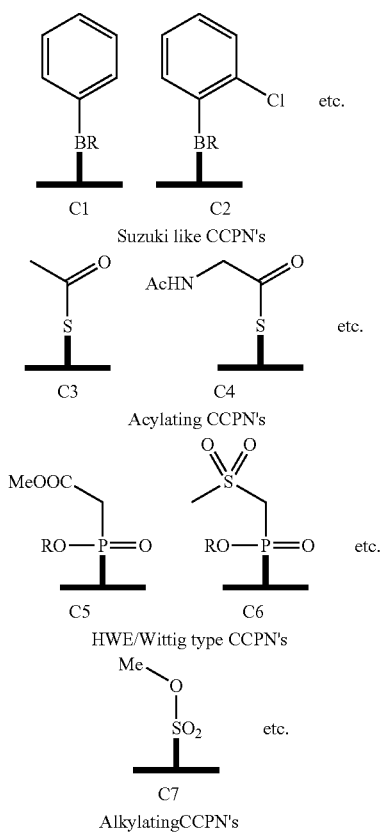

In the very simple setting, the scaffold like CCPN's calls for all the substituents needed, where such substituents are hybridized to e.g. the same CPN, i.e. only two CPN's are used. The four synthesized molecules below illustrate some of the products found in the library.

Although the corresponding connector oligonucleotides are also illustrated, the reactions of the chemical entities take place in the absence of hybridization between building block oligonucleotides and connector oligonucleotides.

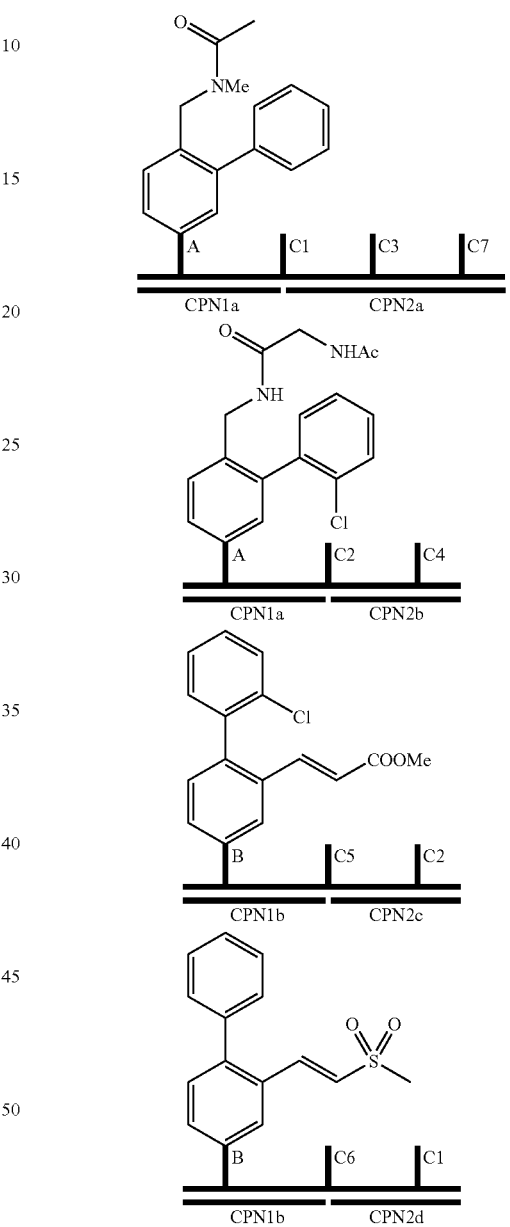

CPN type 1a anneals the scaffold type A and calls for (can only combine with) CCPN's carrying chemical entity reactive groups capable of undergoing acylation and/or alkylation and furthermore a CCPN carrying chemical entity reactive groups capable of undergoing a Suzuki reaction. This ensures e.g. that CCPN's carrying chemical entity reactive groups capable of undergoing e.g. HWE reaction will not be combined with scaffold like CCPN type A.

CPN type 2a carries three CCPN's with chemical entity reactive groups capable of undergoing acylation, alkylation and Suzuki type reactions.

CPN type 2b carries only two CCPN's with chemical entity reactive groups capable of undergoing acylation and Suzuki type reactions.

CPN type 2a thereby allows further branching, whereas CPN type 2b does not.

CPN type 1b anneals the scaffold type B and calls for (can only combine with) CCPN's carrying chemical entity reactive groups capable of undergoing HWE/Wittig reaction and furthermore a CCPN carrying chemical entity reactive groups capable of undergoing a Suzuki reaction. This ensures e.g. that CCPN's carrying chemical entity reactive groups capable of undergoing e.g. acylation reaction will not be combined with scaffold like CCPN type B.

If all four bases are used in the variable regions of CCPN's a total and e.g. 256 different scaffolds type A, 256 different scaffolds type B, 256 different acylating CCPN's, 256 different alkylating CCPN's, 256 Suzuki type CCPN's and 256 different HWE/Wittig type CCPN's could be used. The following sequences for polynucleotide sequences could be one design to illustrate the principle (wherein N denotes a random nucleobase, preferably selected from G, A, C, T, U):

Scaffold like CCPN's type A's: 3'-GCGCNNNNGGCG-5' (SEQ ID NO: 1).

One specific scaffold e.g. the one illustrated above could e.g. have the specific sequence: 3'-GCGCATTAGGCG-5' (SEQ ID NO:2).

Another scaffold type A, demanding the same chemistries but having another skeleton could have the specific sequence: 3'-GCGCTTAAGGCG-5' etc. (SEQ ID NO:3).

Scaffold like CCPN's type B's 3'-AATTNNNNTAAT-5' (SEQ ID NO:4).

One specific scaffold e.g. the one illustrated above could e.g. have the specific sequence: 3'-AATTGCCGTAAT-5' (SEQ ID NO:5).

Another scaffold type A, demanding the same chemistries but having another skeleton could have the specific sequence: 3'-AATTCGGGTAAT-5' etc. (SEQ ID NO:6).

Suzuki type CCPN's 3'-TTTTTGAGANNNNAAG-GTTTTT-5' (SEQ ID NO:7).

One specific Suzuki type CCPN e.g. C1 illustrated above could e.g. have the specific sequence: 3'-TTTTTGAGATTC-CAAGGTTTTT-5' (SEQ ID NO:8). Another Suzuki type CCPN could e.g. have the sequence 3'-TTTTTGAGACT-TCAAGGTTTTT-5' (SEQ ID NO:9).

```
Acylation type CCPN's:
3'-GTTGNNNNTTGG-5'            (SEQ ID NO:10)

Alkylation type CCPN's:
3'-AACCNNNNACCA-5'            (SEQ ID NO:11)

HWE/Wittig type CCPN's:
3'-TTCCNNNNCTCT-5'            (SEQ ID NO:12)

CPN type 1a sequences:
3'-NNNNTCTCAAAAACGCCNNNNGCGC-5'   (SEQ ID NO:13)
```

One specific type of these would be

```
3'-GGAATCTCAAAAACGCCTAATGCGC-5'   (SEQ ID NO:14)
``` this CPN would allow the hybridization of CCPN type A and CCPN type C1. Another specific sequence would allow the hybridization of e.g. C2 instead of C1 but not C3-C7 etc.

In some settings single stranded regions may be applied to increase flexibility of the complex. This may be implemented by increasing e.g. the number of A nucleobases from 5 nucleobases to 7 or 10 or what is found appropriate.

```
CPN type 2a sequences:            (SEQ ID NO:15)
3'-TGGTNNNNGGTTCCAANNNNCAACAAAAACCTT-5'

CPN type 2b sequences:            (SEQ ID NO:16)
3'-CCAANNNNCAACAAAAACCTT-5'.
```

Sequences for CPN type 1b, 2c and 2d are designed similarly to allow hybridization of CCPN's carrying chemical entity reactive groups capable of undergoing HWE reactions rather than acylating and/or alkylating reactions.

If the number of potential combination is to be maximally increased a high number of CPN's may be used and each CCPN may then make use of "cross talk".

In such a setting, the reactions used may be 1. acylations (Ac), 2. alkylations (Al) 3. Cross coupling/Suzuki and like reactions (C) and 4. HWE/Wittig type reactions (W).

Following "cross talk" between CPN's and CCPN's, the CCPN's are ligated and separated from optionally ligated CPN's as described herein elsewhere. Following separation of a) the identifier polynucleotide generated by ligation of the oligonucleotide parts of the CCPN's, and b) optionally ligated CPN's, the chemical entities of the CCPN's are reacted (i.e. at a point in time where CPN's and CCPN's of a hybridisation complex no longer hybridise).

Each chemical entity reaction demands a donor and an acceptor. Donor denotes a chemical entity reactive group, which upon reaction leads to transfer of the chemical entity or a part thereof of that CCPN. Transfer may be directly in one step or sequentially through cross linkage followed by cleavage. An acceptor denotes a chemical entity reactive group, which upon reaction accepts the transfer of a chemical entity or part thereof from another CCPN.

When designing CCPN hybridization regions, one may bias the library towards specific properties, e.g. if selection is used to identify drug candidates in the library, it is in most cases not appropriate to have aromatic amines presented due to their potential toxic properties, whereas aliphatic amines are in general acceptable. CCPN's carrying aromatic amines may therefore specifically signal the need to be partnered, with a CCPN carrying a chemical entity reactive group capable of undergoing acylation reactions and optionally allow a CCPN carrying a chemical entity reactive group capable of undergoing alkylating reactions, whereas aliphatic amines may be partnered with both CCPN's carrying chemical entity reactive groups capable of undergoing acylation and alkylation reactions. Aromatic hydroxyl groups, on the other hand, should not be acylated due to the generation of another acylating specie, which will generally not be acceptable as drug candidate. Aromatic hydroxyl groups should therefore only be alkylated. Such demands may be entered into hybridization region for a specific CCPN.

If all four reaction types were to be used in one library generation, then the hybridization region of each CCPN could specify, which one of the reaction types, mentioned above, are needed (denoted by "*"), allowed (denoted by "+") and forbidden (denoted by "–").

Plus ("+") sequences may be composed of non-specific hybridizing nucleobases such as e.g. inosine. Minus ("–") sequences may be composed of a nucleobase sequence with one specific sequence and the need of a specific partner will be specified by another specific sequence.

E.g. nucleobase sequence I (inosine)="+"; nucleobase sequence T (thymine)="–", and nucleobase sequence G (guanine)="*".

| | "+": Allowed reactive group on CCPN's further downstream | "–": Disallowed reactive group on CCPN's further downstream | "*": Needed reactive group on CCPN's further downstream |
|---|---|---|---|
| CCPN sequence | I | T | G |
| CPN sequence accepted | A or C | A | C |

As the need, acceptance or disallowance of e.g. four different reaction partners is to be signaled, the overall descriptor sequence for type and number of chemical entities on a CCPN corresponds to four polynucleotide sub-regions. In the following illustrations, the regions 1, 2, 3, 4 correspond to the need or acceptance of the partners Ac (1); Al (2); C (3) and W (4). One further nucleobase in that polynucleotide sub-region may optionally indicate whether the chemical entity reactive group is of donor or acceptor type. In the following nucleobase T (thymine) indicates a donor, nucleobase G (guanine) indicates an acceptor and nucleobase I (inosine) is used if donor/acceptor type is not specified.

In the design example above, the four regions 1 (Acylation), 2 (Alkylation), 3 (Cross Coupling/Suzuki) and 4 (Wittig/HWE) could be of a total of 8 nucleobases for the call region and 8 nucleobases for the answer region.

One simpler example, using a higher number of CPN's could be the following example. In this example, the call signal specifies only the need/allowed CCPN's and the answer similarly.

The CCPN's in a peptide like library composed of complementary connectors 1-7 could have the identifier polynucleotide sequences shown in FIG. 11.

CCPN1 and CCPN2 carries only a call region and calls for acylating acceptors. CCPN3-CCPN5 carries both an answer and a call region. The answer region specifies that it needs an acylating donor but also allows alkylating agents. The call region specifies the call for an acylating acceptor.

CCPN6 and CCPN7 carries only an answer region. The answer region specifies that it needs an acylating donor but also allows alkylating donors.

To generate this library, the following CPN may then fulfill the need:

```
                                            (SEQ ID NO:24)
CPN1:       3'-NN-CACAACAC-CACACACC-NN-5'
```

Where N denotes a variable nucleobase.

In this library all CCPN's carrying function entity groups of amino type have been specified as allowance for alkylation, but with the need for acylation.

In order to control the degree of supramolecular complex formation, terminator sequences may be added at some point in time. The concentration of which, will determine the mean distribution of how many CCPN's and CPN each complex is made of.

Such terminator sequences could in the example above be:

```
                                            (SEQ ID NO:25)
Terminator1:        3'-CACACACC-NN-5'

(SEQ ID NO:26)
Terminator2:        3'-GTITTITI-NN-5'
```

The above methods involve the formation of a hybridisation complex comprising hybridised CPN's and CCPN's.

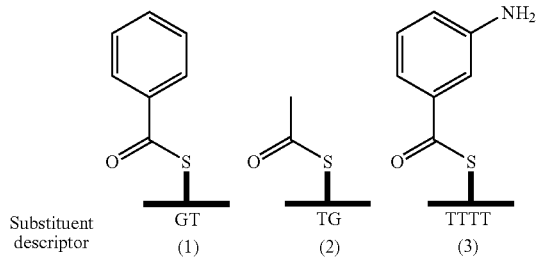

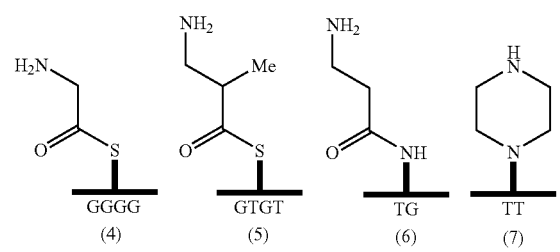

The sequence of the building block oligonucleotides could then be:

```
                                    (SEQ ID NO:17)
CCPN1:      3'-GT-GGTITITI-5'

(SEQ ID NO:18)
CCPN2:      3'-TG-GGTITITI-5'

(SEQ ID NO:19)
CCPN3:      3'-GTITTITI-TTTT-GGTITITI-5'

(SEQ ID NO:20)
CCPN4:      3'-GTITTITI-GGGG-GGTITITI-5'

(SEQ ID NO:21)
CCPN5:      3'-GTITTITI-GTGT-GGTITITI-5'

(SEQ ID NO:22)
CCPN6:      3'-GTITTITI-TG-5'

(SEQ ID NO:23)
CCPN7:      3'-GTITTITI-TT-5'
```

Following the formation of the hybridisation complex, the oligonucleotides of the CCPN's are ligated, enzymatically, chemically, or otherwise, and separated from optionally ligated CPN's. The aforementioned steps occur before chemical entities carried by CCPN's are reacted. Reaction of the chemical entities result in the formation of a bifunctional complex.

Bifunctional Complex

The bifunctional complexes of the present invention comprises a molecule and an identifier polynucleotide. The identifier polynucleotide comprises identifying moieties that identifies the molecule. In some embodiments, the identifier polynucleotide identifies the molecule uniquely, i.e. in a library of complexes a particular identifier polynucleotide is capable of distinguishing the molecule it is attached to from the rest of the molecules.

The molecule and the identifier polynucleotide may be attached directly to each other or through a bridging moiety. In one aspect of the invention, the bridging moiety is a selectively cleavable linkage (non-limiting examples disclosed in detail herein below).

The identifying moieties of each complex suitably comprise recognition units, i.e. units which may be recognized by a detecting entity. A variety of different kinds of recognition exist in nature. Examples include antibodies which recognize an epitope, proteins which recognize another protein, nucleic acids including mRNA which recognize a protein, small molecules (like biotin) which recognize a protein (like avidine or streptavidine) and oligonucleotides which recognizes complementing oligonucleotides. It is preferred that the identifier polynucleotide is a sequence of nucleotides.

The method may in certain embodiments be performed without amplification after a separation or partitioning step. However, when larger libraries are used and the amount of separated identifier polynucleotides is relatively low, it is in general preferred to use an identifier polynucleotide which is amplifiable. Identifier polynucleotides comprising a sequence of nucleotides may be amplified using standard techniques, like PCR.

In the event that an identifier polypeptide and not an identifier polynucleotide is used, the polypeptide may be amplified by attaching the mRNA which encoded the synthesis thereof, generating the cDNA from the mRNA and subjecting said mRNA to a translation system. Such system is described in WO 98/31700 the content of which is incorporated herein by reference. An alternative method for amplifying a protein is to use phage-displayed proteins.

The identifier polynucleotide may comprise two or more oligonucleotides originating from different building blocks. The sequences of the oligonucleotides can be decoded to identify the chemical entities used in the formation of the molecule. In certain embodiments, when the identifier polynucleotide comprises more than one oligonucleotide, each member of a pool of building blocks can be identified uniquely and the order of oligonucleotides is informative of the synthesis step each member has been incorporated in.

The number of individual nucleotides making up each oligonucleotide can be anything suitable. In some embodiments of the invention, it is preferred that each oligonucleotide independently comprises four or more nucleotides, more preferred from 4 to 30 nucleotides.

The identifier polynucleotide will in general have at least two oligonucleotides arranged next to each other. Any two neighbouring oligonucleotides may be separated by a framing sequence. Depending on the molecule formed, the identifier polynucleotide may comprise further oligonucleotides, such as 3, 4, 5, or more oligonucleotides. Each of the further oligonucleotides may be separated by a suitable framing sequence. In some embodiments, all or at least a majority of the oligonucleotides of the identifier polynucleotide are separated from a neighbouring oligonucleotide by a framing sequence. The framing sequence may have any suitable number of nucleotides, e.g. 1 to 20. Alternatively, oligonucleotides on the identifier polynucleotide may be designed with overlapping sequences.

The framing sequence, if present, may serve various purposes. In one setup of the invention, a given framing sequence identifies the position of an oligonucleotide in an identifier polynucleotide. Usually, the framing sequence either upstream or downstream of an oligonucleotide comprises information which allows determination of the position of the oligonucleotide in the identifier polynucleotide. In another setup, the frames have alternating sequences, allowing for hybridisation of building blocks from two pools in the formation of the library.

The framing sequence may also or in addition provide for a region of high affinity. The high affinity region may ensure that the hybridisation of connector oligonucleotides and building block oligonucleotides occurs in frame. Moreover, the framing sequence may adjust the annealing temperature to a desired level.

A framing sequence with high affinity can be provided by incorporation of one or more nucleobases forming three hydrogen bonds to a cognate nucleobase. Examples of nucleobases having this property are guanine and cytosine. Alternatively, or in addition, the framing sequence may be subjected to backbone modification. Several back bone modifications provides for higher affinity, such as 2'-O-methyl substitution of the ribose moiety, peptide nucleic acids (PNA), and 2'-4' O-methylene cyclisation of the ribose moiety, also referred to as LNA (Locked Nucleic Acid).

The identifier polynucleotide may also comprise flanking regions. The flanking regions can encompass a signal group, such as a fluorophor or a radioactive group to allow for detection of the presence or absence of a complex, or the flanking region may comprise a label that may be detected, such as biotin. When the identifier polynucleotide comprises a biotin moiety, the identifier polynucleotide may easily be recovered following the separation step.

The flanking regions can also serve as priming sites for amplification reactions, such as PCR. The identifier polynucleotide may in certain embodiments comprise an affinity region having the property of being able to hybridise to a building block.

The molecule part of the complex is generally of a structure expected of having an effect on the target. When the target is of pharmaceutical importance, the molecule is generally a drug candidate. The complex can e.g. be formed by tagging a library of different possible drug candidates with a tag, e.g. a nucleic acid tag uniquely identifying each possible drug candidate.

In another embodiment of the invention, the molecule is formed by a variety of chemical entities which have reacted with each other and/or a scaffold molecule. Optionally, this reaction product may be post-modified to obtain the final molecule displayed on the complex. The post-modification may involve the cleavage of one or more chemical bonds attaching the molecule to the identifier in order to more efficiently display the molecule.

The formation of an molecule can involve a scaffold, i.e. a chemical unit having one or more reactive groups capable of forming a connection to another reactive group positioned on a chemical entity, thereby generating an addition to the original scaffold. A second chemical entity may react with a reactive group also appearing on the original scaffold or a reactive group incorporated by the first chemical entity. Further chemical entities may be involved in the formation of the final reaction product. The formation of a connection between the chemical entity and the nascent molecule may be mediated by a bridging molecule. As an example, if the nascent molecule and the chemical entity both comprise an amine group a connection between these can be mediated by a dicarboxylic acid. A molecule is in general produced in vitro and may be a naturally occurring or an artificial substance. A molecule is not produced using the naturally translation system in an in vitro process.

The chemical entities that are precursors for structural additions or eliminations of the molecule are attached to a building block prior to the participation in the formation of the reaction product leading to the final molecule. Besides the chemical entity, the building block comprises an identifier oligonucleotide capable of identifying the chemical entity. In some embodiments the building blocks also comprise an affinity region providing for affinity towards the nascent complex.

The chemical entities are preferably reacted without enzymatic interaction in some aspects of the invention. Notably, the reaction of the chemical entities is preferably not mediated by ribosomes or enzymes having similar activity.

The chemical entity of the building block can in some embodiments be regarded as precursors for the structural entity eventually incorporated into the molecule. In other cases a chemical entity provides for the elimination of one or more chemical units from a nascent (i.e. intermediate) molecule—prior to the formation of a final molecule.

When it is stated herein that a chemical entity is "transferred" to a molecule precursor it shall be understood that not necessarily all the atoms of the original chemical entity is to be found in the molecule or molecule precursor. Also, as a consequence of the reactions involved in the formation of a molecule, the structure of a chemical entity can be changed when it forms part of a molecule or molecule precursor. Especially, a cleavage resulting in the release of a chemical entity may generate a reactive group which in a subsequent step can participate in the formation of a bond between the molecule or molecule precursor and another chemical entity. A chemical entity of a molecule precursor can thus in some embodiments serve as a protection group.

The chemical entity of a building block comprises at least one reactive group capable of participating in a reaction which results in a connection between the chemical entity of the building block and another chemical entity, or a scaffold associated with the nascent complex (i.e. complex not containing the "final" form of a molecule).

The number of reactive groups which appear on a chemical entity is suitably one to ten. A building block featuring only one reactive group can be used e.g. at the end positions of polymers or scaffolds, whereas building blocks having two reactive groups are suitable for the formation of the body part of a polymer or scaffolds capable of being further reacted with the same or a different building block.

One, two or more reactive groups intended for bond formation are typically present on a scaffold. Non-limiting examples of scaffolds are e.g. opiates, steroids, benzodiazepines, hydantoines, and peptidylphosphonates.

The reactive group of a chemical entity may be capable of forming a direct connection to a reactive group of the nascent complex, or the reactive group of the building block may be capable of forming a connection to a reactive group of the nascent complex through a bridging fill-in group. It is to be understood that not all the atoms of a reactive group are necessarily maintained in the connection formed. Rather, the reactive groups are to be regarded as precursors for the structure of the connection.

The subsequent cleavage step to release the chemical entity from the building block can be performed in any appropriate way. In an aspect of the invention the cleavage involves usage of a chemical reagent or an enzyme. The cleavage results in a transfer of the chemical entity to the nascent molecule, or in a transfer of the nascent molecule to the chemical entity of the building block. In some cases it may be advantageous to introduce new chemical groups as a consequence of linker cleavage. The new chemical groups may be used for further reaction in a subsequent cycle, either directly or after having been activated. In other cases it is desirable that no trace of the linker remains after the cleavage.

In another aspect, the connection and the cleavage is conducted as a simultaneous reaction, i.e. either the chemical entity of the building block or the nascent molecule is a leaving group of the reaction. In some aspects of the invention, it is appropriate to design the system such that the connection and the cleavage occur simultaneously because this will reduce the number of steps and the complexity. The simultaneous connection and cleavage can also be designed such that either no trace of the linker remains or such that a new chemical group for further reaction is introduced, as described above.

The attachment of the chemical entity to the building block, optionally via a suitable spacer can be at any entity available for attachment, e.g. the chemical entity can be attached to a nucleobase or the backbone. In general, it is preferred to attach the chemical entity at the phosphor of the internucleoside linkage or at the nucleobase. When the nucleobase is used for attachment of the chemical entity, the attachment point is usually at the 7 position of the purines or 7-deaza-purins or at the 5 position of pyrimidines. The nucleotide may be distanced from the reactive group of the chemical entity by a spacer moiety. The spacer may be designed such that the conformational spaced sampled by the reactive group is optimized for a reaction with the reactive group of the nascent molecule.

The molecules of the invention may have any chemical structure. In a preferred aspect, the molecule can be any compound that may be synthesized in a component-by-component fashion. In some embodiments, the molecule is a linear or branched polymer or oligomer comprising a plurality of linked subunits. In another aspect the molecule is a scaffolded molecule. The term "molecule" also comprises naturally occurring molecules like α-polypeptides etc, however produced in vitro usually in the absence of enzymes, like ribosomes. In certain aspects, the molecule of the library is a non-α-polypeptide.

The molecule may have any molecular weight. However, in order to be orally available, it is in this case preferred that the molecule has a molecular weight less than 2000 Daltons, preferably less than 1000 Dalton, and more preferred less than 500 Daltons.

The size of the library may vary considerably pending on the expected result of the inventive method. In some aspects, it may be sufficient that the library comprises two, three, or four different bifunctional complexes. However, in most events, more than two different bifunctional complexes are desired to obtain a higher diversity. In some aspects, the library comprises 1,000 or more different bifunctional complexes, more preferred 1,000,000 or more different bifunctional complexes. The upper limit for the size of the library is only restricted by the size of the vessel in which the library is comprised. It may be calculated that a vial may comprise up to $10^{14}$ different bifunctional complexes.

Nucleotides

The nucleotides used in the present invention may be linked together in a sequence of nucleotides, i.e. an oligonucleotide. Each nucleotide monomer is normally composed of two parts, namely a nucleobase moiety, and a backbone. The back bone may in some cases be subdivided into a sugar moiety and an internucleoside linker.

The nucleobase moiety may be selected among naturally occurring nucleobases as well as non-naturally occurring nucleobases. Thus, "nucleobase" includes not only the known purine and pyrimidine hetero-cycles, but also heterocyclic analogues and tautomers thereof. Illustrative examples of nucleobases are adenine, guanine, thymine, cytosine, uracil, purine, xanthine, diaminopurine, 8-oxo-$N^6$-methyladenine, 7-deazaxanthine, 7-deazaguanine, $N^4,N^4$-ethanocytosin, $N^6,N^6$-ethano-2,6-diaminopurine, 5-methylcytosine, 5-($C^3$-$C^6$)-alkynylcytosine, 5-fluorouracil, 5-bromouracil, pseudoisocytosine, 2-hydroxy-5-methyl-4-triazolopyridine, isocytosine, isoguanine, inosine and the "non-naturally occurring"

nucleobases described in Benner et al., U.S. Pat. No. 5,432, 272. The term "nucleobase" is intended to cover these examples as well as analogues and tautomers thereof. Especially interesting nucleobases are adenine, guanine, thymine, cytosine, 5-methylcytosine, and uracil, which are considered as the naturally occurring nucleobases in relation to therapeutic and diagnostic application in humans.

Examples of suitable specific pairs of nucleobases are shown below:

Natural Base Pairs

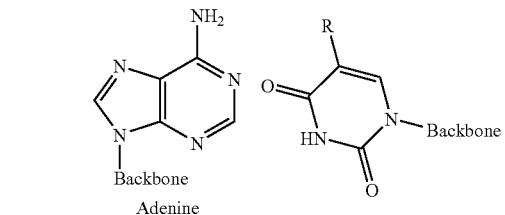

Adenine

R = H: Uracil
R = CH₃: Thymine

Cytosine

Guanine

Synthetic Base Pairs

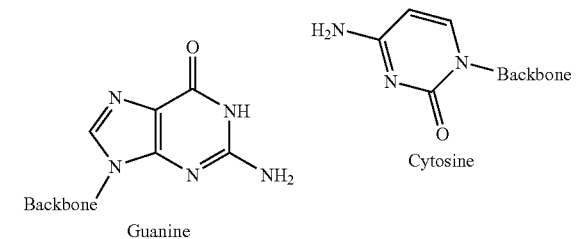

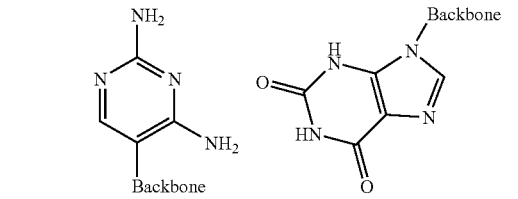

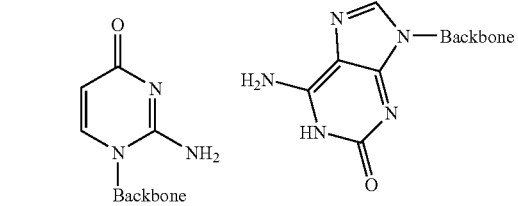

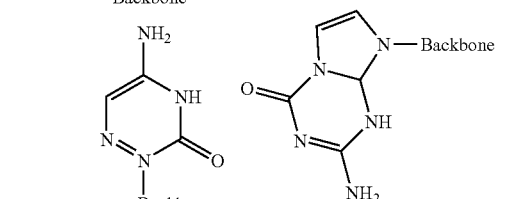

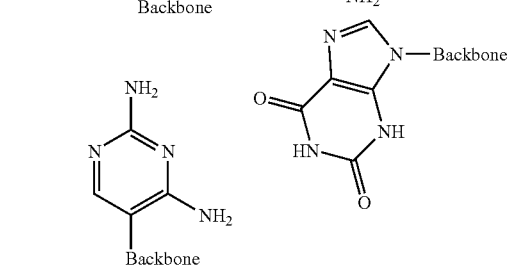

-continued

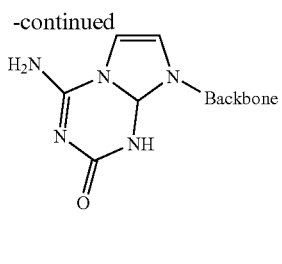

Synthetic purine bases pairring with natural pyrimidines 7-deaza adenine

R = H: Uracil
R = CH₃: Thymine 7-deaza guanine

Cytosine

Suitable examples of backbone units are shown below (B denotes a nucleobase):

DNA     Oxy-LNA     Thio-LNA

Amino-LNA    RNA     Phosphorthioate

R = —H, —CH₃

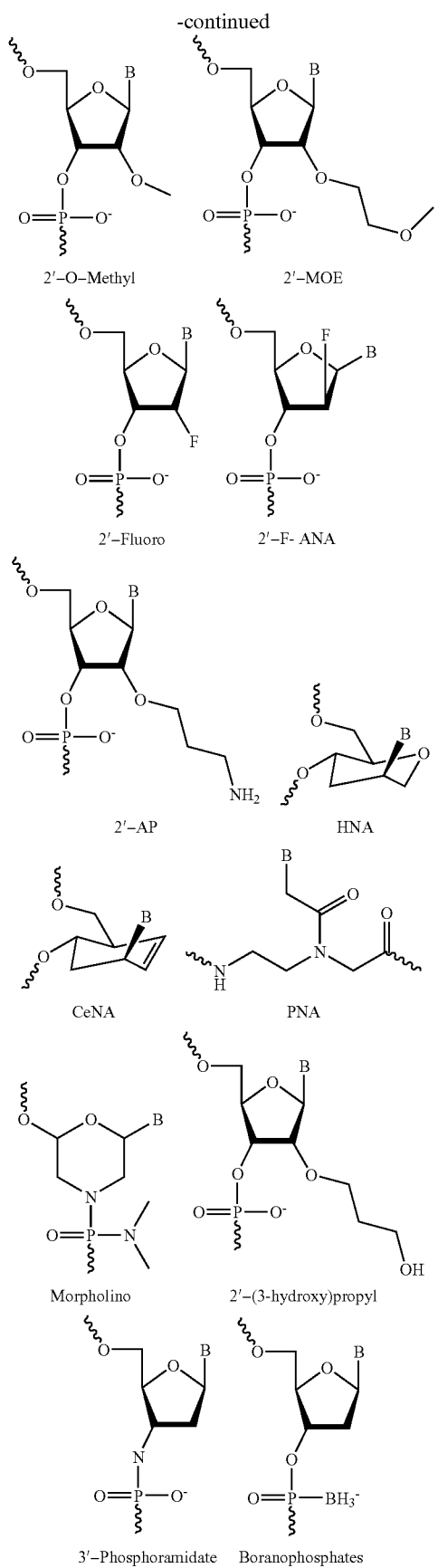

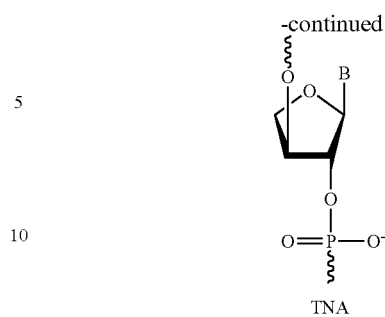

TNA

The sugar moiety of the backbone is suitably a pentose but may be the appropriate part of an PNA or a six-member ring. Suitable examples of possible pentoses include ribose, 2'-deoxyribose, 2'-O-methyl-ribose, 2'-flour-ribose, and 2'-4'-O-methylene-ribose (LNA). Suitably the nucleobase is attached to the 1' position of the pentose entity.

An internucleoside linker connects the 3' end of preceding monomer to a 5' end of a succeeding monomer when the sugar moiety of the backbone is a pentose, like ribose or 2-deoxyribose. The internucleoside linkage may be the natural occurring phosphodiester linkage or a derivative thereof. Examples of such derivatives include phosphorothioate, methylphosphonate, phosphoramidate, phosphotriester, and phosphodithioate. Furthermore, the internucleoside linker can be any of a number of non-phosphorous-containing linkers known in the art.

Preferred nucleic acid monomers include naturally occurring nucleosides forming part of the DNA as well as the RNA family connected through phosphodiester linkages. The members of the DNA family include deoxyadenosine, deoxyguanosine, deoxythymidine, and deoxycytidine. The members of the RNA family include adenosine, guanosine, uridine, cytidine, and inosine. Inosine is a non-specific pairing nucleoside and may be used as universal base because inosine can pair nearly isoenergetically with A, T, and C. Other compounds having the same ability of non-specifically base-pairing with natural nucleobases have been formed. Suitable compounds which may be utilized in the present invention includes among others the compounds depicted below Examples of Universal Bases

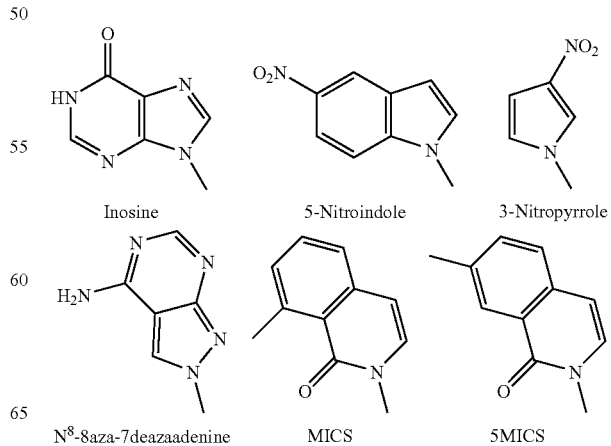

-continued

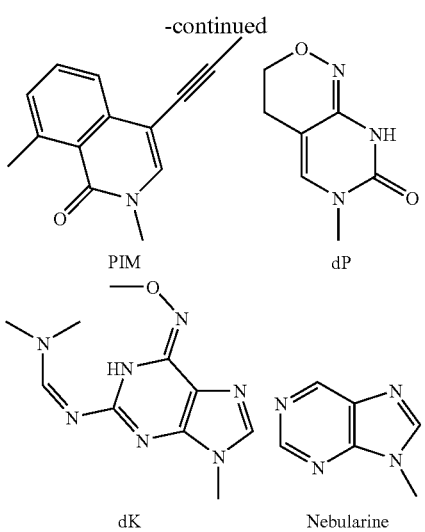

PIM  dP  dK  Nebularine

Building Block

The chemical entities that are precursors for structural additions or eliminations of the molecule may be attached to a building block prior to the participation in the formation of the reaction product leading the final molecule. Besides the chemical entity, the building block generally comprises an oligonucleotide.

The chemical entity of the building block comprises at least one reactive group capable of participating in a reaction which results in a connection between the chemical entity of the building block and another chemical entity or a scaffold associated with the nascent complex. The connection is facilitated by one or more reactive groups of the chemical entity. The number of reactive groups which appear on the chemical entity is suitably one to ten. A building block featuring only one reactive group is used i.a. in the end positions of polymers or scaffolds, whereas building blocks having two reactive groups are suitable for the formation of the body part of a polymer or scaffolds capable of being reacted further. One, two or more reactive groups intended for the formation of connections, are typically present on scaffolds.

The reactive group of the building block may be capable of forming a direct connection to a reactive group of the nascent complex or the reactive group of the building block may be capable of forming a connection to a reactive group of the nascent complex through a bridging fill-in group. It is to be understood that not all the atoms of a reactive group are necessarily maintained in the connection formed. Rather, the reactive groups are to be regarded as precursors for the structure of the connection.

The subsequent cleavage step to release the chemical entity from the building block can be performed in any appropriate way. In an aspect of the invention the cleavage involves usage of a reagent or an enzyme. The cleavage results in a transfer of the chemical entity to the nascent molecule or in a transfer of the nascent molecule to the chemical entity of the building block. In some cases it may be advantageous to introduce new chemical groups as a consequence of linker cleavage. The new chemical groups may be used for further reaction in a subsequent cycle, either directly or after having been activated. In other cases it is desirable that no trace of the linker remains after the cleavage.

In another aspect, the connection and the cleavage is conducted as a simultaneous reaction, i.e. either the chemical entity of the building block or the nascent molecule is a leaving group of the reaction. In general, it is preferred to design the system such that the connection and the cleavage occur simultaneously because this will reduce the number of steps and the complexity. The simultaneous connection and cleavage can also be designed such that either no trace of the linker remains or such that a new chemical group for further reaction is introduced, as described above.

The attachment of the chemical entity to the building block, optionally via a suitable spacer can be at any entity available for attachment, e.g. the chemical entity can be attached to a nucleobase or the backbone. In general, it is preferred to attach the chemical entity at the phosphor of the internucleoside linkage or at the nucleobase. When the nucleobase is used for attachment of the chemical entity, the attachment point is usually at the 7 position of the purines or 7-deaza-purins or at the 5 position of pyrimidines. The nucleotide may be distanced from the reactive group of the chemical entity by a spacer moiety. The spacer may be designed such that the conformational space sampled by the reactive group is optimized for a reaction with the reactive group of the nascent molecule or reactive site.

The oligonucleotide complements the oligonucleotide of the identifier polynucleotide polynucleotide and generally comprises the same number of nucleotides as the oligonucleotide. The oligonucleotide may be adjoined with a fixed sequence, such as a sequence complementing a framing sequence.

Various specific building blocks are envisaged. Building blocks of particular interest are shown below.

Building Blocks Transferring a Chemical Entity to a Recipient Nucleophilic Group The building block indicated below is capable of transferring a chemical entity (CE) to a recipient nucleophilic group, typically an amine group. The bold lower horizontal line illustrates the building block and the vertical line illustrates a spacer. The 5-membered substituted N-hydroxysuccinimid (NHS) ring serves as an activator, i.e. a labile bond is formed between the oxygen atom connected to the NHS ring and the chemical entity. The labile bond may be cleaved by a nucleophilic group, e.g. positioned on a scaffold

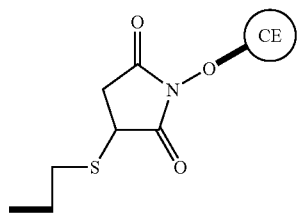

The 5-membered substituted N-hydroxysuccinimid (NHS) ring serves as an activator, i.e. a labile bond is formed between the oxygen atom connected to the NHS ring and the chemical entity. The labile bond may be cleaved by a nucleophilic group, e.g. positioned on a scaffold, to transfer the chemical entity to the scaffold, thus converting the remainder of the fragment into a leaving group of the reaction. When the chemical entity is connected to the activator through an carbonyl group and the recipient group is an amine, the bond formed on the scaffold will an amide bond. The above building block is the subject of the Danish patent application No. PA 2002 01946 and the U.S. provisional patent application No. 60/434,439, the content of which are incorporated herein in their entirety by reference.

Another building block which may form an amide bond is

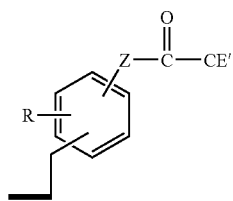

R may be absent or $NO_2$, $CF_3$, halogen, preferably Cl, Br, or I, and Z may be S or O. This type of building block is disclosed in Danish patent application No. PA 2002 0951 and US provisional patent application filed 20 Dec. 2002 with the title "A building block capable of transferring a chemical entity to a recipient reactive group". The content of both patent application are incorporated herein in their entirety by reference.

A nucleophilic group can cleave the linkage between Z and the carbonyl group thereby transferring the chemical entity —(C=O)—CE' to said nucleophilic group.

Building Blocks Transferring a Chemical Entity to a Recipient Reactive Group Forming a C=C Bond A building block as shown below are able to transfer the chemical entity to a recipient aldehylde group thereby forming a double bond between the carbon of the aldehyde and the chemical entity

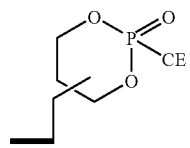

The above building block is comprised by the Danish patent application No. DK PA 2002 01952 and the US provisional patent application filed 20 Dec. 2002 with the title "A building block capable of transferring a chemical entity to a recipient reactive group forming a C=C double bond". The content of both patent applications are incorporated herein in their entirety by reference.

Building Blocks Transferring a Chemical Entity to a Recipient Reactive Group Forming a C—C Bond The below building block is able to transfer the chemical entity to a recipient group thereby forming a single bond between the receiving moiety, e.g. a scaffold, and the chemical entity.

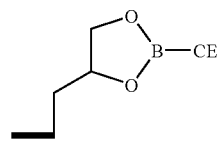

The above building block is comprised by the Danish patent application No. DK PA 2002 01947 and the U.S. provisional patent application No. 60/434,428. The content of both patent applications are incorporated herein in their entirety by reference.

Another building block capable of transferring a chemical entity to a receiving reactive group forming a single bond is

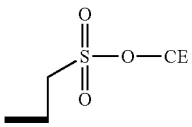

The receiving group may be a nucleophile, such as a group comprising a hetero atom, thereby forming a single bond between the chemical entity and the hetero atom, or the receiving group may be an electronegative carbon atom, thereby forming a C—C bond between the chemical entity and the scaffold.

The chemical entity attached to any of the above building blocks may be a selected from a large arsenal of chemical structures. Examples of chemical entities are H or entities selected among the group consisting of a $C_1$-$C_6$ alkyl, $C_2$-$C_6$ alkenyl, $C_2$-$C_6$ alkynyl, $C_4$-$C_8$ alkadienyl, $C_3$-$C_7$ cycloalkyl, $C_3$-$C_7$ cycloheteroalkyl, aryl, and heteroaryl, said group being substituted with 0-3 $R^4$, 0-3 $R^5$ and 0-3 $R^9$ or $C_1$-$C_3$ alkylene-$NR^4_2$, $C_1$-$C_3$ alkylene-$NR^4C(O)R^8$, $C_1$-$C_3$ alkylene-$NR^4C(O)OR^8$, $C_1$-$C_2$ alkylene-O—$NR^4_2$, $C_1$-$C_2$ alkylene-O—$NR^4C(O)R^8$, $C_1$-$C_2$ alkylene-O—$NR^4C(O)OR^8$ substituted with 0-3 $R^9$.

where $R^4$ is H or selected independently among the group consisting of $C_1$-$C_6$ alkyl, $C_2$-$C_6$ alkenyl, $C_2$-$C_6$ alkynyl, $C_3$-$C_7$ cycloalkyl, $C_3$-$C_7$ cycloheteroalkyl, aryl, heteroaryl, said group being substituted with 0-3 $R^9$ and $R^5$ is selected independently from —$N_3$, —CNO, —C(NOH)$NH_2$, —NHOH, —NHNH$R^6$, —C(O)$R^6$, —Sn$R^6_3$, —B(O$R^6$)$_2$, —P(O)(O$R^6$)$_2$ or the group consisting of $C_2$-$C_6$ alkenyl, $C_2$-$C_6$ alkynyl, $C_4$-$C_8$ alkadienyl said group being substituted with 0-2 $R^7$, where $R^6$ is selected independently from H, $C_1$-$C_6$ alkyl, $C_3$-$C_7$ cycloalkyl, aryl or $C_1$-$C_6$ alkylene-aryl substituted with 0-5 halogen atoms selected from —F, —Cl, —Br, and —I; and $R^7$ is independently selected from —$NO_2$, —COO$R^6$, —CO$R^6$, —CN, —OSi$R^6_3$, —O$R^6$ and —$NR^6_2$.

$R^8$ is H, $C_1$-$C_6$ alkyl, $C_2$-$C_6$ alkenyl, $C_2$-$C_6$ alkynyl, $C_3$-$C_7$ cycloalkyl, aryl or $C_1$-$C_6$ alkylene-aryl substituted with 0-3 substituents independently selected from —F, —Cl, —$NO_2$, —$R^3$, —O$R^3$, —Si$R^3_3$ $R^9$ is =O, —F, —Cl, —Br, —I, —CN, —$NO_2$, —O$R^6$, —$NR^6_2$, —$NR^6$—C(O)$R^8$, —$NR^6$—C(O)O$R^8$, —S$R^6$, —S(O)$R^6$, —S(O)$_2R^6$, —COO$R^6$, —C(O)$NR^6_2$ and —S(O)$_2NR^6_2$.

Cross-Link Cleavage Building Blocks

It may be advantageous to split the transfer of a chemical entity to a recipient reactive group into two separate steps, namely a cross-linking step and a cleavage step because each step can be optimized. A suitable building block for this two step process is illustrated below:

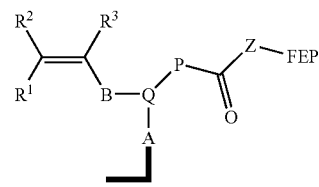

Initially, a reactive group appearing on the chemical entity precursor (abbreviated FEP) reacts with a recipient reactive group, e.g. a reactive group appearing on a scaffold, thereby forming a cross-link. Subsequently, a cleavage is performed, usually by adding an aqueous oxidising agent such as $I_2$, $Br_2$, $Cl_2$, $H^+$, or a Lewis acid. The cleavage results in a transfer of the group HZ-FEP—to the recipient moiety, such as a scaffold.

In the above formula

Z is O, S, $NR^4$

Q is N, $CR^1$

P is a valence bond, O, S, $NR^4$, or a group $C_{5-7}$arylene, $C_{1-6}$alkylene, $C_{1-6}$O-alkylene, $C_{1-6}$S-alkylene, $NR^1$-alkylene, $C_{1-6}$alkylene-O, $C_{1-6}$alkylene-S option said group being substituted with 0-3 $R^4$, 0-3 $R^5$ and 0-3 $R^9$ or $C_1$-$C_3$ alkylene-$NR^4_2$, $C_1$-$C_3$ alkylene-$NR^4C(O)R^8$, $C_1$-$C_3$ alkylene-$NR^4C(O)OR^8$, $C_1$-$C_2$ alkylene-O—$NR^4_2$, $C_1$-$C_2$ alkylene-O—$NR^4C(O)R^8$, $C_1$-$C_2$ alkylene-O—$NR^4C(O)OR^8$ substituted with 0-3 $R^9$, B is a group comprising D-E-F, in which D is a valence bond or a group $C_{1-6}$alkylene, $C_{1-6}$alkenylene, $C_{1-6}$alkynylene, $C_{5-7}$arylene, or $C_{5-7}$heteroarylene, said group optionally being substituted with 1 to 4 group $R^{11}$, E is, when present, a valence bond, O, S, $NR^4$, or a group $C_{1-6}$alkylene, $C_{1-6}$alkenylene, $C_{1-6}$alkynylene, $C_{5-7}$arylene, or $C_{5-7}$heteroarylene, said group optionally being substituted with 1 to 4 group $R^{11}$, F is, when present, a valence bond, O, S, or $NR^4$, A is a spacing group distancing the chemical structure from the complementing element, which may be a nucleic acid, $R^1$, $R^2$, and $R^3$ are independent of each other selected among the group consisting of H, $C_1$-$C_6$ alkyl, $C_2$-$C_6$ alkenyl, $C_2$-$C_6$ alkynyl, $C_4$-$C_8$ alkadienyl, $C_3$-$C_7$ cycloalkyl, $C_3$-$C_7$ cycloheteroalkyl, aryl, and heteroaryl, said group being substituted with 0-3 $R^4$, 0-3 $R^5$ and 0-3 $R^9$ or $C_1$-$C_3$ alkylene-$NR^4_2$, $C_1$-$C_3$ alkylene-$NR^4C(O)R^8$, $C_1$-$C_3$ alkylene-$NR^4C(O)OR^8$, $C_1$-$C_2$ alkylene-O—$NR^4_2$, $C_1$-$C_2$ alkylene-O—$NR^4C(O)R^8$, $C_1$-$C_2$ alkylene-O—$NR^4C(O)OR^8$ substituted with 0-3 $R^9$, FEP is a group selected among the group consisting of H, $C_1$-$C_6$ alkyl, $C_2$-$C_6$ alkenyl, $C_2$-$C_6$ alkynyl, $C_4$-$C_8$ alkadienyl, $C_3$-$C_7$ cycloalkyl, $C_3$-$C_7$ cycloheteroalkyl, aryl, and heteroaryl, said group being substituted with 0-3 $R^4$, 0-3 $R^5$ and 0-3 $R^9$ or $C_1$-$C_3$ alkylene-$NR^4_2$, $C_1$-$C_3$ alkylene-$NR^4C(O)R^8$, $C_1$-$C_3$ alkylene-$NR^4C(O)OR^8$, $C_1$-$C_2$ alkylene-O—$NR^4_2$, $C_1$-$C_2$ alkylene-O—$NR^4C(O)R^8$, $C_1$-$C_2$ alkylene-O—$NR^4C(O)OR^8$ substituted with 0-3 $R^9$, where $R^4$ is H or selected independently among the group consisting of $C_1$-$C_6$ alkyl, $C_2$-$C_6$ alkenyl, $C_2$-$C_6$ alkynyl, $C_3$-$C_7$ cycloalkyl, $C_3$-$C_7$ cycloheteroalkyl, aryl, heteroaryl, said group being substituted with 0-3 $R^9$ and $R^5$ is selected independently from —$N_3$, —CNO, —C(NOH)$NH_2$, —NHOH, —$NHNHR^6$, —C(O)$R^6$, —$SnR^6_3$, —B(O$R^6$)$_2$, —P(O)(O$R^6$)$_2$ or the group consisting of $C_2$-$C_6$ alkenyl, $C_2$-$C_6$ alkynyl, $C_4$-$C_8$ alkadienyl said group being substituted with 0-2 $R^7$, where $R^6$ is selected independently from H, $C_1$-$C_6$ alkyl, $C_3$-$C_7$ cycloalkyl, aryl or $C_1$-$C_6$ alkylene-aryl substituted with 0-5 halogen atoms selected from —F, —Cl, —Br, and —I; and $R^7$ is independently selected from —$NO_2$, —COO$R^6$, —COR$^6$, —CN, —OSi$R^6_3$, —O$R^6$ and —$NR^6_2$.

$R^8$ is H, $C_1$-$C_6$ alkyl, $C_2$-$C_6$ alkenyl, $C_2$-$C_6$ alkynyl, $C_3$-$C_7$ cycloalkyl, aryl or $C_1$-$C_6$ alkylene-aryl substituted with 0-3 substituents independently selected from —F, —Cl, —$NO_2$, —$R^3$, —$R^3$, —Si$R^3_3$ $R^9$ is =O, —F, —Cl, —Br, —I, —CN, —$NO_2$, —O$R^6$, —$NR^6_2$, —$NR^6$—C(O)$R^8$, —$NR^6$—C(O)O$R^8$, —S$R^6$, —S(O)$R^6$, —S(O)$_2R^6$, —COO$R^6$, —C(O)$NR^6_2$ and —S(O)$_2NR^6_2$.

In a preferred embodiment Z is O or S, P is a valence bond, Q is CH, B is $CH_2$, and $R^1$, $R^2$, and $R^3$ is H. The bond between the carbonyl group and Z is cleavable with aqueous $I_2$.

Contacting Between Target and Library

The contacting step, by which the library of bifunctional molecules is subjected under binding conditions to a target, may be referred to as the enrichment step or the selection step, as appropriate, and includes the screening of the library for molecules having predetermined desirable characteristics. Predetermined desirable characteristics can include binding to a target, catalytically changing the target, chemically reacting with a target in a manner which alters/modifies the target or the functional activity of the target, and covalently attaching to the target as in a suicide inhibitor.

In theory, molecules of interest can be selected based on their properties using either physical or physiological procedures. The method preferred according to the present invention is to enrich molecules with respect to binding affinity towards a target of interest. In a certain embodiment, the basic steps involve mixing the library of bifunctional complexes with the immobilized target of interest. The target can be attached to a column matrix or microtitre wells with direct immobilization or by means of antibody binding or other high-affinity interactions. In another embodiment, the target and displayed molecules interact without immobilisation of the target. Displayed molecules that bind to the target will be retained on this surface, while nonbinding displayed molecules will be removed during a single or a series of wash steps. The identifier polynucleotides of bifunctional complexes bound to the target can then be separated by cleaving the physical connection to the molecule. It may be considered advantageously to perform a chromatography step after of instead of the washing step. After the cleavage of the physical link between the molecule and the identifier polynucleotide, the identifier polynucleotide may be recovered from the media and optionally amplified before the decoding step.

A significant reduction in background binders may be obtained with increased washing volumes, repeating washing steps, higher detergent concentrations and prolonged incubation during washing. Thus, the more volume and number of steps used in the washing procedure together with more stringent conditions will more efficiently remove non-binders and background binders. The right stringency in the washing step can also be used to remove low-affinity specific binders. However, the washing step will also remove wanted binders if too harsh conditions are used.

A blocking step, such as incubation of solid phase with skimmed milk proteins or other inert proteins and/or mild detergent such as Tween-20 and Triton X-100, may also be used to reduce the background. The washing conditions should be as stringent as possible to remove background binding but to retain specific binders that interact with the immobilized target. Generally, washing conditions are adjusted to maintain the desired affinity binders, e.g. binders in the micromolar, nanomolar, or pocomolar range.

In traditional elution protocols, false positives due to suboptimal binding and washing conditions are difficult to circumvent and may require elaborate adjustments of experimental conditions. However, an enrichment of more than 100 to 1000 is rarely obtained. The present invention alleviates the problem with false positive being obtained because the non-specific binding bifunctional complexes to a large extent remain in the reaction chamber. The experiments reported herein suggest that an enrichment of more than $10^7$ can be obtained.

The target can be any compound of interest. E.g. the target can be a protein, peptide, carbohydrate, polysaccharide, glycoprotein, hormone, receptor, antigen, antibody, virus, substrate, metabolite, transition state analogue, cofactor, inhibitor, drug, dye, nutrient, growth factor, cell, tissue, etc. without limitation. Suitable targets include, but are not limited to, angiotensin converting enzyme, renin, cyclooxygenase, 5-lipoxygenase, IIL-10 converting enzyme, cytokine receptors, PDGF receptor, type II inosine monophosphate dehydrogenase, β-lactamases, integrin, proteases like factor VIIa, kinases like Bcr-Abl/Her, phosphotases like PTP-1B, and fungal cytochrome P-450. Targets can include, but are not limited to, bradykinin, neutrophil elastase, the HIV proteins, including tat, rev, gag, int, RT, nucleocapsid etc., VEGF, bFGF, TGFβ, KGF, PDGF, GPCR, thrombin, substance P, IgE, sPLA2, red blood cells, glioblastomas, fibrin clots, PBMCs, hCG, lectins, selectins, cytokines, ICP4, complement proteins, etc.

A target can also be a surface of a non-biological origin, such as a polymer surface or a metal surface. The method of the invention may then be used to identify suitable coatings for such surfaces.

In a preferred embodiment, the desirable molecule acts on the target without any interaction between the nucleic acid attached to the desirable molecule and the target. In one embodiment, the bound complex-target aggregate can be partitioned from unbound bifunctional complexes by a number of methods. The methods include nitrocellulose filter binding, column chromatography, filtration, affinity chromatography, centrifugation, and other well known methods. A preferred method is size-exclusion chromatography.

Briefly, the library of bifunctional complexes is subjected to the target, which may include contact between the library and a column onto which the target is immobilised. Identifier polynucleotides associated with undesirable molecules, i.e. molecules not bound to the target under the stringency conditions used, will pass through the column. Additional undesirable molecules (e.g. molecules which cross-react with other targets) may be removed by counter-selection methods. Desirable bifunctional complexes are bound to the column. The target may be immobilized in a number of ways. In one embodiment, the target is immobilized through a cleavable physical link, such as one more chemical bonds. The aggregate of the target and the complex may then be subjected to a size exclusion chromatography to separate the aggregate from the rest of the compounds in the media. The complex may then be eluted from the target by changing the conditions (e.g., salt, pH, surfactant, temperature etc.). Alternatively, the complex may be provided with a cleavable linker, preferable orthogonal to the cleavable linker that attached the target to the solid support, at a position between the molecule and the identifier polynucleotide. Subsequent to the size exclusion chromatography this cleavable linker is cleaved to separate the identifier polynucleotides of bifunctional complexes having affinity towards the targets. Just to mention a single type of orthogonal cleavable linkages, one could attach the target to the solid support through a linkage that can be cleaved by a chemical agent, and the linker separating the molecule and the identifier polynucleotide may be selected as a photocleavable linkage. More specifically, the former linkage may be a disulphide bond that can be cleaved by a suitable reducing agent like DTT (dithiothreitol) and the latter linkage may be a o-nitrophenyl group.

There are other partitioning and screening processes which are compatible with this invention that are known to one of ordinary skill in the art. In one embodiment, the products can be fractionated by a number of common methods and then each fraction is then assayed for activity. The fractionization methods can include size, pH, hydrophobicity, etc.

Inherent in the present method is the selection of molecules on the basis of a desired function; this can be extended to the selection of molecules with a desired function and specificity. Specificity can be required during the selection process by first extracting bifunctional complexes which are capable of interacting with a non-desired "target" (negative selection, or counter-selection), followed by positive selection with the desired target. As an example, inhibitors of fungal cytochrome P-450 are known to cross-react to some extent with mammalian cytochrome P-450 (resulting in serious side effects). Highly specific inhibitors of the fungal cytochrome could be selected from a library by first removing those bifunctional complexes capable of interacting with the mammalian cytochrome, followed by retention of the remaining products which are capable of interacting with the fungal cytochrome.

Cleavable Linkers

A cleavable linker may be positioned between the target and a solid support or between the potential drug candidate and the identifier polynucleotide or any other position that may ensure a separation of the identifier polynucleotide from successful bifunctional complexes from non-specific binding bifunctional complexes. The cleavable linker may be selectively cleavable, i.e. conditions may selected that only cleave that particular linker.

The cleavable linkers may be selected from a large plethora of chemical structures. Examples of linkers includes, but are not limited to, linkers having an enzymatic cleavage site, linkers comprising a chemical degradable component, linkers cleavable by electromagnetic radiation.

Examples of Linkers Cleavable by Electromagnetic Radiation (Light)

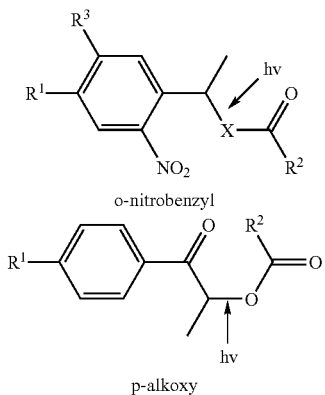

O-Nitrobenzyl in Exo Position

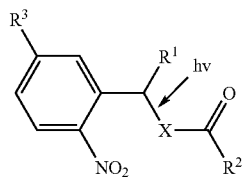

For more details see Holmes C P. J. Org. Chem. 1997, 62, 2370-2380

3-Nitrophenyloxy

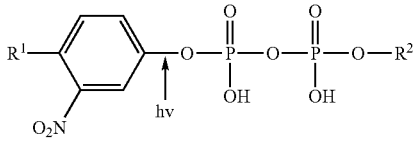

For more details see Rajasekharan Pillai, V. N. Synthesis. 1980, 1-26

Dansyl Derivatives:

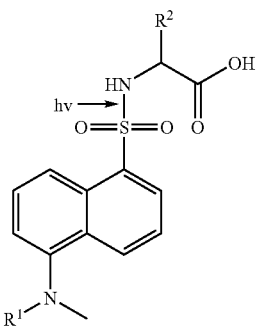

For more details see Rajasekharan Pillai, V. N. Synthesis. 1980, 1-26

Coumarin Derivatives

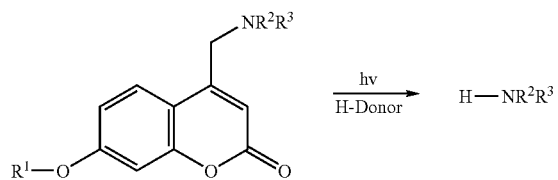

For more details see R. O, Schoenleber, B. Giese. Synlett 2003, 501-504

$R^1$ and $R^2$ can be either of the potential drug candidate and the identifier polynucleotide, respectively. Alternatively, $R^1$ and $R^2$ can be either of the target or a solid support, respectively.

$R^3$=H or $OCH_3$

If X is O then the product will be a carboxylic acid

If X is NH the product will be a carboxamide

One specific example is the PC Spacer Phosphoramidite (Glen research catalog #10-4913-90) which can be introduced in an oligonucleotide during synthesis and cleaved by subjecting the sample in water to UV light (~300-350 nm) for 30 seconds to 1 minute.

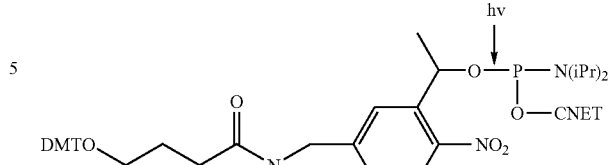

DMT=4,4'-Dimethoxytrityl iPr=Isopropyl

CNEt=Cyanoethyl

The above PC spacer phosphoamidite is suitable incorporated in a library of bifunctional complexes at a position between the identifier and the potential drug candidate. The spacer may be cleaved according to the following reaction.

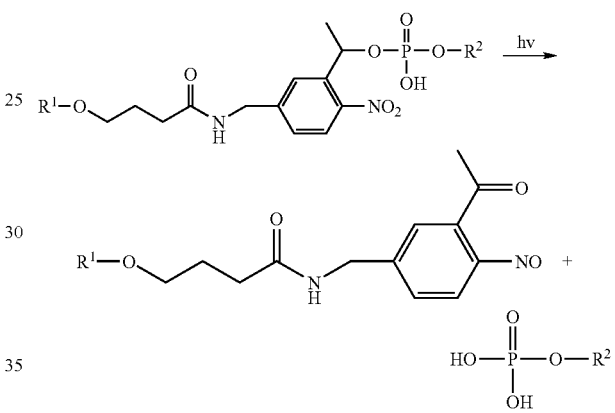

$R^1$ and $R^2$ can be either of the molecule and the identifying molecule, respectively. In a preferred aspect $R^2$ is an oligonucleotide identifier polynucleotide and the $R^1$ is the potential drug candidate. When the linker is cleaved a phosphate group is generated allowing for further biological reactions. As an example, the phosphate group may be positioned in the 5' end of an oligonucleotide allowing for an enzymatic ligation process to take place.

Examples of Linkers Cleavable by Chemical Agents:

Ester linkers can be cleaved by nucleophilic attack using e.g. hydroxide ions. In practice this can be accomplished by subjecting the target-ligand complex to a base for a short period.

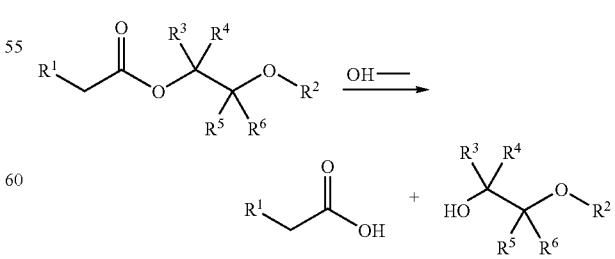

$R^1$ and $R^2$ can be the either of be the potential drug candidate or the identifier polynucleotide, respectively. $R^{4-6}$ can be any of the following: H, CN, F, $NO_2$, $SO_2NR_2$.

Disulfide linkers can efficiently be cleaved/reduced by Tris (2-carboxyethyl) phosphine (TCEP). TCEP selectively and completely reduces even the most stable water-soluble alkyl disulfides over a wide pH range. These reductions frequently required less than 5 minutes at room temperature. TCEP is a non-volatile and odorless reductant and unlike most other reducing agents, it is resistant to air oxidation. Trialkylphosphines such as TCEP are stable in aqueous solution, selectively reduce disulfide bonds, and are essentially unreactive toward other functional groups commonly found in proteins.

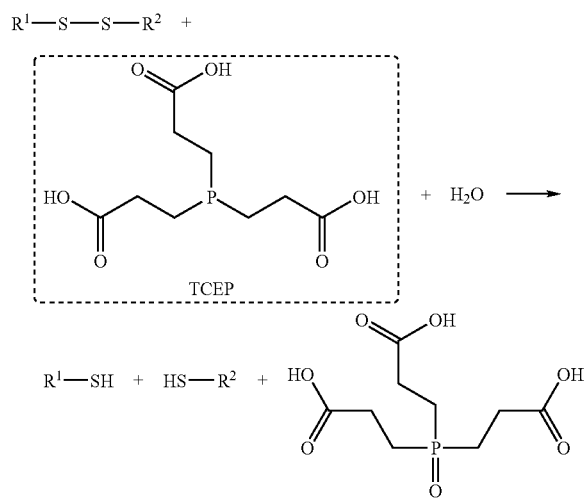

More details on the reduction of disulfide bonds can be found in Kirley, T. L. (1989), Reduction and fluorescent labeling of cyst(e)ine-containing proteins for subsequent structural analysis, *Anal. Biochem.* 180, 231 and Levison, M. E., et al. (1969), Reduction of biological substances by water-soluble phosphines: Gamma-globulin *Experentia* 25, 126-127.

Linkers Cleavable by Enzymes

The linker connecting the potential drug candidate with the identifier polynucleotide or the solid support and the target can include a peptide region that allows a specific cleavage using a protease. This is a well-known strategy in molecular biology. Site-specific proteases and their cognate target amino acid sequences are often used to remove the fusion protein tags that facilitate enhanced expression, solubility, secretion or purification of the fusion protein.

Various proteases can be used to accomplish a specific cleavage. The specificity is especially important when the cleavage site is presented together with other sequences such as for example the fusion proteins. Various conditions have been optimized in order to enhance the cleavage efficiency and control the specificity. These conditions are available and know in the art.

Enterokinase is one example of an enzyme (serine protease) that cut a specific amino acid sequence. Enterokinase recognition site is Asp-Asp-Asp-Asp-Lys (DDDDK), and it cleaves C-terminally of Lys. Purified recombinant Enterokinase is commercially available and is highly active over wide ranges in pH (pH 4.5-9.5) and temperature (4-45° C.).

The nuclear inclusion protease from tobacco etch virus (TEV) is another commercially available and well-characterized proteases that can be used to cut at a specific amino acid sequence. TEV protease cleaves the sequence Glu-Asn-Leu-Tyr-Phe-Gln-Gly/Ser (ENLYFQG/S) between Gln-Gly or Gln-Ser with high specificity.

Another well-known protease is thrombin that specifically cleaves the sequence Leu-Val-Pro-Arg-Gly-Ser (LVPAGS) between Arg-Gly. Thrombin has also been used for cleavage of recombinant fusion proteins. Other sequences can also be used for thrombin cleavage; these sequences are more or less specific and more or less efficiently cleaved by thrombin. Thrombin is a highly active protease and various reaction conditions are known to the public.

Activated coagulation factor FX (FXa) is also known to be a specific and useful protease. This enzyme cleaves C-terminal of Arg at the sequence Ile-Glu-Gly-Arg (IEGR). FXa is frequently used to cut between fusion proteins when producing proteins with recombinant technology. Other recognition sequences can also be used for FXa.

Other types of proteolytic enzymes can also be used that recognize specific amino acid sequences. In addition, proteolytic enzymes that cleave amino acid sequences in an un-specific manner can also be used if only the linker contains an amino acid sequence in the complex molecule.

Other type of molecules such as ribozymes, catalytically active antibodies, or lipases can also be used. The only prerequisite is that the catalytically active molecule can cleave the specific structure used as the linker, or as a part of the linker, that connects the encoding region and the displayed molecule or, in the alternative the solid support and the target.

A variety of endonucleases are available that recognize and cleave a double stranded nucleic acid having a specific sequence of nucleotides. The endonuclease Eco RI is an example of a nuclease that efficiently cuts a nucleotide sequence linker comprising the sequence GAATTC also when this sequence is close to the nucleotide sequence length. Purified recombinant Eco RI is commercially available and is highly active in a range of buffer conditions. As an example the Eco RI is working in various protocols as indicted below (NEBuffer is available from New England Biolabs):

NEBuffer 1: [10 mM Bis Tris Propane-HCl, 10 mM $MgCl_2$, 1 mM dithiothreitol (pH 7.0 at 25° C.)], NEBuffer 2: [50 mM NaCl, 10 mM Tris-HCl, 10 mM $MgCl_2$, 1 mM dithiothreitol (pH 7.9 at 25° C.)], NEBuffer 3: [100 mM NaCl, 50 mM Tris-HCl, 10 mM $MgCl_2$, 1 mM dithiothreitol (pH 7.9 at 25° C.)], NEBuffer 4: [50 mM potassium acetate, 20 mM Tris-acetate, 10 mM magnesium acetate, 1 mM dithiothreitol (pH 7.9 at 25° C.)].

Extension buffer: mM KCl, 20 mM Tris-HCl(Ph 8.8 at 25° C.), 10 mM $(NH_4)_2SO_4$, 2 mM $MgSO_4$ and 0.1% Triton X-100, and 200 μM dNTPs.

Determining the Identifier Polynucleotide

The nucleotide sequence of the identifier polynucleotide present in the isolated bifunctional molecules or the separated identifiers is determined to identify the chemical entities that participated in the binding interaction. The synthesis method of the molecule may be established if information on the chemical entities as well as the point in time they have been incorporated in the molecule can be deduced from the identifier polynucleotide. It may be sufficient to get information on the chemical structure of the various chemical entities that have participated in the molecule to deduce the full molecule due to structural constraints during the formation. As an example, the use of different kinds of attachment chemistries may ensure that a chemical entity on a building block can only be transferred to a single position on a scaffold. Another kind of chemical constrains may be present due to steric hindrance on the scaffold molecule or the chemical entity to be transferred. In general however, it is preferred that information can be inferred from the identifier polynucleotide that enable the identification of each of the chemical entities that have participated in the formation of the molecule along with the point in time in the synthesis history the chemical entities have been incorporated in the (nascent) molecule.

Although conventional DNA sequencing methods are readily available and useful for this determination, the amount and quality of isolated bifunctional molecule may require additional manipulations prior to a sequencing reaction.

Where the amount is low, it is preferred to increase the amount of the identifier polynucleotide by polymerase chain reaction (PCR) using PCR primers directed primer binding sites present in the identifier polynucleotide.

In addition, the quality of the isolated bifunctional molecule may be such that multiple species of bifunctional molecule are co-isolated by virtue of similar capacities for binding to the target. In cases where more than one species of bifunctional molecule are isolated, the different isolated species must be separated prior to sequencing of the identifier oligonucleotide.

Thus in one embodiment, the different identifier polynucleotides of the isolated bifunctional complexes are cloned into separate sequencing vectors prior to determining their sequence by DNA sequencing methods. This is typically accomplished by amplifying all of the different identifier polynucleotides by PCR as described herein, and then using a unique restriction endonuclease sites on the amplified product to directionally clone the amplified fragments into sequencing vectors. The cloning and sequencing of the amplified fragments then is a routine procedure that can be carried out by any of a number of molecular biological methods known in the art.

Alternatively, the bifunctional complex or the PCR amplified identifier polynucleotide can be analysed in a microarray. The array may be designed to analyse the presence of a single oligonucleotide or multiple oligonucleotides in a identifier polynucleotide.

Synthesis of Nucleic Acids

Oligonucleotides can be synthesized by a variety of chemistries as is well known. For synthesis of an oligonucleotide on a substrate in the direction of 3' to 5', a free hydroxy terminus is required that can be conveniently blocked and deblocked as needed. A preferred hydroxy terminus blocking group is a dimexothytrityl ether (DMT). DMT blocked termini are first deblocked, such as by treatment with 3% dichloroacetic acid in dichloromethane (DCM) as is well known for oligonucleotide synthesis, to form a free hydroxy terminus.

Nucleotides in precursor form for addition to a free hydroxy terminus in the direction of 3' to 5' require a phosphoramidate moiety having an aminodiisopropyl side chain at the 3' terminus of a nucleotide. In addition, the free hydroxy of the phosphoramidate is blocked with a cyanoethyl ester (OCNET), and the 5' terminus is blocked with a DMT ether. The addition of a 5' DMT-, 3' OCNET-blocked phosphoramidate nucleotide to a free hydroxyl requires tetrazole in acetonitrile followed by iodine oxidation and capping of unreacted hydroxyls with acetic anhydride, as is well known for oligonucleotide synthesis. The resulting product contains an added nucleotide residue with a DMT blocked 5' terminus, ready for deblocking and addition of a subsequent blocked nucleotide as before.

For synthesis of an oligonucleotide in the direction of 5' to 3', a free hydroxy terminus on the linker is required as before. However, the blocked nucleotide to be added has the blocking chemistries reversed on its 5' and 3' termini to facilitate addition in the opposite orientation. A nucleotide with a free 3' hydroxyl and 5' DMT ether is first blocked at the 3' hydroxy terminus by reaction with TBS-Cl in imidazole to form a TBS ester at the 3' terminus. Then the DMT-blocked 5' terminus is deblocked with DCA in DCM as before to form a free 5' hydroxy terminus. The reagent (N,N-diisopropylamino)(cyanoethyl) phosphonamidic chloride having an aminodiisopropyl group and an OCNET ester is reacted in tetrahydrofuran (THF) with the 5' deblocked nucleotide to form the aminodiisopropyl-, OCNET-blocked phosphonamidate group on the 5' terminus. Thereafter the 3' TBS ester is removed with tetrabutylammonium fluoride (TBAF) in DCM to form a nucleotide with the phosphonamidate-blocked 5' terminus and a free 3' hydroxy terminus. Reaction in base with DMT-Cl adds a DMT ether blocking group to the 3' hydroxy terminus.

The addition of the 3' DMT-, 5' OCNET-blocked phosphonamidated nucleotide to a linker substrate having a free hydroxy terminus then proceeds using the previous tetrazole reaction, as is well known for oligonucleotide polymerization. The resulting product contains an added nucleotide residue with a DMT-blocked 3' terminus, ready for deblocking with DCA in DCM and the addition of a subsequent blocked nucleotide as before.

Extension and Amplification

The use of the polymerase chain reaction (PCR) is a preferred embodiment, for the production of the identifiers using the nucleic acids of the selected bifunctional complexes as identifiers.

For use in this invention, the identifier polynucleotides are preferably comprised of polynucleotide coding strands, such as mRNA and/or the sense strand of genomic DNA or non-natural nucleic acids, like TNA and LNA which may be used as template for a polymerase. If the genetic material to be processed is in the form of double stranded nucleic acid, it is usually first denatured, typically by melting, into single strands. The nucleic acid is subjected to a PCR reaction by treating (contacting) the sample with a PCR primer pair, each member of the pair having a preselected nucleotide sequence. The PCR primer pair is capable of initiating primer extension reactions by hybridizing to the PCR primer binding site on identifier oligonucleotide, preferably at least about 10 nucleotides in length, more preferably at least about 12 nucleotides in length. The first primer of a PCR primer pair is sometimes referred to as the "anti-sense primer" because it is extended into a non-coding or anti-sense strand of a nucleic acid, i.e., a strand complementary to a coding strand. The second primer of a PCR primer pair is sometimes referred to as the "sense primer" because it is adjoined with the coding or sense strand of a nucleic acid.

The PCR reaction is performed by mixing the PCR primer pair, preferably a predetermined amount thereof, with the nucleic acids of the sample, preferably a predetermined amount thereof, in a PCR buffer to form a PCR reaction admixture. The admixture is thermocycled for a number of cycles, which is typically predetermined, sufficient for the formation of a PCR reaction product, thereby amplifying the identifiers in the isolated complex.

PCR is typically carried out by thermocycling i.e., repeatedly increasing and decreasing the temperature of a PCR reaction admixture within a temperature range whose lower limit is about 30 degrees Celsius (30° C.) to about 55° C. and whose upper limit is about 90° C. to about 100° C. The increasing and decreasing can be continuous, but is preferably phasic with time periods of relative temperature stability at each of temperatures favoring polynucleotide synthesis, denaturation and hybridization.

A plurality of first primer and/or a plurality of second primers can be used in each amplification, e.g., one species of first primer can be paired with a number of different second primers to form several different primer pairs. Alternatively, an individual pair of first and second primers can be used. In any case, the amplification products of amplifications using the same or different combinations of first and second primers can be combined for assaying for mutations.

The PCR reaction is performed using any suitable method. Generally it occurs in a buffered aqueous solution, i.e., a PCR buffer, preferably at a pH of 7-9, most preferably about 8. Preferably, a molar excess of the primer is admixed to the buffer containing the identifier strand. A large molar excess is preferred to improve the efficiency of the process.

The PCR buffer also contains the deoxyribonucleotide triphosphates (polynucleotide synthesis substrates) dATP, dCTP, dGTP, and dTTP and a polymerase, typically thermostable, all in adequate amounts for primer extension (polynucleotide synthesis) reaction. The resulting solution (PCR admixture) is heated to about 90° C.-100° C. for about 1 to 10 minutes, preferably from 1 to 4 minutes. After this heating period the solution is allowed to cool to a primer hybridization temperature. The synthesis reaction may occur at from room temperature up to a temperature above which the polymerase (inducing agent) no longer functions efficiently. Thus, for example, if DNA polymerase is used as inducing agent, the temperature is generally no greater than about 40° C. The thermocycling is repeated until the desired amount of PCR product is produced. An exemplary PCR buffer comprises the following: 50 mM KCl; 10 mM Tris-HCl at pH 8.3; 1.5 mM MgCl2; 0.001% (wt/vol) gelatin, 200 µM dATP; 200 µM dTTP; 200 µM dCTP; 200 µM dGTP; and 2.5 units *Thermus aquaticus* (Taq) DNA polymerase I (U.S. Pat. No. 4,889,818) per 100 microliters (µl) of buffer.

The inducing agent may be any compound or system which will function to accomplish the synthesis of primer extension products, including enzymes. Suitable enzymes for this purpose include, for example, *E. coli* DNA polymerase I, Klenow fragment of *E. coli* DNA polymerase I, T4 DNA polymerase, Taq DNA polymerase, Pfu polymerase, Vent polymerase, HIV-1 Reverse Transcriptase, other available DNA polymerases, reverse transcriptase, and other enzymes, including heat-stable enzymes, which will facilitate combination of the nucleotides in the proper manner to form the primer extension products which are complementary to each nucleic acid strand. Generally, the synthesis will be initiated at the 3' end of each primer and proceed in the 5' direction along the identifier strand, until synthesis terminates, producing molecules of different lengths. There may be inducing agents, however, which initiate synthesis at the 5' end and proceed in the above direction, using the same process as described above.

The inducing agent also may be a compound or system which will function to accomplish the synthesis of RNA primer extension products, including enzymes. In preferred embodiments, the inducing agent may be a DNA-dependent RNA polymerase such as T7 RNA polymerase, T3 RNA polymerase or SP6 RNA polymerase. These polymerases produce a complementary RNA polynucleotide. The high turn-over rate of the RNA polymerase amplifies the starting polynucleotide as has been described by Chamberlin et al., The Enzymes, ed. P. Boyer, pp. 87-108, Academic Press, New York (1982). Amplification systems based on transcription have been described by Gingeras et al., in PCR Protocols, A Guide to Methods and Applications, pp. 245-252, Innis et al., eds, Academic Press, Inc., San Diego, Calif. (1990).

If the inducing agent is a DNA-dependent RNA polymerase and, therefore incorporates ribonucleotide triphosphates, sufficient amounts of ATP, CTP, GTP and UTP are admixed to the primer extension reaction admixture and the resulting solution is treated as described above.

The newly synthesized strand and its complementary nucleic acid strand form a double-stranded molecule which can be used in the succeeding steps of the method. PCR amplification methods are described in detail in U.S. Pat. Nos. 4,683,192, 4,683,202, 4,800,159, and 4,965,188, and at least in several texts including PCR Technology: Principles and Applications for DNA Amplification, H. Erlich, ed., Stockton Press, New York (1989); and PCR Protocols: A Guide to Methods and Applications, Innis et al., eds., Academic Press, San Diego, Calif. (1990). The term "primer" as used herein refers to a polynucleotide whether purified from a nucleic acid restriction digest or produced synthetically, which is capable of acting as a point of initiation of nucleic acid synthesis when placed under conditions in which synthesis of a primer extension product which is complementary to a nucleic acid strand is induced, i.e., in the presence of nucleotides and an agent for polymerization such as DNA polymerase, reverse transcriptase and the like, and at a suitable temperature and pH. The primer is preferably single stranded for maximum efficiency, but may alternatively be in double stranded form. If double stranded, the primer is first treated to separate it from its complementary strand before being used to prepare extension products. Preferably, the primer is a polydeoxyribonucleotide. The primer must be sufficiently long to prime the synthesis of extension products in the presence of the agents for polymerization. The exact lengths of the primers will depend on many factors, including temperature and the source of primer. For example, depending on the complexity of the target sequence, a polynucleotide primer typically contains 10 to 25 or more nucleotides, although it can contain fewer nucleotides. Short primer molecules generally require cooler temperatures to form sufficiently stable hybrid bifunctional complexes with identifier.

The primers used herein are selected to be "substantially" complementary to the different strands of each specific sequence to be synthesized or amplified. This means that the primer must be sufficiently complementary to non-randomly hybridize with its respective identifier strand. Therefore, the primer sequence may or may not reflect the exact sequence of the identifier. For example, a non-complementary nucleic acid can be attached to the 5' end of the primer, with the remainder of the primer sequence being substantially complementary to the strand. Such non-complementary fragments typically code for an endonuclease restriction site or used as a linker to connect to a label, such as biotin.

Primers of the present invention may also contain a DNA-dependent RNA polymerase promoter sequence or its complement. See for example, Krieg et al., Nucl. Acids Res., 12:7057-70 (1984); Studier et al., J. Mol. Biol., 189:113-130 (1986); and Molecular Cloning: A Laboratory Manual, Second Edition, Maniatis et al., eds., Cold Spring Harbor, N.Y. (1989).

When a primer containing a DNA-dependent RNA polymerase promoter is used, the primer is hybridized to the polynucleotide strand to be amplified and the second polynucleotide strand of the DNA-dependent RNA polymerase promoter is completed using an inducing agent such as *E. coli* DNA polymerase I, or the Klenow fragment of *E. coli* DNA polymerase. The starting polynucleotide is amplified by alternating between the production of an RNA polynucleotide and DNA polynucleotide. This may be used for selective degradation of the RNA strand, which is prone to disintegration upon treatment with a strong base.

Primers may also contain a identifier polynucleotide or replication initiation site for a RNA-directed RNA polymerase. Typical RNA-directed RNA polymerase include the QB replicase described by Lizardi et al., Biotechnology, 6:1197-1202 (1988). RNA-directed polymerases produce large numbers of RNA strands from a small number of identifier RNA strands that contain a identifier polynucleotide or replication initiation site. These polymerases typically give a one million-fold amplification of the identifier strand as has been described by Kramer et al., J. Mol. Biol., 89:719-736 (1974).

In one embodiment, the present invention utilizes a set of polynucleotides that form primers having a priming region located at the 3'-terminus of the primer. The 3'-terminal priming portion of each primer is capable of acting as a primer to catalyze nucleic acid synthesis, i.e., initiate a primer extension reaction off its 3' terminus. One or both of the primers can additionally contain a 5'-terminal non-priming portion, i.e., a region that does not participate in hybridization to the preferred identifier. The 5'-part of the primer may be labelled as described herein above.

The invention claimed is:

1. A method for synthesising one or more bifunctional complexes each comprising a) a molecule resulting from the reaction of a plurality of chemical entities and b) an identifier polynucleotide identifying one or more or all of the chemical entities having participated in the synthesis of the molecule, said method comprising the steps of:
   i) providing a plurality of building blocks at least some of which comprise one or more chemical entities linked to an identifier oligonucleotide,
   ii) providing one or more connector oligonucleotides capable of hybridising to the identifier oligonucleotides of the building blocks provided in step i),
   iii) hybridising identifier oligonucleotides of the building blocks to the one or more connector oligonucleotides,
   iv) ligating identifier oligonucleotides hybridised to connector oligonucleotide(s), thereby generating an identifier polynucleotide comprising covalently linked identifier oligonucleotides at least some of which are linked to one or more chemical entities,
   v) separating the identifier polynucleotide from the one or more optionally ligated connector oligonucleotide(s),
   vi) reacting the chemical entities linked to the identifier polynucleotide in the absence of hybridisation between identifier oligonucleotides and connector oligonucleotides, and
   vii) obtaining a bifunctional complex comprising a molecule resulting from the reaction of the chemical entities, said molecule being linked to an identifier polynucleotide identifying at least some of the chemical entities having participated in the synthesis of the molecule.

2. The method of claim 1, wherein at least one building block identifier oligonucleotide or at least one connector oligonucleotide is attached to a solid support.

3. The method of claim 1 comprising the steps of
   immobilising at least one building block comprising an identifier oligonucleotide to a solid support,
   hybridising said immobilized building block oligonucleotide to a first connector oligonucleotide,
   hybridising at least one additional building block oligonucleotide to said first connector oligonucleotide,
   ligating building block oligonucleotides hybridised to the connector oligonucleotide,
   separating the connector oligonucleotide from the ligated building block oligonucleotides,
   reacting one or more chemical entities associated with different building block oligonucleotides, which are ligated and separated,
   obtaining a first bifunctional complex comprising a first molecule, linked to a first identifier polynucleotide identifying at least some of the chemical entities having participated in the synthesis of the first molecule,
   wherein said first bifunctional complex is optionally immobilised to the solid support.

4. The method of claim 3, wherein said chemical entities are reacted in a reaction compartment from which the connector oligonucleotide has been removed in a washing and/or separation step prior to the reaction of said chemical entities.

5. The method of claim 3 comprising the steps of
   providing a second connector oligonucleotide,
   hybridising said second connector oligonucleotide to the identifier polynucleotide of said first bifunctional complex comprising a first molecule,
   hybridising at least one further oligonucleotide of a building block to said second connector oligonucleotide,
   ligating building block oligonucleotides hybridised to the second connector oligonucleotide, wherein at least one of said building block oligonucleotides are hybridised to the first identifier polynucleotide,
   separating the second connector oligonucleotide from the ligated building block oligonucleotides,
   reacting the first molecule with the one or more chemical entities associated with the ligated building block oligonucleotide(s),
   obtaining a second bifunctional complex comprising a second molecule, linked to a second identifier polynucleotide identifying at least some of the chemical entities having participated in the synthesis of the second molecule,
   wherein said second bifunctional complex is optionally immobilised to a solid support.

6. The method of claim 1, wherein each step for providing a connector and a building block is repeated for different connect or oligonucleotides and different further building blocks.

7. The method of claim 2, wherein said bifunctional complex, or a plurality of such complexes, is released from the solid support to which it is immobilised.

8. The method of claim 1,
   wherein different bifunctional complexes are generated in different reaction compartments,
   wherein at least some of said different bifunctional complexes are combined in a further reaction compartment comprising a plurality of further connector oligonucleotides,
   wherein at least two of said different bifunctional complexes hybridise to a further connector oligonucleotide,
   wherein the molecule precursor part of said complexes react, thereby generating a further molecule in the form of a reaction product,
   wherein the identifier polynucleotides of said bifunctional complexes are optionally covalently linked prior to, during, and/or after, the reaction of the molecule precursors,
   wherein the covalently linked identifier polynucleotides are optionally separated from the further connector oligonucleotide prior to or after reaction of said molecule precursors.

9. A method for synthesising a bifunctional complex comprising a molecule resulting from the reaction of a plurality of chemical entities, wherein said molecule is linked to an identifier polynucleotide identifying one or more of the chemical entities having participated in the synthesis of the molecule, said method comprising the steps of:
   i) providing a plurality of building blocks selected from the group consisting of
   a) building blocks comprising an identifier oligonucleotide linked to one or more chemical entities,
   b) building blocks comprising an identifier oligonucleotide linked to one or more reactive groups, and
   c) connector oligonucleotides to which building blocks of groups a) and b) can hybridise,
   ii) generating a hybridisation complex comprising at least n building blocks by hybridising the identifier oligonucleotide of one building block to the identifier oligonucleotide of at least one other building block, wherein n is an integer of 4 or more,
   wherein at least 3 of said at least n building blocks comprise a chemical entity,
   wherein no single identifier oligonucleotide is hybridised to all of the remaining identifier oligonucleotides,
   wherein optionally at least one of said building blocks of group c) is immobilised to a solid support, thereby providing a handle to which an oligonucleotide of at least one building block of groups a) or b) can hybridise, iii) covalently linking identifier oligonucleotides of building blocks comprising one or more chemical entities, thereby obtaining at least one identifier polynucleotide comprising covalently linked identifier oligonucleotides each associated with one or more chemical entities, iv) optionally separating said identifier polynucleotide obtained in step iii) from any optionally immobilised connector oligonucleotides hybridised thereto, wherein said separation optionally comprises the step of diverting said identifier polynucleotide comprising covalently linked identifier oligonucleotides each associated with one or more chemical entities to a different reaction compartment, thereby separating said identifier polynucleotide from said optionally immobilised connector oligonucleotides, v) reacting said at least 3 chemical entities linked to the identifier polynucleotide in the absence of hybridisation between identifier oligonucleotides and connector oligonucleotides, and vi) obtaining a bifunctional complex comprising a molecule resulting from the reaction of a plurality of chemical entities, wherein said molecule is linked to an identifier polynucleotide identifying one or more of the chemical entities having participated in the synthesis of the molecule.

10. The method of claim 9 wherein a plurality of different bifunctional complexes is obtained by repeating the method steps for different building blocks.

11. The method of claim 1,
wherein a plurality of molecules are synthesized,
wherein the plurality of synthesised molecules are selected from the group consisting of α-peptides, β-peptides, γ-peptides, ω-peptides, mono-, di- and tri-substituted α-peptides, β-peptides, γ-peptides, ω-peptides, peptides wherein the amino acid residues are in the L-form or in the D-form, vinylogous polypeptides, glycopoly-peptides, polyamides, vinylogous sulfonamide peptides, polysulfonamides, conjugated peptides, polyesters, polysaccharides, polycarbamates, polycarbonates, polyureas, polypeptidyiphosphonates, polyurethanes, azatides, oligo N-substituted glycines, polyethers, ethoxyformacetal oligomers, poly-thioethers, polyethylene glycols (PEG), polyethylenes, polydisulfides, polyarylene sulfides, polynucleotides, PNAs, LNAs, morpholinos, oligo pyrrolinones, polyoximes, polyimines, polyethyleneimines, polyimides, polyacetals, polyacetates, polystyrenes, polyvinyl, lipids, phospholipids, glycolipids, polycyclic compounds and combinations thereof,
wherein each molecule is synthesised by reacting a plurality of chemical entities in the range of from 2 to 200.

12. The method of claim 1, wherein the reaction of chemical entities involve at least two reactive groups of at least one chemical entity.

13. The method of claim 1, wherein each connector oligonucleotide comprises or consists of a sequence of nucleotides.

14. The method of claim 1, each connector oligonucleotide having from 3 to 30 nucleotides.

15. The method of claim 1, wherein at least one of said building blocks comprise a chemical entity comprising a scaffold moiety comprising a plurality of reactive groups.

16. The method of claim 15, wherein said scaffold moiety reactive groups react with one or more chemical entities of a single building block, or with one or more chemical entities of different building blocks.

17. The method of claim 1, wherein at least one chemical entity reaction is an acylation reaction.

18. The method of claim 1, wherein at least one chemical entity comprises an amine, and wherein an amide bond is formed when at least one chemical entity is reacted.

19. A method for generating a library of bifunctional complexes comprising a molecule and an identifier polynucleotide capable of identifying the chemical entities having participated in the synthesis of the molecule, or identifying the reaction steps having led to the synthesis of the molecule, said method comprising the steps of:

hybridising a plurality of building block identifier oligonucleotides to a plurality of connector oligonucleotides each capable of hybridising to one or more building block oligonucleotides, said building block identifier oligonucleotides being linked to one or more chemical entities, covalently linking said building block oligonucleotides hybridised to one or more connector oligonucleotides, thereby generating a plurality of identifier polynucleotides linked to a plurality of non-reacted chemical entities, separating the identifier polynucleotides from the optionally ligated connector oligonucleotides, reacting chemical entities linked to each of a plurality of different identifier polynucleotides, and generating a library of bifunctional complexes each comprising a different molecule and an identifier polynucleotide identifying the chemical entities having participated in the synthesis of the molecule, wherein each of the plurality of molecules are generated by reacting at least 2 chemical entities associated with different building block oligonucleotides.

20. A method for synthesising a plurality of different molecules, said method comprising (1) providing a plurality of connector oligonucleotides each capable of hybridizing to at least 1 complementary connector oligonucleotide, (2) providing a plurality of complementary connector oligonucleotides selected from the group consisting of
a) complementary connector oligonucleotides comprising at least 1 chemical entity comprising at least 1 reactive group,
b) complementary connector oligonucleotides comprising at least 1 reactive group,
c) complementary connector oligonucleotides comprising at least 1 spacer region, (3) hybridizing the plurality of connector oligonucleotides and complementary connector oligonucleotides, thereby forming a plurality of different hybridisation complexes, each hybridisation complex comprising at least 2 complementary connector oligonucleotides and at least 2 connector oligonucleotides,
wherein, for each of said hybridisation complexes,
at least 2 of said complementary connector oligonucleotides comprise at least 1 chemical entity comprising at least 1 reactive group, and
at least 1 of said complementary connector oligonucleotides hybridizes to at least 2 connector oligonucleotides, (4) ligating, enzymatically, chemically, or otherwise, complementary connector oligonucleotides, thereby forming identifier polynucleotides, wherein each identifier polynucleotide is associated with a plurality of unreacted chemical entities, (5) separating each identifier polynucleotide associated with unreacted chemical entities from optionally ligated connector oligonucleotides associated therewith, and (6) reacting, when the identifier polynucleotides are no longer hybridised to the optionally ligated connector oligonucleotides, at least 2 chemical entity reactive groups of each identifier polynucleotide by reacting at least 1 reactive group of each chemical entity, wherein, for each bifunctional complex, the reaction of said chemical entity reactive groups results in the formation of a different molecule by reacting at least 2 chemical entities provided by separate complementary connector oligonucleotides, thereby synthesising a plurality of different molecules.

21. The method of claim 20 comprising the further step of selecting molecules having desirable characteristics, wherein the selection employs a predetermined assaying procedure.

22. The method of claim 20 comprising the further step of amplifying at least part of the individual and optionally ligated connector oligonucleotides used for the formation of the initial hybridisation complexes.

23. The method of claim 22 comprising the further step of contacting a population of said amplified, optionally ligated connector oligonucleotides, or fragments thereof, with a plurality of building block oligonucleotides.

24. The method of claim 23 comprising the further step of performing an additional synthesis round by carrying out the steps (1)-(6) using, as the provided connector oligonucleotides of step (1), a population of said amplified connector oligonucleotides, or a population of said amplified connector oligonucleotide fragments.

25. The method of claim 1, wherein the identifier polynucleotide at step vii identifies all of the chemical entities having participated in the synthesis of the molecule.

26. The method of claim 9, wherein all chemical entities to be reacted are linked to the same identifier polynucleotide.

27. The method of claim 19, wherein separating the identifier polynucleotide from the optionally ligated connector oligonucleotides is performed by degrading the optionally ligated connector oligonucleotides and/or by performing a washing step wherein the identifier polynucleotides are associated with a solid support capable of being separated from non-bound, optionally ligated connector oligonucleotides.

* * * * *

```
                         SEQUENCE LISTING

<160> NUMBER OF SEQ ID NOS: 26

<210> SEQ ID NO 1
<211> LENGTH: 12
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (5)..(8)
<223> OTHER INFORMATION: N denotes a random nucleobase, preferably
      selected from G, A, C, T, or U

<400> SEQUENCE: 1
gcggnnnncg cg                                                            12

<210> SEQ ID NO 2
<211> LENGTH: 12
<212> TYPE: DNA
<213> ORGANISM: Artificial Sequence
<220> FEATURE:
<223> OTHER INFORMATION: Synthetic construct

<400> SEQUENCE: 2
gcggattacg cg                                                            12

<210> SEQ ID NO 3
<211> LENGTH: 12
<212> TYPE: DNA
<213> ORGANISM: Artificial Sequence
<220> FEATURE:
<223> OTHER INFORMATION: Synthetic construct

<400> SEQUENCE: 3
gcggaattcg cg                                                            12

<210> SEQ ID NO 4
<211> LENGTH: 12
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (5)..(8)
<223> OTHER INFORMATION: N denotes a random nucleobase, preferably
      selected from G, A, C, T, or U

<400> SEQUENCE: 4
taatnnnntt aa                                                            12
```

```
<210> SEQ ID NO 5
<211> LENGTH: 12
<212> TYPE: DNA
<213> ORGANISM: Artificial Sequence
<220> FEATURE:
<223> OTHER INFORMATION: Synthetic construct

<400> SEQUENCE: 5
taatgccgtt aa                                                              12

<210> SEQ ID NO 6
<211> LENGTH: 12
<212> TYPE: DNA
<213> ORGANISM: Artificial Sequence
<220> FEATURE:
<223> OTHER INFORMATION: Synthetic construct

<400> SEQUENCE: 6
taatgggctt aa                                                              12

<210> SEQ ID NO 7
<211> LENGTH: 22
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (10)..(13)
<223> OTHER INFORMATION: N denotes a random nucleobase, preferably
      selected from G, A, C, T, or U

<400> SEQUENCE: 7
tttttggaan nnnagagttt tt                                                   22

<210> SEQ ID NO 8
<211> LENGTH: 22
<212> TYPE: DNA
<213> ORGANISM: Artificial Sequence
<220> FEATURE:
<223> OTHER INFORMATION: Synthetic construct

<400> SEQUENCE: 8
tttttggaac cttagagttt tt                                                   22

<210> SEQ ID NO 9
<211> LENGTH: 22
<212> TYPE: DNA
<213> ORGANISM: Artificial Sequence
<220> FEATURE:
<223> OTHER INFORMATION: Synthetic construct

<400> SEQUENCE: 9
tttttggaac ttcagagttt tt                                                   22

<210> SEQ ID NO 10
<211> LENGTH: 12
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (5)..(8)
<223> OTHER INFORMATION: N denotes a random nucleobase, preferably
      selected from G, A, C, T, or U
```

-continued

```
<400> SEQUENCE: 10
ggttnnnngt tg                                                            12

<210> SEQ ID NO 11
<211> LENGTH: 12
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (5)..(8)
<223> OTHER INFORMATION: N denotes a random nucleobase, preferably
      selected from G, A, C, T, or U

<400> SEQUENCE: 11
accannnncc aa                                                            12

<210> SEQ ID NO 12
<211> LENGTH: 12
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (5)..(8)
<223> OTHER INFORMATION: N denotes a random nucleobase, preferably
      selected from G, A, C, T, or U

<400> SEQUENCE: 12
tctcnnnncc tt                                                            12

<210> SEQ ID NO 13
<211> LENGTH: 25
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (5)..(8)
<223> OTHER INFORMATION: N denotes a random nucleobase, preferably
      selected from G, A, C, T, or U
<220> FEATURE:
<221> NAME/KEY: misc_feature
<222> LOCATION: (22)..(25)
<223> OTHER INFORMATION: N denotes a random nucleobase, preferably
      selected from G, A, C, T, or U

<400> SEQUENCE: 13
cgcgnnnncc gcaaaaactc tnnnn                                              25

<210> SEQ ID NO 14
<211> LENGTH: 25
<212> TYPE: DNA
<213> ORGANISM: Artificial Sequence
<220> FEATURE:
<223> OTHER INFORMATION: Synthetic construct

<400> SEQUENCE: 14
cgcgtaatcc gcaaaaactc taagg                                              25

<210> SEQ ID NO 15
<211> LENGTH: 33
<212> TYPE: DNA
<213> ORGANISM: Artificial Sequence
<220> FEATURE:
<223> OTHER INFORMATION: Synthetic construct
```

```
<220> FEATURE:
<221> NAME/KEY: misc_feature
<222> LOCATION: (14)..(17)
<223> OTHER INFORMATION: N denotes a random nucleobase, preferably
      selected from G, A, C, T, or U
<220> FEATURE:
<221> NAME/KEY: misc_feature
<222> LOCATION: (26)..(29)
<223> OTHER INFORMATION: N denotes a random nucleobase, preferably
      selected from G, A, C, T, or U

<400> SEQUENCE: 15
ttccaaaaac aacnnnnaac cttggnnnnt ggt                                33

<210> SEQ ID NO 16
<211> LENGTH: 21
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (14)..(17)
<223> OTHER INFORMATION: N denotes a random nucleobase, preferably
      selected from G, A, C, T, or U

<400> SEQUENCE: 16
ttccaaaaac aacnnnnaac c                                             21

<210> SEQ ID NO 17
<211> LENGTH: 10
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(1)
<223> OTHER INFORMATION: n represents inosine (I)
<220> FEATURE:
<221> NAME/KEY: misc_feature
<222> LOCATION: (3)..(3)
<223> OTHER INFORMATION: n represents inosine (I)
<220> FEATURE:
<221> NAME/KEY: misc_feature
<222> LOCATION: (5)..(5)
<223> OTHER INFORMATION: n represents inosine (I)

<400> SEQUENCE: 17 ntntntggtg                                                          10

<210> SEQ ID NO 18
<211> LENGTH: 10
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(1)
<223> OTHER INFORMATION: n represents inosine (I)
<220> FEATURE:
<221> NAME/KEY: misc_feature
<222> LOCATION: (3)..(3)
<223> OTHER INFORMATION: n represents inosine (I)
<220> FEATURE:
<221> NAME/KEY: misc_feature
<222> LOCATION: (5)..(5)
<223> OTHER INFORMATION: n represents inosine (I)

<400> SEQUENCE: 18 ntntntgggt                                                          10
```

```
<210> SEQ ID NO 19
<211> LENGTH: 20
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(1)
<223> OTHER INFORMATION: n represents inosine (I)
<220> FEATURE:
<221> NAME/KEY: misc_feature
<222> LOCATION: (3)..(3)
<223> OTHER INFORMATION: n represents inosine (I)
<220> FEATURE:
<221> NAME/KEY: misc_feature
<222> LOCATION: (5)..(5)
<223> OTHER INFORMATION: n represents inosine (I)
<220> FEATURE:
<221> NAME/KEY: misc_feature
<222> LOCATION: (13)..(13)
<223> OTHER INFORMATION: n represents inosine (I)
<220> FEATURE:
<221> NAME/KEY: misc_feature
<222> LOCATION: (15)..(15)
<223> OTHER INFORMATION: n represents inosine (I)
<220> FEATURE:
<221> NAME/KEY: misc_feature
<222> LOCATION: (18)..(18)
<223> OTHER INFORMATION: n represents inosine (I)

<400> SEQUENCE: 19
ntntntggtt ttntnttntg                                               20

<210> SEQ ID NO 20
<211> LENGTH: 20
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(1)
<223> OTHER INFORMATION: n represents inosine (I)
<220> FEATURE:
<221> NAME/KEY: misc_feature
<222> LOCATION: (3)..(3)
<223> OTHER INFORMATION: n represents inosine (I)
<220> FEATURE:
<221> NAME/KEY: misc_feature
<222> LOCATION: (5)..(5)
<223> OTHER INFORMATION: n represents inosine (I)
<220> FEATURE:
<221> NAME/KEY: misc_feature
<222> LOCATION: (13)..(13)
<223> OTHER INFORMATION: n represents inosine (I)
<220> FEATURE:
<221> NAME/KEY: misc_feature
<222> LOCATION: (15)..(15)
<223> OTHER INFORMATION: n represents inosine (I)
<220> FEATURE:
<221> NAME/KEY: misc_feature
<222> LOCATION: (18)..(18)
<223> OTHER INFORMATION: n represents inosine (I)

<400> SEQUENCE: 20
ntntntgggg ggntnttntg                                               20

<210> SEQ ID NO 21
<211> LENGTH: 20
<212> TYPE: DNA
<213> ORGANISM: Artificial Sequence
<220> FEATURE:
<223> OTHER INFORMATION: Synthetic construct
```

```
<220> FEATURE:
<221> NAME/KEY: misc_feature
<222> LOCATION: (1)..(1)
<223> OTHER INFORMATION: n represents inosine (I)
<220> FEATURE:
<221> NAME/KEY: misc_feature
<222> LOCATION: (3)..(3)
<223> OTHER INFORMATION: n represents inosine (I)
<220> FEATURE:
<221> NAME/KEY: misc_feature
<222> LOCATION: (5)..(5)
<223> OTHER INFORMATION: n represents inosine (I)
<220> FEATURE:
<221> NAME/KEY: misc_feature
<222> LOCATION: (13)..(13)
<223> OTHER INFORMATION: n represents inosine (I)
<220> FEATURE:
<221> NAME/KEY: misc_feature
<222> LOCATION: (15)..(15)
<223> OTHER INFORMATION: n represents inosine (I)
<220> FEATURE:
<221> NAME/KEY: misc_feature
<222> LOCATION: (18)..(18)
<223> OTHER INFORMATION: n represents inosine (I)

<400> SEQUENCE: 21
ntntntggtg tgntnttntg                                              20

<210> SEQ ID NO 22
<211> LENGTH: 10
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (3)..(3)
<223> OTHER INFORMATION: n represents inosine (I)
<220> FEATURE:
<221> NAME/KEY: misc_feature
<222> LOCATION: (5)..(5)
<223> OTHER INFORMATION: n represents inosine (I)
<220> FEATURE:
<221> NAME/KEY: misc_feature
<222> LOCATION: (8)..(8)
<223> OTHER INFORMATION: n represents inosine (I)

<400> SEQUENCE: 22 gtntnttntg                                                         10

<210> SEQ ID NO 23
<211> LENGTH: 10
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (3)..(3)
<223> OTHER INFORMATION: n represents inosine (I)
<220> FEATURE:
<221> NAME/KEY: misc_feature
<222> LOCATION: (5)..(5)
<223> OTHER INFORMATION: n represents inosine (I)
<220> FEATURE:
<221> NAME/KEY: misc_feature
<222> LOCATION: (8)..(8)
<223> OTHER INFORMATION: n represents inosine (I)

<400> SEQUENCE: 23 ttntnttntg                                                         10
```

```
<210> SEQ ID NO 24
<211> LENGTH: 20
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(1)
<223> OTHER INFORMATION: N denotes a random nucleobase
<220> FEATURE:
<221> NAME/KEY: misc_feature
<222> LOCATION: (2)..(2)
<223> OTHER INFORMATION: N denotes a random nucleobase
<220> FEATURE:
<221> NAME/KEY: misc_feature
<222> LOCATION: (19)..(19)
<223> OTHER INFORMATION: N denotes a random nucleobase
<220> FEATURE:
<221> NAME/KEY: misc_feature
<222> LOCATION: (20)..(20)
<223> OTHER INFORMATION: N denotes a random nucleobase

<400> SEQUENCE: 24
nnccacacac cacaacacnn                                              20

<210> SEQ ID NO 25
<211> LENGTH: 10
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(1)
<223> OTHER INFORMATION: N denotes a random nucleobase
<220> FEATURE:
<221> NAME/KEY: misc_feature
<222> LOCATION: (2)..(2)
<223> OTHER INFORMATION: N denotes a random nucleobase

<400> SEQUENCE: 25 nnccacacac                                                         10

<210> SEQ ID NO 26
<211> LENGTH: 10
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(2)
<223> OTHER INFORMATION: N denotes a random nucleobase
<220> FEATURE:
<221> NAME/KEY: misc_feature
<222> LOCATION: (3)..(3)
<223> OTHER INFORMATION: N denotes inosine (I)
<220> FEATURE:
<221> NAME/KEY: misc_feature
<222> LOCATION: (5)..(5)
<223> OTHER INFORMATION: N denotes inosine (I)
<220> FEATURE:
<221> NAME/KEY: misc_feature
<222> LOCATION: (8)..(8)
<223> OTHER INFORMATION: N denotes inosine (I)

<400> SEQUENCE: 26 nnntnttntg                                                         10
```